United States Patent [19]
Kraus et al.

[11] Patent Number: 5,883,081
[45] Date of Patent: Mar. 16, 1999

[54] ISOLATION OF NOVEL HIV-2 PROVIRUSES

[75] Inventors: Gunter Kraus, La Jolla; Flossie Wong-Staal, San Diego, both of Calif.; Randy Talbott, Princeton, N.J.; Eric M. Poeschla, San Diego, Calif.

[73] Assignee: The Regents of the University of California, Oakland, Calif.

[21] Appl. No.: 659,251

[22] Filed: Jun. 7, 1996

Related U.S. Application Data

[60] Provisional application No. 60/001,441 Jul. 26, 1995.
[51] Int. Cl.⁶ .......................... A01N 43/04; A61K 39/42; C12P 21/06; C12N 15/00
[52] U.S. Cl. ...................... 514/44; 424/160.1; 435/69.1; 435/320.1; 530/388.35; 536/23.1
[58] Field of Search ................. 424/160.1; 435/69.1, 435/320.1; 514/44; 530/388.35; 536/23.1

[56] References Cited

U.S. PATENT DOCUMENTS

| | | | |
|---|---|---|---|
| 4,861,719 | 8/1989 | Miller | 435/236 |
| 5,079,342 | 1/1992 | Alizon et al. | 530/324 |

OTHER PUBLICATIONS

Proc. Natl. Acad. Sci. USA, vol. 90, issued May 1993, Talbott, et al., "Mapping the Determinants of Human Immunodeficiency Virus 2 for Infectivity, Replication Efficiency, and Cytopathicity," pp. 4226–4230.

Proc. Natl. Acad. Sci. USA, vol. 86, issued Apr. 1989, Franchini, et al., "Molecular and Biological Characterization of a Replication Competent Human Immunodeficiency Type 2 (HIV–2) Proviral Clone," pp. 2433–2437.

Aids Research and Human Retroviruses, vol. 11, No. 7, issued Jul. 1995, Galabru, et al., "Nucleotide Sequence of the HIV–2 EHO Genome, a Divergent HIV–2 Isolate," pp. 873–874.

Zagury et al., In Vitro Characterization of a Biologically Active Molecular Clone of HIV–2NIH–Z Containing a nef Deletion and Expressing a Full–Length Transmembrane Protein, Aids Research and Human Retroviruses, vol. 6, No. 9, see Abstract, p. 1081, col, 1990.

Garzino–Demo, et al., Human Immunodeficiency Virus Type 2 (HIV–2): Packaging Signal and Associated Negative Regulatory Element, Human Gene Therapy 6:177–184, see Abstract, Feb. 1995.

Primary Examiner—Jeffrey Stucker
Assistant Examiner—Hankyel Park
Attorney, Agent, or Firm—Townsend and Townsend and Crew

[57] ABSTRACT

Novel HIV-2 proviruses, molecular clones, nucleic acids, polypeptides, viruses and viral components are described. The use of these compositions as components of diagnostic assays, as immunological reagents, as vaccines, as components of packaging cells, cell transduction vectors, and as gene therapy vectors is also described.

27 Claims, 15 Drawing Sheets

FIG. 1B

HOMOLOGY OF HIV-2$_{KR}$ WITH OTHER HIV-2 AND SIV VIRUSES

| KR GENE | HIV-2 ST | HIV-2 BEN | HIV-2 GH1 | HIV-2 ISY | HIV-2 ROD | HIV-2 D194 | HIV-2 NIH-Z | HIV-1 BRU | SIV AGM |
|---|---|---|---|---|---|---|---|---|---|
| gag | 98% | 97% | 98% | 97% | 98% | 97% | 97% | 81% | 84% |
| pol | 91% | 89% | 89% | 91% | 91% | 89% | 89% | 55% | 55% |
| vif | 97% | 96% | 95% | 96% | 96% | 96% | 96% | 65% | 74% |
| vpr | 92% | 78% | 91% | 95% | 94% | 90% | 95% | 74% | 86% |
| vpx | 94% | 88% | 93% | 92% | 93% | 92% | 88% | NA | 67% |
| tat | 92% | 93% | 92% | 94% | 93% | 92% | 93% | 52% | 62% |
| rev | 94% | 91% | 90% | 91% | 94% | 92% | 94% | 73% | 66% |
| env | 95% | 93% | 81% | 93% | 94% | 93% | 94% | 72% | 68% |
| nef | 92% | 91% | 89% | 92% | 92% | 91% | 62% | 62% | 68% |
| Mean | 94% | 91% | 91% | 94% | 94% | 93% | 90% | 59% | 70% |

FIG. 2A

```
                                        (Oct like ?)                    > ce II <                > ce I? <
                                        ——X—X——                         ————————                  ——X—X——
              410         420         430         440         450
HIV2KR        CAGGAAGTAG--ATGATGAAACTGC------AGGGACTTTCCAGAAGGGGCTGTAAC
HIV2ST        ................ACT.AC.GA.....A..TGAGACTGC...............T..
HIV2BEN       ................CT.CT.A.......A..TGAGGCTGC..................
HIV2D194      ..............A.CT.CT.A.......A..TGAGACTGC..................
HIV2ISY       ................CT.CTGA.......A..TGAGACTGC..................
HIV2ROD       ................ACT.AC.G.......A..TGAGACTGC..................
HIV2NIHZ      ................CT.CTGA.......A..TGAGACTGC..................
Consensus     ................CT.CT.A.......A..TGAGACTGC..................

H2B1                                                Signal ->
              > SpI-III <  > SpI-II <            > SpI-I? <
              —————————    —————————             ——XX—X——
              460         470         480         490         500         510
HIV2KR        CAGGGGAGGGACGTGGGAGGAACCGGTGGGAACGCCCT-CATACTT-CTGTATAAATGT
HIV2ST        ...A.................G..............-.......-.......T......
HIV2BEN       ...A.................A..........G.T..-......A-......T.CT...
HIV2D194      ...A.................A..........G.T..-........-.....T.CT...
HIV2ISY       ...A.................A..........G.T..-........-......T.....
HIV2ROD       ...A..A..............A..........G.T..-......T.-.....T.CT...A.
HIV2NIHZ      ...A.................A..........G.T..-........-......T.....
Consensus     ...A.................A..........G.T..-........-......T.....
```

FIG. 4A
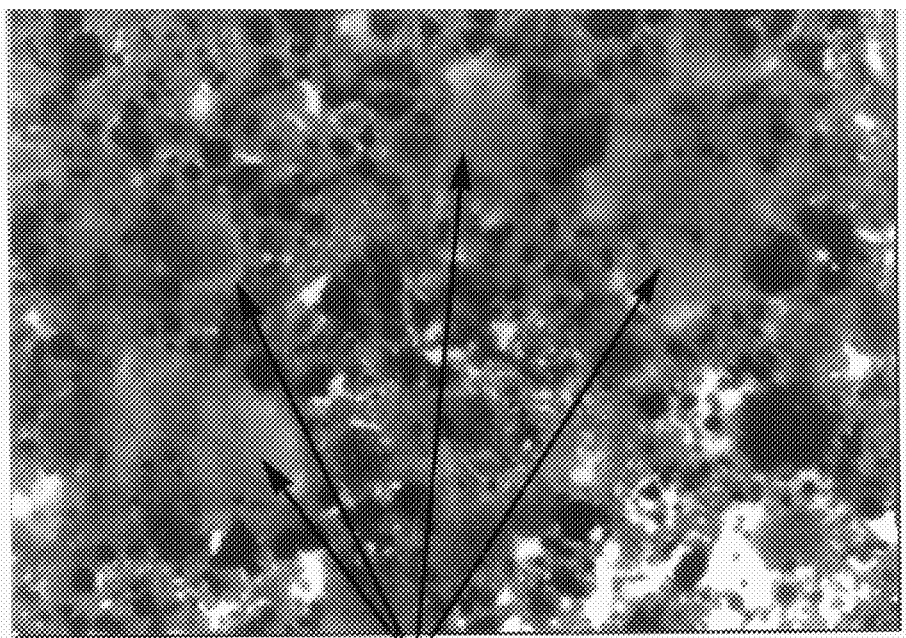
MNGC
MNGC
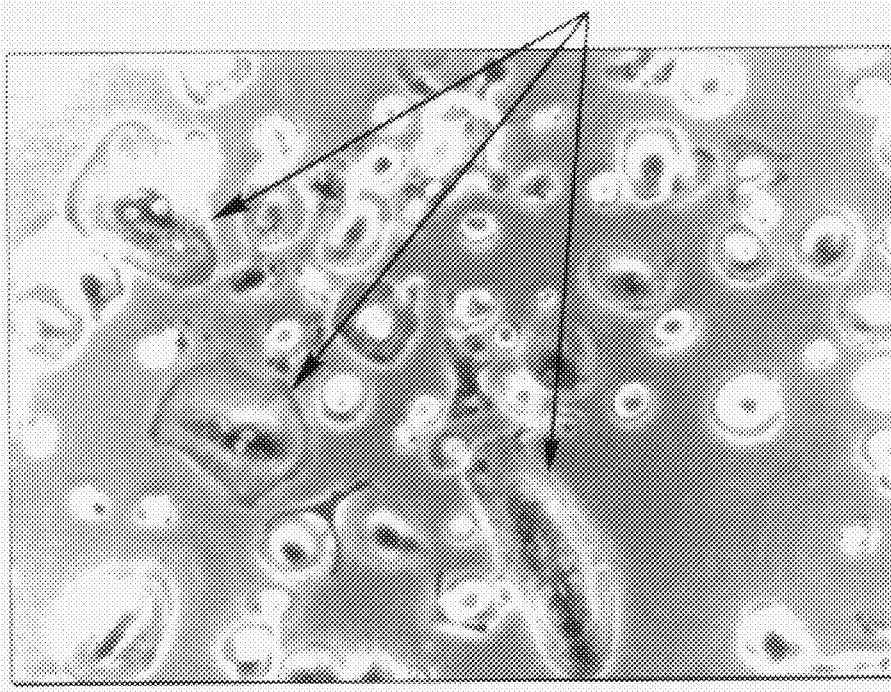
FIG. 4B

FIG. 4C
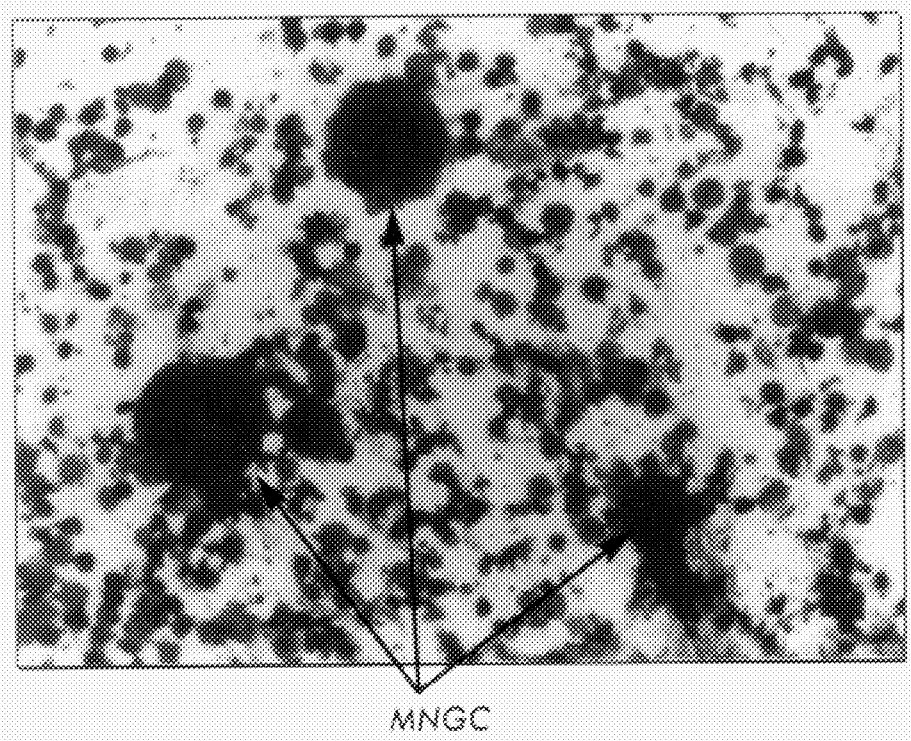
MNGC
MNGC
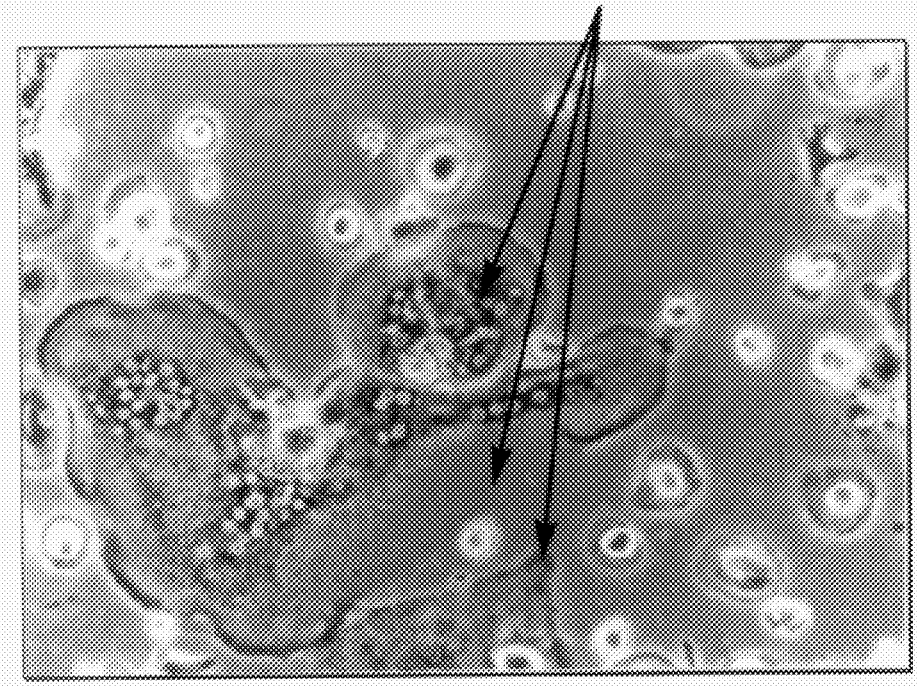
FIG. 4D

FIG. 4E
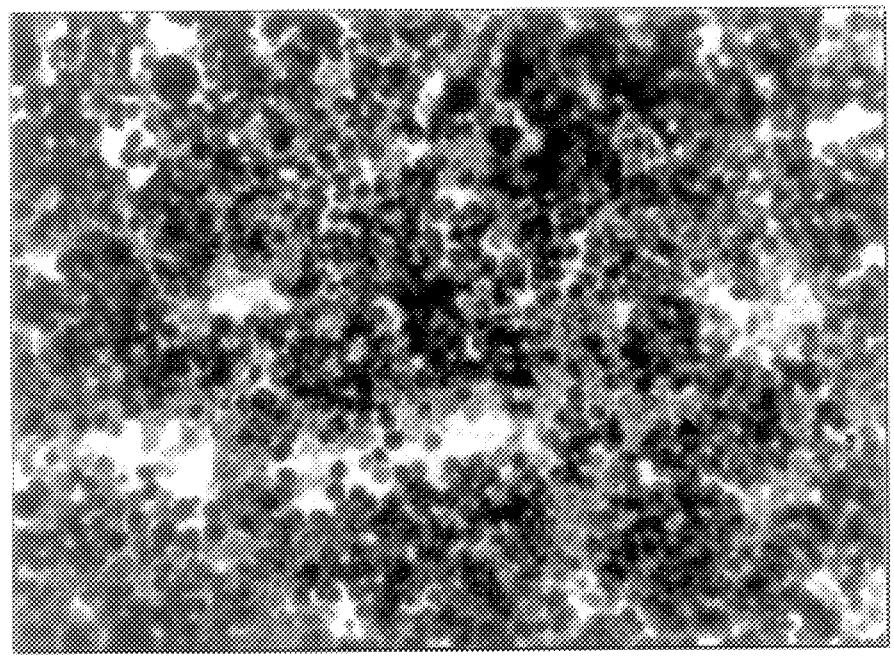
MNGC
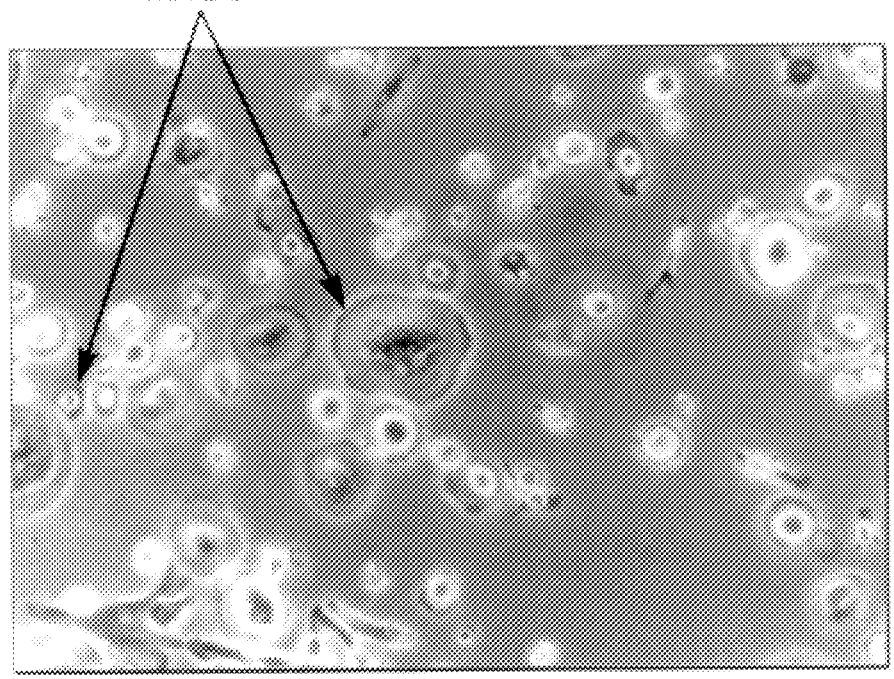
FIG. 4F

HIV-2 EXPRESSION VECTOR 40

HIV-2 EXPRESSION PLASMID 41

HIV-2 EXPRESSION PLASMID 42

HIV-2 EXPRESSION PLASMID 43

FIG. 10
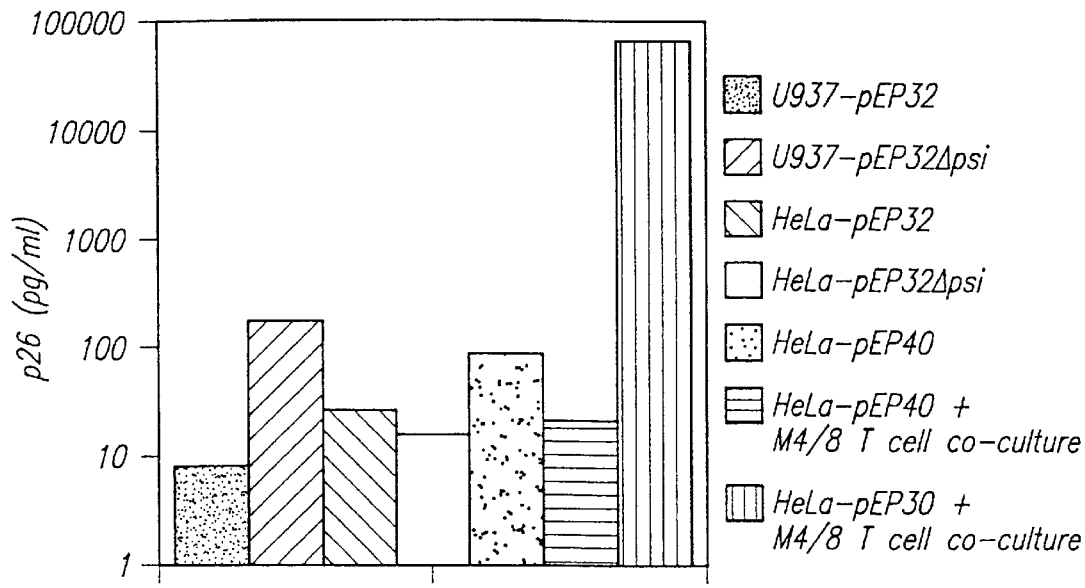
FIG. 11  G418 STABLE HIV-2 VIRAL PRODUCER & PACKAGING LINES: VIRAL ANTIGEN PRODUCTION
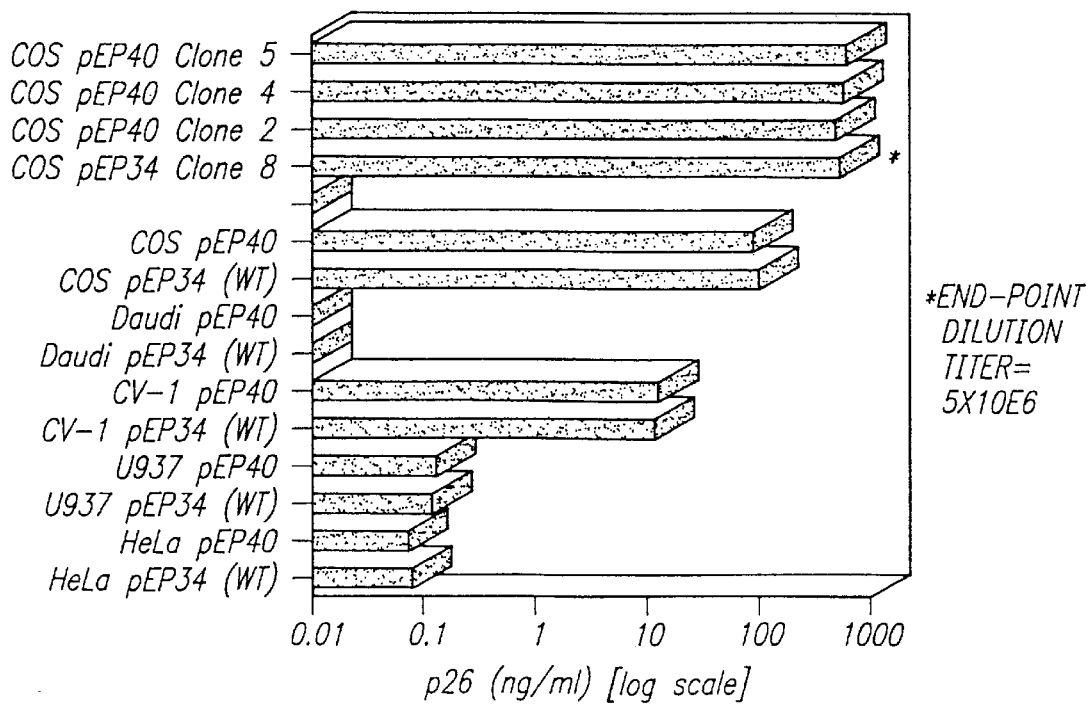

SEQUENCE LISTING ( 1 ) GENERAL INFORMATION:

( i i i ) NUMBER OF SEQUENCES: 50

( 2 ) INFORMATION FOR SEQ ID NO:1:

( i ) SEQUENCE CHARACTERISTICS:
        ( A ) LENGTH: 10163 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: -
        ( B ) LOCATION: 1..10163
        ( D ) OTHER INFORMATION: /note= "HIV-2KR provirus"

( x i ) SEQUENCE DESCRIPTION: SEQ ID NO:1:

```
TGGATGGGAT   GTATTACAGT   GAGAGAAGGA   CATAGAATCT   TAGACATATA   CATGGAAAAG        60

GAAGAAGGGA   TAATTCCAGA   TTGGCAGAAC   TATACTCATG   GGCCAGGAGT   AAGGTACCCA       120

AAGTTCTTTG   GGTGGCTATG   GAAGCTAGTA   CCAGTAGACG   TCCCACAAGG   TGAAGAGGAC       180

CACTGCTTAC   TACACCCAGC   ACAAACAAGC   GGGTCTGATG   ACCCTCATGG   GGAAACATTA       240

ATGTGGAGGT   TTGACCCTAG   GCTGGCCTAT   GAGTATACGG   CTTTTAATCG   ATACCCAGAA       300

GAATTTGGGT   ATAAGTCAGG   CCTGCCAGAA   GAAGAGTGGA   AGGCAAAACT   GAAAGCAAGA       360

GGGATACCAT   TTAGTTAAAG   ACAGGAACAG   CTATATTTGG   TCAGAACAGG   AAGTAGATGA       420

TGAAACTGCA   GGGACTTTCC   AGAAGGGGCT   GTAACCAGGG   GAGGGACGTG   GGAGGAACCG       480

GTGGGGAACG   CCCTCATACT   TCTGTATAAA   TGTACCCGCT   GCTTGCATTG   TATTCAGTCG       540

CTCTGCGGAG   AGGCTGGCAG   ATCGAGCCCT   GGGAGGTTCT   CTCCAGCACT   AGCAGGTAGA       600

GCCTGGGTGT   TCCCTGCTAG   ACTCTCACCA   GTACTTGGCC   GGTACTGGGC   AGACGGCTCC       660

ACGCTTGCTT   GCTTAAAGAC   CTCTTAATAA   AGCTGCCAGT   TAGAAGCAAG   TTAAGTGTGT       720

GTTCCCATCT   CTCCTAGTCG   CCGCCTGGTC   ATTCGGTGTT   CACCTAAGTG   ACAAGACCCT       780

GGTCTGTTAG   GACCCTTCTT   GCTTTGGGGA   ACCGAAGCGG   GAAAATACCT   AGCAGATTGG       840

CGCCCGAACA   GGACTTGAAG   GAGACTGGAA   CACGGCTGAG   TGAAGGCAGT   AAGGGCGGCA       900

GGAACAAACC   ACGACGGAGT   GCTCCTAGAA   AGGCGCGGGC   CGAGGTACCA   AAGGCGGCGT       960

GTGGAGCGGG   AGTAAAGAGG   CCTCCGGGTG   AAGGTAAGTA   CCTACACCAA   AAACTGTAGC      1020

CAGAAAAAGG   CTTGTTATCC   TACCTTTAGA   CAGGTAGAAG   ATTGTGGGAG   ATGGGCGCGA      1080

GAAGCTCCGT   CTTGAGAGGG   AAAAAAGTAG   ATGAATTAGA   AAAAATTAGG   TTACGGCCCG      1140

GCGGGAAGAA   AAAATATAGA   CTAAAGCATA   TTGTGTGGGC   AGCGAATGAA   TTGGGCAAAT      1200

TCGGATTGGC   AGAAAGCCTG   TTGGAGTCAA   AAGAAGGTTG   CCAAAAAATT   ATTACAGTTT      1260

TAGATCCATT   AGTGCCAACA   GGATCAGAAA   ATTTAAAAAG   CCTTTTTAAT   ACTGTCTGCG      1320

TCATTTGGTG   CTTGCACGCA   GAAGAGAAAG   TGAAAGATAC   TGAAGGAGCA   AAACAAATAG      1380
```

```
TACAGAGACA  TCTAGTGGCA  GAAACAGGAA  CTGCAGACAA  AATGCCAAGC  ACAAGTAGAC   1440

CAGCAGCACC  ACCTAGCGGG  AGAGGGGGAA  ATTACCCCGT  GCAACAAATA  GCTGGCAACT   1500

ATTCCCATGT  GCCGTTGAGC  CCCCGAACCC  TAAATGCTTG  GGTAAAGTTA  GTGGAAGAAA   1560

AGAAGTTCGG  GGCAGAAGTA  GTGCCAGGGT  TTCAGGCACT  CTCAGAAGGC  TGCACGCCCT   1620

ATGATATTAA  TCAAATGCTT  AATTGTGTGG  GCGACCATCA  AGCAGCTATG  CAAATAATCA   1680

GAGAGATTAT  TAATGAAGAA  GCAGCAGATT  GGGATGTGCA  ACACCCAATA  CCAGGCCCCT   1740

TGCCAGCGGG  GCAGCTTAGA  GAACCAAGAG  GGTCTGATAT  AGCAGGGACA  ACAAGCACAG   1800

TAGAAGAACA  GATCCAGTGG  ATGTTTAGAG  CACAAAATCC  TATACCAGTA  GGGAACATCT   1860

ATAGGAGATG  GATCCAGATA  GGACTGCAGA  AGTGCGTCAG  GATGTACAAT  CCAACCAACA   1920

TCCTAGACGT  AAAACAGGGA  CCAAGGAGC   CGTTCCAAAG  CTATGTAGAT  AGATTCTACA   1980

AAAGCCTAAG  GGCAGAACAA  ACAGACCCAG  CAGTAAAAAA  TTGGATGACC  CAAACACTGC   2040

TGGTACAGAA  TGCCAACCCA  GACTGTAAAT  TAGTACTAAA  AGGACTGGGG  ATGAATCCTA   2100

CCTTAGAGGA  GATGCTGACC  GCCTGTCAGG  GAATAGGAGG  ACCAGGCCAG  AAAGCCAGAT   2160

TAATGGCAGA  AGCCTTAAAG  GAGGCCCTAG  CACCAGCCCC  TATCCCATTT  GCAGCAGCCC   2220

AACAGAGAAG  GACAATTAAG  TGCTGGAATT  GTGGAAAGGA  TGGGCACTCG  GCAAGACAAT   2280

GCCGAGCACC  TAGAAGACAG  GGCTGCTGGA  AATGTGGCAA  ATCAGGACAT  GTCATGGCAA   2340

ACTGCCCAGA  AAGACAGGCT  GGTTTTTTAG  GGATTGGCCC  ATGGGGAAAG  AAGCCTCGCA   2400

ACTTCCCCGT  GACCCGAGTC  CCGCAGGGGC  TGACACCAAC  AGCACCCCCA  GCAGACCCAG   2460

CAGCAGACCT  GCTAGAGAAG  TACTTGCAGC  AAGGGAGGAA  GCAGAAAGAG  CAGAAAATGA   2520

GACCATACAA  GGAGGTGACA  GAGGACTTAC  TGCACCTCGA  ACAAGGAGAG  ACACCACACA   2580

AAGAGGCGAC  AGAGGATTTG  CTGCACCTCA  ATTCTCTCTT  TGGAAAAGAC  CAGTAGTCAC   2640

AGCATATGTT  GAGGGTCAGC  CAGTAGAAGT  CTTACTAGAC  ACAGGGGCTG  ACGACTCAAT   2700

AGTAGCAGGA  ATAGAGTTGG  GGAGCAATTA  TAGTCCAAAA  ATAGTAGGGG  AATAGGGGG    2760

ATTCATAAAC  ACCAAGGAAT  ATAAAAATGT  AGAAATAAAA  GTACTAAATA  AAAAGGTAAA   2820

AGCCACCATA  ATGACAGGTG  ATACCCCAAT  CAACATTTTT  GGCAGAAACA  TTCTGACAGC   2880

CTTAGGCATG  TCATTAAATC  TACCAGTCGC  CAAGGTAGAC  CCGATAAAAG  TAATACTGAA   2940

ACCAGGAAAA  GATGGACCAA  AAGTAAGACA  ATGGCCTCTA  ACAAAAGAAA  AGATAGAGGC   3000

ACTAAAAGAA  ATCTGTGAAA  AAATGGAAAG  AGAAGGCCAG  CTAGAGGAAG  CTCCCCCAAC   3060

TAATCCTTAT  AATACCCCCA  CATTTGCAAT  TAAGAAAAAG  GACAAAAACA  AATGGAGAAT   3120

GCTAATAGAT  TTTAGAGAAC  TAAATAAGGT  AACTCAAGAG  TTCACAGAAA  TTCAGTTAGG   3180

AATTCCACAC  CCAGCAGGAT  TAGCCAAGAA  AAGAAGAATT  ACTGTACTAG  ATATAGGGGA   3240

TGCCTACTTT  TCCATACCAC  TACATGAGGA  CTTTAGACAA  TATACTGCAT  TTACTCTACC   3300

AACAGTGAAC  AATGCAGAAC  CAGGAAAGAG  ATATATATAT  AAAGTCCTAC  CACAGGGATG   3360

GAAAGGATCG  CCAGCAATTT  TTCAACACAC  AATGAGGCAG  GTCTTAGAGC  CATTCAGAAA   3420

AGCAAACCCA  GACGTCATTC  TCGTCCAATA  TATGGATGAT  ATCTTAATAG  CTAGCGACAG   3480

GACAGACTTA  GAGCATGACA  GAACGGTCCT  GCAGTTAAAA  GAACTTTTAA  ATGGCCTAGG   3540

ATTCTCCACC  CCAGATGAGA  AGTTCCAAAA  AGACCCCCCA  TACAAATGGA  TGGGCTATGA   3600

ACTATGGCCA  ACCAAATGGA  AGCTGCAAAA  AATACAATTG  CCCCAAAAAG  AAGTATGGAC   3660

AGTCAATGAC  ATCCAAAAGC  TAGTAGGTGT  CCTAAATTGG  GCAGCACAAA  TCTACCCAGG   3720

GATAAAGACC  AAACACTTAT  GTAGGCTAAT  TAGAGGAAAA  ATGACACTCA  CGGAAGAAGT   3780
```

```
ACAGTGGACA  GAACTAGCAG  AGGCAGAACT  AGAAGAGAAC  AAAATTATCT  TGAGCCAGGA    3840
ACAGGAGGGA  TGCTATTACC  AAGAAGAAAA  GGAATTAGAA  GCAACAGTCC  AAAAGGATCA    3900
AGACAATCAG  TGGACATATA  AAATACACCA  AGGAGAGAAA  ATCCTAAAAG  TAGGAAAATA    3960
TGCAAAGATA  AAAAATACCC  ATACCAATGG  GGTCAGATTG  TTAGCACATG  TAGTTCAAAA    4020
AATAGGAAAA  GAAGCACTAG  TCATTTGGGG  ACGAATACCA  AAATTTCACC  TACCAGTAGA    4080
AAGAGAAACC  TGGGAGCAGT  GGTGGGATAA  CTATTGGCAA  GTGACATGGA  TCCCAGACTG    4140
GGACTTCGTA  TCTACTCCAC  CACTGGTCAG  GTTAGCATTT  AACCTAGTAA  AGATCCCAT     4200
ACCAGGTGAA  GAGACCTTCT  ACACAGATGG  ATCCTGTAAT  AGGCAATCAA  AGAGGGAAA     4260
AGCAGGATAT  ATAACAGATA  GAGGGAGAGA  CAAGGTAAGG  ATATTGGAGC  AAACTACCA     4320
TCAGCAAGCA  GAATTAGAAG  CCTTCGCAAT  GGCATTAACA  GACTCAGGTC  AAAAGCCAA     4380
TATTATAGTA  GACTCACAGT  ATGTAATGGG  AATAGTAGCG  GGCCAGCCAA  CAGAATCAGA    4440
GAGTAAACTA  GTAAACCAAA  TCATAGAAGA  AATGATAAAA  AAGGAAACAC  TCTATGTTGC    4500
ATGGGTCCCA  GCCCACAAAG  GCATAGGAGG  AAATCAGGAA  GTAGATCATT  TAGTAAGTCA    4560
GGGCATTAGA  CAAGTATTAT  TCCTAGAAAA  AATAGAGCCC  GCTCAGGAAG  AACATGAGAA    4620
ATATCATAGC  AATGTAAAAG  AATTATCCCA  TAAATTTGGA  CTGCCCAAAC  TAGTGGCAAG    4680
ACAAATAGTA  AACACATGTG  CCCAATGTCA  ACAGAAAGGG  GAAGCTATAC  ATGGGCAAGT    4740
AGATGCAGAA  CTGGGCACTT  GGCAAATGGA  CTGCACACAC  TTAGAGGGAA  AAATCATTAT    4800
AGTAGCAGTA  CATGTTGCAA  GCGGGTTTAT  AGAAGCAGAA  GTTATCCCAC  AGGAAACGGG    4860
AAGGCAAACA  GCACTCTTCC  TATTAAAACT  GGCCAGTAGG  TGGCCAATAA  CACACCTGCA    4920
CACAGATAAT  GGTGCCAACT  TCACCTCACA  GGAAGTAAAG  ATGGTAGCGT  GGTGGACAGG    4980
TATAGAACAA  TCCTTTGGAG  TACCTTACAA  TCCACAAAGC  CAAGGAGTAG  TAGAAGCAAT    5040
GAATCACCAC  TTAAAAAACC  AGATAAGCAG  AATTAGAGAG  CAGGCAAATA  CAATGGAAAC    5100
AATAGTATTA  ATGGCAGTTC  ATTGCATGAA  TTTTAAAAGA  AGGGGAGGAA  TAGGGGATAT    5160
GACCCCAGCA  GAAAGACTAA  TCAATATGAT  CACCACAGAA  CAAGAAATAC  AATTCCTCCA    5220
CGCAAAAAAT  TCAAAATTAA  AAAATTTCCG  GGTCTATTTC  AGAGAAGGCA  GAGATCAGCT    5280
GTGGAAAGGA  CCTGGGGAAC  TACTGTGGAA  GGGAGATGGA  GCAGTCATAG  TCAAGGTAGG    5340
GACAGACATA  AAAATAGTGC  CAAGAAGGAA  AGCTAAGATC  ATCAGAGACT  ATGGAGGAAG    5400
GCGAGAGGTG  GATAGTAGTT  CCCACTTGGA  GGGTACCAGG  GAGGATGGAG  AAGTGGCATA    5460
GCCTTGTCAA  GTATCTAAAA  CACAGAACAA  AAGATCTGGA  AGGGGTGTGC  TATGTTCCCC    5520
ACCATAAGGT  GGGATGGGCA  TGGTGGACTT  GCAGCAGGGT  AATATTCCCA  TTACAAGGAA    5580
ATAGTCACCT  AGAGATACAG  GCATATTGGA  ACCTAACACC  AGAAAAGGA   TGGCTCTCCT    5640
CTTATGCAGT  AAGAATAACC  TGGTATACAG  AGAGGTTCTG  GACAGATGTT  ACCCCAGACT    5700
GTGCAGACTC  CCTAATACAT  AGCACTTATT  TCTCTTGTTT  TACGGCGGGT  GAAGTAAGAA    5760
GAGCCATCAG  AGGGGAAAAG  TTACTGTCCT  GCTGCAATTA  CCCCCAAGCC  CATAGATCTA    5820
AGGTACCGTT  ACTCCAATTT  CTGGCCTTAG  TAGTAGTGCA  ACAAAATGGC  AGACCCCAGA    5880
AAAACAGTAC  CACCAGGAAA  CGGTGGCGAA  GTAACTATTG  GAGAGGCTTT  CGCTTGGCTA    5940
GAAAGGATGG  TAGAGGCCAT  AAACAGAGAG  GCAGTGAACC  ACCTGCCTCG  GGAGCTTATT    6000
TTCCAGGTGT  GGCAAAGGTC  CTGGAGATAC  TGGCATGATG  ACCTAGGGAT  GTCACAAAGT    6060
TACACAAAGT  ATAGATATTT  GCGCTTAATG  CAGTATGCTA  TGTTCATACA  TGTTAAGAAA    6120
GGGTGCACTT  GCCTGGGGGG  AGGACATGGG  CCGGGAGGGT  GGAGACCAGG  ACCTCCCCCT    6180
```

```
CCTCCCCCAG GCCTAGTCTA ATGACTGAAG CACCAGCAGA GTTTCCCCCG GAGGATGAAA    6240
CCCCACCGAG GGGGCCAGGG GATGAGTGGG TAATAGGAAT CCTGAGAGAA TTAAGAGAAG    6300
AAGCTTTAAA GCATTTGAC  CCTCGCTTGC TAACTACTCT TGGCAACTAT ATCTGTGCTA    6360
GACATGGAGA CACCCTCGAA AGCGCCAGAG AGCTCATTAA TGTCCTGCAA CGAGCCCTCT    6420
TCGTGCACTT CAGAGCAGGA TGTAAAATCT CAAGAATTGG CCAAACAAGG GGAGAGACTC    6480
CTTTCTCAGC TATACCAACC CCTAGAGGCA TGCAATAACC CATGTTATTG TAAGAAATGT    6540
TGTTACCATT GCCAGCTATG TTTTTAAAA  AAGGGACTCG GGATATGTTA TGAACGGAAG    6600
GGCAGACGAA GAAGGACTCC AAGGGCTCAT TCGTCTTCTG CATCAGACAA GTGAGTATAA    6660
TGGATAGTAG AAATCAGCTA ATTGTTGCCA TTTTACTAAC TAGTGCTTGC TTAATATATT    6720
GCGCCCAATA TGTGACTGTT TTCTATGGCA TACCCGCGTG GAAGAATGCA TCCATTCCCC    6780
TCTTTTGTGC AACCAGAAAT AGAGATACTT GGGGAACCAT ACAGTGCTTG CCAGACAATG    6840
ATGATTATCA GGAAATACCT TTAAATGTGA CAGAGGCTTT TGACGCATGG AACAATACAG    6900
TAACAGAACA AGCAGTAGAA GATGTCTGGA ATCTATTTGA GACATCAGTA AAACCATGTG    6960
TCAAATTAAC ACCCTTATGT GTGCAAATGG AATGTAACAG CACAAGTACA GAGAGCAGTA    7020
ACAGCACAAG TGAGGGGAGC ACAGTCCCAG AGATATTAAA CGAAACTACT TCATGCATAA    7080
CCAACAACAG CTGCTCAGAT TTAGGGAGTG AAGAGGTAGT CGATTGTCGG TTCAATATGA    7140
CAGGACTACA ACTAGATAAG CCACAGCAAT ATAGTGAAAC ATGGTACTCA AAGGATGTAG    7200
TTTGTGACAC AACTAATGGG ACCAGCCGCA AATGTTACAT GAACCATTGC AACACATCAG    7260
TCATCACAGA GTCATGTGAT AAGCACTATT GGGATGCTAT GAGGTTTAGA TACTGTGCAC    7320
CACCGGGTTT ATGCTTGCTA AGATGCAATG ATACCAATTA TTCAGGCTTT GAGCCCAAGT    7380
GTCCTAAAGT AGTAGCTGCT ACATGCACAA GAATGATGGA AACGCAAACT TCTACTTGGT    7440
TTGGCTTTAA TGGCACTAGG GCAGAAAATA GAACATATAT CTATTGGCAT GGTAGAGATA    7500
ATAGGACTAT TATCAGCTTA AATACACATT ATAATCTCAC AATGCATTGT AAGAGGCCAG    7560
GAAATAAGTC AGTTTTGCCA ATAACACTTA GGTCAGGGAG AGTGTTTCAC TCCCGACCGA    7620
TCATCAATGA AAGACCCAAG CAGGCATGGT GCTGGTTCGG AGGTGATTGG AAGAAAGCCA    7680
TGCAGGAGGT GAAACAAACC CTTGTGAAAC ATCCCAGGTA TAGAGGAACC AACGACACAC    7740
AGAAAATTAA CTTTACACAA CCAGGAAAAG GTTCAGATGC AGAAGTGGTA TACATGTGGA    7800
CTAACTGCAG AGGAGAATTT CTATACTGCA ACATGACTCG GTTCCTCAAT TGGATAGAAA    7860
ACAGGGCACA CCCACAGCGC AATTATGCAC CGTGCCATAT AAGGCAAATA ATTAATACCT    7920
GGCATAGAGT AGGCCAAAAT ATATATTTGC CTCCTAGGGA AGGGGAATTG GTCTGCAACT    7980
CAACAGTAAC CAGCATAATT GCTAACATTG ACATGTTTGA TAACCAGACA AGCATTACCT    8040
TTAGTGCAGA GGTGGCAGAA CTATACCGAT GGAATTGGG  AGATTACAAA TTAGTAGAAA    8100
TAACACCAAT TGGCTTCGCA CCTACATCAG AAAAAAGGTA TTCCTCTGCT CCACAGAGGA    8160
ATAAAGAGG  TGTGTTTGTG CTAGGAGTCT TGGGTTTTCT CGCAACAGCA GGTTCTGCAA    8220
TGGGCGCGGC GTCCTTGACG CTGTCGGCTC ATCCCGGACT TTACTGGGCT GGGATAGTGC    8280
AGCAACAGCA ACAGCTGTTG GACGTGGTCA AGAGACAACA AGAAATGTTG CGACTGACCG    8340
TCTGGGGAAC AAAAAATCTC CAGACAAGAG TCACTGCTAT CGAGAAATAC CTAAGGGACC    8400
AGGCGCGGCT AAATTCATGG GGATGTGCAT TTAGACAAGT CTGCTACACC ACTGTACTAT    8460
GGGAAAATAA CAGCATAGTA CCTGATTGGA ACAACATGAC GTGGCAGGAA TGGGAACAAC    8520
AAACCCGCGA CCTAGAGGCA AATATCAGTA GATCGTTAGA GCAGGCACAA ATCCAACAAG    8580
```

-continued

```
AGAAAAATAT GTATGAGCTA CAAAAATTAA ATAGCTGGGA TGTTTTTGGC AACTGGTTTG      8640

ATTTAACCTC CTGGATTAAG TATATTCAGT ATGGAGTTTA TGTAATAATA GGAATAATAG      8700

CTTTAAGAAT AGTAATATAT GTAGTACAAT TACTAAGTAG ACTTAGAAAG GGCTATAGGC      8760

CTGTTTTCTC TTCCCCCCCC GGTTATATCC AACAGATCCA TATCCACAAG GACTGGGAAC      8820

AGCCAGACAG AGAAGAAACA GACGAAGACG CCGGAAACAG CATTGGAGAC AGCTCGTGGC      8880

CTTGGCCAAT AGCATATATA CATTTCCTGA TCCGCCAGCT GATTCGCCTC TTGACCGGGC      8940

TATACAGCGT CTGCAAGGAC TTACTATCCA GGAGCTTCCC GACCCTCCAA CTAATCTTCC      9000

AGAGTCTTCA GAGAGCACTA ACAACAATCA GGGACTGGCT GAGACTTACA ATAGCCTACC      9060

TGCAATATGG GTGCGAGTGG ATCCAAGAAG TGCTCCAGGT CCTTGCAAGG ACTACGAGAG      9120

AGACTCTTGC GAGCGCGTGG AGAGACTTGT GGGGGGCAAT GGGACGGATC GGCAGGGGAA      9180

TACTTGCAGT TCCAAGAAGG ATCAGGCAGG GGGCAGAACT TGCCCTCCTG TGAGGGGCAG      9240

CGGTATCAAC AGGGAGACTT TATGAACACC CCATGGAGAA CTCCAGCAGC AGGAAGGGAG      9300

GGAACATTGT ACAAGCAACA AAATATGGAT GATGTAGATG CAGATAATGA TAACCTAATA      9360

GGGGTCCCTG TCACACCAAG AGTACCATTA AGGGCAATGA CATATAAGTT GGCAGTAGAT      9420

ATATCACATT TTCTAAATGA AAAGGGGGGA CTGGATGGGA TGTATTACAG TGAGAGAAGA      9480

CATAGAATCT TAGACATATA CATGGAAAAG GAAGAAGGGA TAATTCCAGA TTGGCAGAAC      9540

TATACTCATG GGCCAGGAGT AAGGTACCCA AAGTTCTTTG GGTGGCTATG GAAGCTAGTA      9600

CCAGTAGACG TCCCACAAGG TGAAGAGGAC CACTGCTTAC TACACCCAGC ACAAACAAGC      9660

GGGTCTGATG ACCCTCATGG GGAAACATTA ATGTGGAGGT TTGACCCTAG GCTGGCCTAT      9720

GAGTATACGG CTTTTAATCG ATACCCAGAA GAATTTGGGT ATAAGTCAGG CCTGCCAGAA      9780

GAAGAGTGGA AGGCAAAACT GAAAGCAAGA GGGATACCAT TTAGTTAAAG ACAGGAACAG      9840

CTATATTTGG TCAGAACAGG AAGTAGATGA TGAAACTGCA GGGACTTTCC AGAAGGGGCT      9900

GTAACCAGGG GAGGGACGTG GGAGGAACCG GTGGGGAACG CCCTCATACT TCTGTATAAA      9960

TGTACCCGCT GCTTGCATTG TATTCAGTCG CTCTGCGGAG AGGCTGGCAG ATCGAGCCCT     10020

GGGAGGTTCT CTCCAGCACT AGCAGGTAGA GCCTGGGTGT TCCCTGCTAG ACTCTCACCA     10080

GTACTTGGCC GGTACTGGGC AGACGGCTCC ACGCTTGCTT GCTTAAAGAC CTCTTAATAA     10140

AGCTGCCAGT TAGAAGCAAG TTA                                            10163
```

( 2 ) INFORMATION FOR SEQ ID NO:2:

( i ) SEQUENCE CHARACTERISTICS:
        ( A ) LENGTH: 857 amino acids
        ( B ) TYPE: amino acid
        ( C ) STRANDEDNESS:
        ( D ) TOPOLOGY: linear ( i i ) MOLECULE TYPE: protein ( i x ) FEATURE:
        ( A ) NAME/KEY: Protein
        ( B ) LOCATION: 1..857
        ( D ) OTHER INFORMATION: /note= "env protein encoded by HIV-2KR"

( x i ) SEQUENCE DESCRIPTION: SEQ ID NO:2:

```
Met  Asp  Ser  Arg  Asn  Gln  Leu  Ile  Val  Ala  Ile  Leu  Leu  Thr  Ser  Ala
  1              5                   10                      15

Cys  Leu  Ile  Tyr  Cys  Ala  Gln  Tyr  Val  Thr  Val  Phe  Tyr  Gly  Ile  Pro
             20                   25                      30

Ala  Trp  Lys  Asn  Ala  Ser  Ile  Pro  Leu  Phe  Cys  Ala  Thr  Arg  Asn  Arg
```

|  |  | 35 |  |  |  |  | 40 |  |  |  |  | 45 |  |  |
|---|---|---|---|---|---|---|---|---|---|---|---|---|---|---|
| Asp | Thr | Trp | Gly | Thr | Ile | Gln | Cys | Leu | Pro | Asp | Asn | Asp | Asp | Tyr | Gln |
|  | 50 |  |  |  |  | 55 |  |  |  |  | 60 |  |  |  |  |
| Glu | Ile | Pro | Leu | Asn | Val | Thr | Glu | Ala | Phe | Asp | Ala | Trp | Asn | Asn | Thr |
| 65 |  |  |  |  | 70 |  |  |  |  | 75 |  |  |  |  | 80 |
| Val | Thr | Glu | Gln | Ala | Val | Glu | Asp | Val | Trp | Asn | Leu | Phe | Glu | Thr | Ser |
|  |  |  |  | 85 |  |  |  |  | 90 |  |  |  |  | 95 |  |
| Val | Lys | Pro | Cys | Val | Lys | Leu | Thr | Pro | Leu | Cys | Val | Gln | Met | Glu | Cys |
|  |  |  | 100 |  |  |  | 105 |  |  |  |  | 110 |  |  |  |
| Asn | Ser | Thr | Ser | Thr | Glu | Ser | Ser | Asn | Ser | Thr | Ser | Glu | Gly | Ser | Thr |
|  |  | 115 |  |  |  |  | 120 |  |  |  |  | 125 |  |  |  |
| Val | Pro | Glu | Ile | Leu | Asn | Glu | Thr | Thr | Ser | Cys | Ile | Thr | Asn | Asn | Ser |
|  | 130 |  |  |  |  | 135 |  |  |  |  | 140 |  |  |  |  |
| Cys | Ser | Asp | Leu | Gly | Ser | Glu | Glu | Val | Val | Asp | Cys | Arg | Phe | Asn | Met |
| 145 |  |  |  |  | 150 |  |  |  |  | 155 |  |  |  |  | 160 |
| Thr | Gly | Leu | Gln | Leu | Asp | Lys | Pro | Gln | Gln | Tyr | Ser | Glu | Thr | Trp | Tyr |
|  |  |  |  | 165 |  |  |  |  | 170 |  |  |  |  | 175 |  |
| Ser | Lys | Asp | Val | Val | Cys | Asp | Thr | Thr | Asn | Gly | Thr | Ser | Arg | Lys | Cys |
|  |  |  | 180 |  |  |  |  | 185 |  |  |  |  | 190 |  |  |
| Tyr | Met | Asn | His | Cys | Asn | Thr | Ser | Val | Ile | Thr | Glu | Ser | Cys | Asp | Lys |
|  |  | 195 |  |  |  |  | 200 |  |  |  |  | 205 |  |  |  |
| His | Tyr | Trp | Asp | Ala | Met | Arg | Phe | Arg | Tyr | Cys | Ala | Pro | Pro | Gly | Leu |
|  | 210 |  |  |  |  | 215 |  |  |  |  | 220 |  |  |  |  |
| Cys | Leu | Leu | Arg | Cys | Asn | Asp | Thr | Asn | Tyr | Ser | Gly | Phe | Glu | Pro | Lys |
| 225 |  |  |  |  | 230 |  |  |  |  | 235 |  |  |  |  | 240 |
| Cys | Pro | Lys | Val | Val | Ala | Ala | Thr | Cys | Thr | Arg | Met | Met | Glu | Thr | Gln |
|  |  |  |  | 245 |  |  |  |  | 250 |  |  |  |  | 255 |  |
| Thr | Ser | Thr | Trp | Phe | Gly | Phe | Asn | Gly | Thr | Arg | Ala | Glu | Asn | Arg | Thr |
|  |  |  | 260 |  |  |  |  | 265 |  |  |  |  | 270 |  |  |
| Tyr | Ile | Tyr | Trp | His | Gly | Arg | Asp | Asn | Arg | Thr | Ile | Ile | Ser | Leu | Asn |
|  |  |  | 275 |  |  |  |  | 280 |  |  |  |  | 285 |  |  |
| Thr | His | Tyr | Asn | Leu | Thr | Met | His | Cys | Lys | Arg | Pro | Gly | Asn | Lys | Ser |
|  | 290 |  |  |  |  | 295 |  |  |  |  | 300 |  |  |  |  |
| Val | Leu | Pro | Ile | Thr | Leu | Arg | Ser | Gly | Arg | Val | Phe | His | Ser | Arg | Pro |
| 305 |  |  |  |  | 310 |  |  |  |  | 315 |  |  |  |  | 320 |
| Ile | Ile | Asn | Glu | Arg | Pro | Lys | Gln | Ala | Trp | Cys | Trp | Phe | Gly | Gly | Asp |
|  |  |  |  | 325 |  |  |  |  | 330 |  |  |  |  | 335 |  |
| Trp | Lys | Lys | Ala | Met | Gln | Glu | Val | Lys | Gln | Thr | Leu | Val | Lys | His | Pro |
|  |  |  | 340 |  |  |  |  | 345 |  |  |  |  | 350 |  |  |
| Arg | Tyr | Arg | Gly | Thr | Asn | Asp | Thr | Gln | Lys | Ile | Asn | Phe | Thr | Gln | Pro |
|  |  | 355 |  |  |  |  | 360 |  |  |  |  | 365 |  |  |  |
| Gly | Lys | Gly | Ser | Asp | Ala | Glu | Val | Val | Tyr | Met | Trp | Thr | Asn | Cys | Arg |
|  | 370 |  |  |  |  | 375 |  |  |  |  | 380 |  |  |  |  |
| Gly | Glu | Phe | Leu | Tyr | Cys | Asn | Met | Thr | Arg | Phe | Leu | Asn | Trp | Ile | Glu |
| 385 |  |  |  |  | 390 |  |  |  |  | 395 |  |  |  |  | 400 |
| Asn | Arg | Ala | His | Pro | Gln | Arg | Asn | Tyr | Ala | Pro | Cys | His | Ile | Arg | Gln |
|  |  |  |  | 405 |  |  |  |  | 410 |  |  |  |  | 415 |  |
| Ile | Ile | Asn | Thr | Trp | His | Arg | Val | Gly | Gln | Asn | Ile | Tyr | Leu | Pro | Pro |
|  |  |  | 420 |  |  |  |  | 425 |  |  |  |  | 430 |  |  |
| Arg | Glu | Gly | Glu | Leu | Val | Cys | Asn | Ser | Thr | Val | Thr | Ser | Ile | Ile | Ala |
|  |  | 435 |  |  |  |  | 440 |  |  |  |  | 445 |  |  |  |
| Asn | Ile | Asp | Met | Phe | Asp | Asn | Gln | Thr | Ser | Ile | Thr | Phe | Ser | Ala | Glu |
| 450 |  |  |  |  | 455 |  |  |  |  | 460 |  |  |  |  |  |

-continued

```
Val Ala Glu Leu Tyr Arg Leu Glu Leu Gly Asp Tyr Lys Leu Val Glu
465                 470                 475                 480

Ile Thr Pro Ile Gly Phe Ala Pro Thr Ser Glu Lys Arg Tyr Ser Ser
                485                 490                 495

Ala Pro Gln Arg Asn Lys Arg Gly Val Phe Val Leu Gly Val Leu Gly
            500                 505                 510

Phe Leu Ala Thr Ala Gly Ser Ala Met Gly Ala Ala Ser Leu Thr Leu
        515                 520                 525

Ser Ala His Pro Gly Leu Tyr Trp Ala Gly Ile Val Gln Gln Gln Gln
    530                 535                 540

Gln Leu Leu Asp Val Val Lys Arg Gln Gln Glu Met Leu Arg Leu Thr
545                 550                 555                 560

Val Trp Gly Thr Lys Asn Leu Gln Thr Arg Val Thr Ala Ile Glu Lys
                565                 570                 575

Tyr Leu Arg Asp Gln Ala Arg Leu Asn Ser Trp Gly Cys Ala Phe Arg
            580                 585                 590

Gln Val Cys Tyr Thr Thr Val Leu Trp Glu Asn Asn Ser Ile Val Pro
        595                 600                 605

Asp Trp Asn Asn Met Thr Trp Gln Glu Trp Glu Gln Gln Thr Arg Asp
    610                 615                 620

Leu Glu Ala Asn Ile Ser Arg Ser Leu Glu Gln Ala Gln Ile Gln Gln
625                 630                 635                 640

Glu Lys Asn Met Tyr Glu Leu Gln Lys Leu Asn Ser Trp Asp Val Phe
                645                 650                 655

Gly Asn Trp Phe Asp Leu Thr Ser Trp Ile Lys Tyr Ile Gln Tyr Gly
            660                 665                 670

Val Tyr Val Ile Ile Gly Ile Ile Ala Leu Arg Ile Val Ile Tyr Val
        675                 680                 685

Val Gln Leu Leu Ser Arg Leu Arg Lys Gly Tyr Arg Pro Val Phe Ser
    690                 695                 700

Ser Pro Pro Gly Tyr Ile Gln Gln Ile His Ile His Lys Asp Trp Glu
705                 710                 715                 720

Gln Pro Asp Arg Glu Glu Thr Asp Glu Asp Ala Gly Asn Ser Ile Gly
                725                 730                 735

Asp Ser Ser Trp Pro Trp Pro Ile Ala Tyr Ile His Phe Leu Ile Arg
            740                 745                 750

Gln Leu Ile Arg Leu Leu Thr Gly Leu Tyr Ser Val Cys Lys Asp Leu
        755                 760                 765

Leu Ser Arg Ser Phe Pro Thr Leu Gln Leu Ile Phe Gln Ser Leu Gln
    770                 775                 780

Arg Ala Leu Thr Thr Ile Arg Asp Trp Leu Arg Leu Thr Ile Ala Tyr
785                 790                 795                 800

Leu Gln Tyr Gly Cys Glu Trp Ile Gln Glu Val Leu Gln Val Leu Ala
                805                 810                 815

Arg Thr Thr Arg Glu Thr Leu Ala Ser Ala Trp Arg Asp Leu Trp Gly
            820                 825                 830

Ala Met Gly Arg Ile Gly Arg Gly Ile Leu Ala Val Pro Arg Arg Ile
        835                 840                 845

Arg Gln Gly Ala Glu Leu Ala Leu Leu
    850                 855
```

( 2 ) INFORMATION FOR SEQ ID NO:3:

( i ) SEQUENCE CHARACTERISTICS:
        ( A ) LENGTH: 521 amino acids ( B ) TYPE: amino acid
( C ) STRANDEDNESS:
( D ) TOPOLOGY: linear ( i i ) MOLECULE TYPE: protein ( i x ) FEATURE:
( A ) NAME/KEY: Protein
( B ) LOCATION: 1..521
( D ) OTHER INFORMATION: /note= "gag protein encoded by HIV-2KR"

( x i ) SEQUENCE DESCRIPTION: SEQ ID NO:3:

```
Met Gly Ala Arg Ser Ser Val Leu Arg Gly Lys Lys Val Asp Glu Leu
1               5                   10                  15

Glu Lys Ile Arg Leu Arg Pro Gly Gly Lys Lys Lys Tyr Arg Leu Lys
            20                  25                  30

His Ile Val Trp Ala Ala Asn Glu Leu Gly Lys Phe Gly Leu Ala Glu
                35                  40                  45

Ser Leu Leu Glu Ser Lys Glu Gly Cys Gln Lys Ile Ile Thr Val Leu
        50                  55                  60

Asp Pro Leu Val Pro Thr Gly Ser Glu Asn Leu Lys Ser Leu Phe Asn
65                  70                  75                  80

Thr Val Cys Val Ile Trp Cys Leu His Ala Glu Glu Lys Val Lys Asp
                85                  90                  95

Thr Glu Gly Ala Lys Gln Ile Val Gln Arg His Leu Val Ala Glu Thr
                100                 105                 110

Gly Thr Ala Asp Lys Met Pro Ser Thr Ser Arg Pro Ala Ala Pro Pro
            115                 120                 125

Ser Gly Arg Gly Gly Asn Tyr Pro Val Gln Gln Ile Ala Gly Asn Tyr
        130                 135                 140

Ser His Val Pro Leu Ser Pro Arg Thr Leu Asn Ala Trp Val Lys Leu
145                 150                 155                 160

Val Glu Glu Lys Lys Phe Gly Ala Glu Val Val Pro Gly Phe Gln Ala
                165                 170                 175

Leu Ser Glu Gly Cys Thr Pro Tyr Asp Ile Asn Gln Met Leu Asn Cys
            180                 185                 190

Val Gly Asp His Gln Ala Ala Met Gln Ile Ile Arg Glu Ile Ile Asn
        195                 200                 205

Glu Glu Ala Ala Asp Trp Asp Val Gln His Pro Ile Pro Gly Pro Leu
210                 215                 220

Pro Ala Gly Gln Leu Arg Glu Pro Arg Gly Ser Asp Ile Ala Gly Thr
225                 230                 235                 240

Thr Ser Thr Val Glu Glu Gln Ile Gln Trp Met Phe Arg Ala Gln Asn
                245                 250                 255

Pro Ile Pro Val Gly Asn Ile Tyr Arg Arg Trp Ile Gln Ile Gly Leu
            260                 265                 270

Gln Lys Cys Val Arg Met Tyr Asn Pro Thr Asn Ile Leu Asp Val Lys
        275                 280                 285

Gln Gly Pro Lys Glu Pro Phe Gln Ser Tyr Val Asp Arg Phe Tyr Lys
    290                 295                 300

Ser Leu Arg Ala Glu Gln Thr Asp Pro Ala Val Lys Asn Trp Met Thr
305                 310                 315                 320

Gln Thr Leu Leu Val Gln Asn Ala Asn Pro Asp Cys Lys Leu Val Leu
                325                 330                 335

Lys Gly Leu Gly Met Asn Pro Thr Leu Glu Glu Met Leu Thr Ala Cys
            340                 345                 350

Gln Gly Ile Gly Gly Pro Gly Gln Lys Ala Arg Leu Met Ala Glu Ala
```

-continued

|     |     |     | 355 |     |     |     | 360 |     |     |     | 365 |     |     |     |
|-----|-----|-----|-----|-----|-----|-----|-----|-----|-----|-----|-----|-----|-----|-----|
| Leu | Lys | Glu | Ala | Leu | Ala | Pro | Ala | Pro | Ile | Pro | Phe | Ala | Ala | Ala | Gln |
|     | 370 |     |     |     | 375 |     |     |     |     |     | 380 |     |     |     |
| Gln | Arg | Arg | Thr | Ile | Lys | Cys | Trp | Asn | Cys | Gly | Lys | Asp | Gly | His | Ser |
| 385 |     |     |     |     | 390 |     |     |     |     | 395 |     |     |     |     | 400 |
| Ala | Arg | Gln | Cys | Arg | Ala | Pro | Arg | Arg | Gln | Gly | Cys | Trp | Lys | Cys | Gly |
|     |     |     |     | 405 |     |     |     |     | 410 |     |     |     |     | 415 |     |
| Lys | Ser | Gly | His | Val | Met | Ala | Asn | Cys | Pro | Glu | Arg | Gln | Ala | Gly | Phe |
|     |     |     | 420 |     |     |     |     | 425 |     |     |     |     | 430 |     |     |
| Leu | Gly | Ile | Gly | Pro | Trp | Gly | Lys | Lys | Pro | Arg | Asn | Phe | Pro | Val | Thr |
|     |     | 435 |     |     |     |     | 440 |     |     |     |     | 445 |     |     |     |
| Arg | Val | Pro | Gln | Gly | Leu | Thr | Pro | Thr | Ala | Pro | Pro | Ala | Asp | Pro | Ala |
|     | 450 |     |     |     |     | 455 |     |     |     |     | 460 |     |     |     |     |
| Ala | Asp | Leu | Leu | Glu | Lys | Tyr | Leu | Gln | Gln | Gly | Arg | Lys | Gln | Lys | Glu |
| 465 |     |     |     |     | 470 |     |     |     |     | 475 |     |     |     |     | 480 |
| Gln | Lys | Met | Arg | Pro | Tyr | Lys | Glu | Val | Thr | Glu | Asp | Leu | Leu | His | Leu |
|     |     |     |     | 485 |     |     |     |     | 490 |     |     |     |     | 495 |     |
| Glu | Gln | Gly | Glu | Thr | Pro | His | Lys | Glu | Ala | Thr | Glu | Asp | Leu | Leu | His |
|     |     |     |     | 500 |     |     |     |     | 505 |     |     |     |     | 510 |     |
| Leu | Asn | Ser | Leu | Phe | Gly | Lys | Asp | Gln |     |     |     |     |     |     |     |
|     |     | 515 |     |     |     |     | 520 |     |     |     |     |     |     |     |     |

( 2 ) INFORMATION FOR SEQ ID NO:4:

( i ) SEQUENCE CHARACTERISTICS:
        ( A ) LENGTH: 253 amino acids
        ( B ) TYPE: amino acid
        ( C ) STRANDEDNESS:
        ( D ) TOPOLOGY: linear ( i i ) MOLECULE TYPE: protein ( i x ) FEATURE:
        ( A ) NAME/KEY: Protein
        ( B ) LOCATION: 1..253
        ( D ) OTHER INFORMATION: /note= "nef protein encoded by HIV-2KR"

( x i ) SEQUENCE DESCRIPTION: SEQ ID NO:4:

| Met | Gly | Ala | Ser | Gly | Ser | Lys | Lys | Cys | Ser | Arg | Ser | Leu | Gln | Gly | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Arg | Glu | Arg | Leu | Leu | Arg | Ala | Arg | Gly | Glu | Thr | Cys | Gly | Gly | Gln | Trp |
|     |     |     | 20  |     |     |     |     | 25  |     |     |     |     | 30  |     |     |
| Asp | Gly | Ser | Ala | Gly | Glu | Tyr | Leu | Gln | Phe | Gln | Glu | Gly | Ser | Gly | Arg |
|     |     | 35  |     |     |     |     | 40  |     |     |     |     | 45  |     |     |     |
| Gly | Gln | Asn | Leu | Pro | Ser | Cys | Glu | Gly | Gln | Arg | Tyr | Gln | Gln | Gly | Asp |
|     | 50  |     |     |     |     | 55  |     |     |     |     | 60  |     |     |     |     |
| Phe | Met | Asn | Thr | Pro | Trp | Arg | Thr | Pro | Ala | Ala | Gly | Arg | Glu | Gly | Thr |
| 65  |     |     |     |     | 70  |     |     |     |     | 75  |     |     |     |     | 80  |
| Leu | Tyr | Lys | Gln | Gln | Asn | Met | Asp | Asp | Val | Asp | Ala | Asp | Asn | Asp | Asn |
|     |     |     |     | 85  |     |     |     |     | 90  |     |     |     |     | 95  |     |
| Leu | Ile | Gly | Val | Pro | Val | Thr | Pro | Arg | Val | Pro | Leu | Arg | Ala | Met | Thr |
|     |     |     | 100 |     |     |     |     | 105 |     |     |     |     | 110 |     |     |
| Tyr | Lys | Leu | Ala | Val | Asp | Ile | Ser | His | Phe | Leu | Asn | Glu | Lys | Gly | Gly |
|     |     | 115 |     |     |     |     | 120 |     |     |     |     | 125 |     |     |     |
| Leu | Asp | Gly | Met | Tyr | Tyr | Ser | Glu | Arg | Arg | His | Arg | Ile | Leu | Asp | Ile |
|     | 130 |     |     |     |     | 135 |     |     |     |     | 140 |     |     |     |     |
| Tyr | Met | Glu | Lys | Glu | Glu | Gly | Ile | Ile | Pro | Asp | Trp | Gln | Asn | Tyr | Thr |
| 145 |     |     |     |     | 150 |     |     |     |     | 155 |     |     |     |     | 160 |

His Gly Pro Gly Val Arg Tyr Pro Lys Phe Phe Gly Trp Leu Trp Lys
            165                 170                 175

Leu Val Pro Val Asp Val Pro Gln Gly Glu Glu Asp His Cys Leu Leu
            180                 185                 190

His Pro Ala Gln Thr Ser Gly Ser Asp Asp Pro His Gly Glu Thr Leu
            195                 200                 205

Met Trp Arg Phe Asp Pro Arg Leu Ala Tyr Glu Tyr Thr Ala Phe Asn
210                         215                 220

Arg Tyr Pro Glu Glu Phe Gly Tyr Lys Ser Gly Leu Pro Glu Glu Glu
225                 230                 235                 240

Trp Lys Ala Lys Leu Lys Ala Arg Gly Ile Pro Phe Ser
            245                 250

( 2 ) INFORMATION FOR SEQ ID NO:5:

( i ) SEQUENCE CHARACTERISTICS:
        ( A ) LENGTH: 1055 amino acids
        ( B ) TYPE: amino acid
        ( C ) STRANDEDNESS:
        ( D ) TOPOLOGY: linear ( i i ) MOLECULE TYPE: protein ( i x ) FEATURE:
        ( A ) NAME/KEY: Protein
        ( B ) LOCATION: 1..1055
        ( D ) OTHER INFORMATION: /note= "pol protein encoded by HIV-2KR"

( x i ) SEQUENCE DESCRIPTION: SEQ ID NO:5:

Lys Thr Gly Leu Leu Glu Met Trp Gln Ile Arg Thr Cys His Gly Lys
1               5                   10                  15

Leu Pro Arg Lys Thr Gly Trp Phe Phe Arg Asp Trp Pro Met Gly Lys
            20                  25                  30

Glu Ala Ser Gln Leu Pro Arg Asp Pro Ser Pro Ala Gly Ala Asp Thr
            35                  40                  45

Asn Ser Thr Pro Ser Arg Pro Ser Ser Arg Pro Ala Arg Glu Val Leu
50                      55                  60

Ala Ala Arg Glu Glu Ala Glu Arg Ala Glu Asn Glu Thr Ile Gln Gly
65                      70                  75                  80

Gly Asp Arg Gly Leu Thr Ala Pro Arg Thr Arg Arg Asp Thr Thr Gln
            85                  90                  95

Arg Gly Asp Arg Gly Phe Ala Ala Pro Gln Phe Ser Leu Trp Lys Arg
            100                 105                 110

Pro Val Val Thr Ala Tyr Val Glu Gly Gln Pro Val Glu Val Leu Leu
            115                 120                 125

Asp Thr Gly Ala Asp Asp Ser Ile Val Ala Gly Ile Glu Leu Gly Ser
            130                 135                 140

Asn Tyr Ser Pro Lys Ile Val Gly Gly Ile Gly Gly Phe Ile Asn Thr
145                 150                 155                 160

Lys Glu Tyr Lys Asn Val Glu Ile Lys Val Leu Asn Lys Lys Val Lys
                165                 170                 175

Ala Thr Ile Met Thr Gly Asp Thr Pro Ile Asn Ile Phe Gly Arg Asn
            180                 185                 190

Ile Leu Thr Ala Leu Gly Met Ser Leu Asn Leu Pro Val Ala Lys Val
            195                 200                 205

Asp Pro Ile Lys Val Ile Leu Lys Pro Gly Lys Asp Gly Pro Lys Val
            210                 215                 220

Arg Gln Trp Pro Leu Thr Lys Glu Lys Ile Glu Ala Leu Lys Glu Ile
225                 230                 235                 240

-continued

| | | | | | | | | | | | | | |
|---|---|---|---|---|---|---|---|---|---|---|---|---|---|
| Cys | Glu | Lys | Met | Glu | Arg | Glu | Gly | Gln | Leu | Glu | Glu | Ala | Pro | Pro | Thr |
| | | | | 245 | | | | 250 | | | | | 255 |
| Asn | Pro | Tyr | Asn | Thr | Pro | Thr | Phe | Ala | Ile | Lys | Lys | Lys | Asp | Lys | Asn |
| | | | 260 | | | | 265 | | | | 270 | | |
| Lys | Trp | Arg | Met | Leu | Ile | Asp | Phe | Arg | Glu | Leu | Asn | Lys | Val | Thr | Gln |
| | | 275 | | | | 280 | | | | 285 | | | |
| Glu | Phe | Thr | Glu | Ile | Gln | Leu | Gly | Ile | Pro | His | Pro | Ala | Gly | Leu | Ala |
| | 290 | | | | 295 | | | | 300 | | | | |
| Lys | Lys | Arg | Arg | Ile | Thr | Val | Leu | Asp | Ile | Gly | Asp | Ala | Tyr | Phe | Ser |
| 305 | | | | 310 | | | | 315 | | | | 320 |
| Ile | Pro | Leu | His | Glu | Asp | Phe | Arg | Gln | Tyr | Thr | Ala | Phe | Thr | Leu | Pro |
| | | | 325 | | | | 330 | | | | 335 |
| Thr | Val | Asn | Asn | Ala | Glu | Pro | Gly | Lys | Arg | Tyr | Ile | Tyr | Lys | Val | Leu |
| | | | 340 | | | | 345 | | | | 350 |
| Pro | Gln | Gly | Trp | Lys | Gly | Ser | Pro | Ala | Ile | Phe | Gln | His | Thr | Met | Arg |
| | | 355 | | | | 360 | | | | 365 |
| Gln | Val | Leu | Glu | Pro | Phe | Arg | Lys | Ala | Asn | Pro | Asp | Val | Ile | Leu | Val |
| | 370 | | | | 375 | | | | 380 |
| Gln | Tyr | Met | Asp | Asp | Ile | Leu | Ile | Ala | Ser | Asp | Arg | Thr | Asp | Leu | Glu |
| 385 | | | | 390 | | | | 395 | | | | 400 |
| His | Asp | Arg | Thr | Val | Leu | Gln | Leu | Lys | Glu | Leu | Leu | Asn | Gly | Leu | Gly |
| | | | 405 | | | | 410 | | | | 415 |
| Phe | Ser | Thr | Pro | Asp | Glu | Lys | Phe | Gln | Lys | Asp | Pro | Pro | Tyr | Lys | Trp |
| | | | 420 | | | | 425 | | | | 430 |
| Met | Gly | Tyr | Glu | Leu | Trp | Pro | Thr | Lys | Trp | Lys | Leu | Gln | Lys | Ile | Gln |
| | | 435 | | | | 440 | | | | 445 |
| Leu | Pro | Gln | Lys | Glu | Val | Trp | Thr | Val | Asn | Asp | Ile | Gln | Lys | Leu | Val |
| | 450 | | | | 455 | | | | 460 |
| Gly | Val | Leu | Asn | Trp | Ala | Ala | Gln | Ile | Tyr | Pro | Gly | Ile | Lys | Thr | Lys |
| 465 | | | | 470 | | | | 475 | | | | 480 |
| His | Leu | Cys | Arg | Leu | Ile | Arg | Gly | Lys | Met | Thr | Leu | Thr | Glu | Glu | Val |
| | | | 485 | | | | 490 | | | | 495 |
| Gln | Trp | Thr | Glu | Leu | Ala | Glu | Ala | Glu | Leu | Glu | Glu | Asn | Lys | Ile | Ile |
| | | | 500 | | | | 505 | | | | 510 |
| Leu | Ser | Gln | Glu | Gln | Glu | Gly | Cys | Tyr | Tyr | Gln | Glu | Glu | Lys | Glu | Leu |
| | | 515 | | | | 520 | | | | 525 |
| Glu | Ala | Thr | Val | Gln | Lys | Asp | Gln | Asp | Asn | Gln | Trp | Thr | Tyr | Lys | Ile |
| | 530 | | | | 535 | | | | 540 |
| His | Gln | Gly | Glu | Lys | Ile | Leu | Lys | Val | Gly | Lys | Tyr | Ala | Lys | Ile | Lys |
| 545 | | | | 550 | | | | 555 | | | | 560 |
| Asn | Thr | His | Thr | Asn | Gly | Val | Arg | Leu | Leu | Ala | His | Val | Val | Gln | Lys |
| | | | 565 | | | | 570 | | | | 575 |
| Ile | Gly | Lys | Glu | Ala | Leu | Val | Ile | Trp | Gly | Arg | Ile | Pro | Lys | Phe | His |
| | | | 580 | | | | 585 | | | | 590 |
| Leu | Pro | Val | Glu | Arg | Glu | Thr | Trp | Glu | Gln | Trp | Trp | Asp | Asn | Tyr | Trp |
| | | 595 | | | | 600 | | | | 605 |
| Gln | Val | Thr | Trp | Ile | Pro | Asp | Trp | Asp | Phe | Val | Ser | Thr | Pro | Pro | Leu |
| | 610 | | | | 615 | | | | 620 |
| Val | Arg | Leu | Ala | Phe | Asn | Leu | Val | Lys | Asp | Pro | Ile | Pro | Gly | Glu | Glu |
| 625 | | | | 630 | | | | 635 | | | | 640 |
| Thr | Phe | Tyr | Thr | Asp | Gly | Ser | Cys | Asn | Arg | Gln | Ser | Lys | Glu | Gly | Lys |
| | | | 645 | | | | 650 | | | | 655 |
| Ala | Gly | Tyr | Ile | Thr | Asp | Arg | Gly | Arg | Asp | Lys | Val | Arg | Ile | Leu | Glu |

|     |     |     |     |     |     |     |     |     |     |     |     |     |     |     |
| --- | --- | --- | --- | --- | --- | --- | --- | --- | --- | --- | --- | --- | --- | --- |
|     |     |     |     | 660 |     |     |     | 665 |     |     |     | 670 |     |     |
| Gln | Thr | Thr | Asn | Gln | Gln | Ala | Glu | Leu | Glu | Ala | Phe | Ala | Met | Ala | Leu |
|     |     | 675 |     |     |     | 680 |     |     |     |     | 685 |     |     |     |
| Thr | Asp | Ser | Gly | Pro | Lys | Ala | Asn | Ile | Ile | Val | Asp | Ser | Gln | Tyr | Val |
|     | 690 |     |     |     | 695 |     |     |     |     | 700 |     |     |     |     |
| Met | Gly | Ile | Val | Ala | Gly | Gln | Pro | Thr | Glu | Ser | Glu | Ser | Lys | Leu | Val |
| 705 |     |     |     |     | 710 |     |     |     | 715 |     |     |     |     |     | 720 |
| Asn | Gln | Ile | Ile | Glu | Glu | Met | Ile | Lys | Lys | Glu | Thr | Leu | Tyr | Val | Ala |
|     |     |     |     | 725 |     |     |     |     | 730 |     |     |     |     | 735 |     |
| Trp | Val | Pro | Ala | His | Lys | Gly | Ile | Gly | Gly | Asn | Gln | Glu | Val | Asp | His |
|     |     |     | 740 |     |     |     |     | 745 |     |     |     |     | 750 |     |     |
| Leu | Val | Ser | Gln | Gly | Ile | Arg | Gln | Val | Leu | Phe | Leu | Glu | Lys | Ile | Glu |
|     |     | 755 |     |     |     |     | 760 |     |     |     |     | 765 |     |     |     |
| Pro | Ala | Gln | Glu | Glu | His | Glu | Lys | Tyr | His | Ser | Asn | Val | Lys | Glu | Leu |
|     | 770 |     |     |     |     | 775 |     |     |     |     | 780 |     |     |     |     |
| Ser | His | Lys | Phe | Gly | Leu | Pro | Lys | Leu | Val | Ala | Arg | Gln | Ile | Val | Asn |
| 785 |     |     |     |     | 790 |     |     |     |     | 795 |     |     |     |     | 800 |
| Thr | Cys | Ala | Gln | Cys | Gln | Gln | Lys | Gly | Glu | Ala | Ile | His | Gly | Gln | Val |
|     |     |     |     | 805 |     |     |     |     | 810 |     |     |     |     | 815 |     |
| Asp | Ala | Glu | Leu | Gly | Thr | Trp | Gln | Met | Asp | Cys | Thr | His | Leu | Glu | Gly |
|     |     |     | 820 |     |     |     |     | 825 |     |     |     |     | 830 |     |     |
| Lys | Ile | Ile | Ile | Val | Ala | Val | His | Val | Ala | Ser | Gly | Phe | Ile | Glu | Ala |
|     |     | 835 |     |     |     |     | 840 |     |     |     |     | 845 |     |     |     |
| Glu | Val | Ile | Pro | Gln | Glu | Thr | Gly | Arg | Gln | Thr | Ala | Leu | Phe | Leu | Leu |
|     | 850 |     |     |     |     | 855 |     |     |     |     | 860 |     |     |     |     |
| Lys | Leu | Ala | Ser | Arg | Trp | Pro | Ile | Thr | His | Leu | His | Thr | Asp | Asn | Gly |
| 865 |     |     |     |     | 870 |     |     |     |     | 875 |     |     |     |     | 880 |
| Ala | Asn | Phe | Thr | Ser | Gln | Glu | Val | Lys | Met | Val | Ala | Trp | Trp | Thr | Gly |
|     |     |     |     | 885 |     |     |     |     | 890 |     |     |     |     | 895 |     |
| Ile | Glu | Gln | Ser | Phe | Gly | Val | Pro | Tyr | Asn | Pro | Gln | Ser | Gln | Gly | Val |
|     |     |     | 900 |     |     |     |     | 905 |     |     |     |     | 910 |     |     |
| Val | Glu | Ala | Met | Asn | His | His | Leu | Lys | Asn | Gln | Ile | Ser | Arg | Ile | Arg |
|     |     | 915 |     |     |     |     | 920 |     |     |     |     | 925 |     |     |     |
| Glu | Gln | Ala | Asn | Thr | Met | Glu | Thr | Ile | Val | Leu | Met | Ala | Val | His | Cys |
|     | 930 |     |     |     |     | 935 |     |     |     |     | 940 |     |     |     |     |
| Met | Asn | Phe | Lys | Arg | Arg | Gly | Gly | Ile | Gly | Asp | Met | Thr | Pro | Ala | Glu |
| 945 |     |     |     |     | 950 |     |     |     |     | 955 |     |     |     |     | 960 |
| Arg | Leu | Ile | Asn | Met | Ile | Thr | Thr | Glu | Gln | Glu | Ile | Gln | Phe | Leu | His |
|     |     |     |     | 965 |     |     |     |     | 970 |     |     |     |     | 975 |     |
| Ala | Lys | Asn | Ser | Lys | Leu | Lys | Asn | Phe | Arg | Val | Tyr | Phe | Arg | Glu | Gly |
|     |     |     | 980 |     |     |     |     | 985 |     |     |     |     | 990 |     |     |
| Arg | Asp | Gln | Leu | Trp | Lys | Gly | Pro | Gly | Glu | Leu | Leu | Trp | Lys | Gly | Asp |
|     |     | 995 |     |     |     |     | 1000 |     |     |     |     | 1005 |     |     |     |
| Gly | Ala | Val | Ile | Val | Lys | Val | Gly | Thr | Asp | Ile | Lys | Ile | Val | Pro | Arg |
|     |     | 1010 |     |     |     |     | 1015 |     |     |     |     | 1020 |     |     |     |
| Arg | Lys | Ala | Lys | Ile | Ile | Arg | Asp | Tyr | Gly | Gly | Arg | Arg | Glu | Val | Asp |
| 1025 |     |     |     |     | 1030 |     |     |     |     | 1035 |     |     |     |     | 1040 |
| Ser | Ser | Ser | His | Leu | Glu | Gly | Thr | Arg | Glu | Asp | Gly | Glu | Val | Ala |     |
|     |     |     |     | 1045 |     |     |     |     | 1050 |     |     |     |     | 1055 |     |

( 2 ) INFORMATION FOR SEQ ID NO:6:

( i ) SEQUENCE CHARACTERISTICS:
( A ) LENGTH: 176 amino acids
( B ) TYPE: amino acid (C) STRANDEDNESS:
(D) TOPOLOGY: linear (ii) MOLECULE TYPE: protein (ix) FEATURE:
(A) NAME/KEY: Protein
(B) LOCATION: 1..176
(D) OTHER INFORMATION: /note= "rev protein encoded by HIV-2KR"

(xi) SEQUENCE DESCRIPTION: SEQ ID NO:6:

| Met | Asn | Gly | Arg | Ala | Asp | Glu | Glu | Gly | Leu | Gln | Gly | Leu | Ile | Arg | Leu |
|---|---|---|---|---|---|---|---|---|---|---|---|---|---|---|---|
| 1 | | | | 5 | | | | | 10 | | | | | 15 | |
| Leu | His | Gln | Thr | Asp | Pro | Tyr | Pro | Gln | Gly | Leu | Gly | Thr | Ala | Arg | Gln |
| | | | 20 | | | | | 25 | | | | 30 | | | |
| Arg | Arg | Asn | Arg | Arg | Arg | Arg | Lys | Gln | His | Trp | Arg | Gln | Leu | Val | |
| | | 35 | | | | | 40 | | | | 45 | | | | |
| Ala | Leu | Ala | Asn | Ser | Ile | Tyr | Thr | Phe | Pro | Asp | Pro | Pro | Ala | Asp | Ser |
| | 50 | | | | | 55 | | | | | 60 | | | | |
| Pro | Leu | Asp | Arg | Ala | Ile | Gln | Arg | Leu | Gln | Gly | Leu | Thr | Ile | Gln | Glu |
| 65 | | | | | 70 | | | | | 75 | | | | | 80 |
| Leu | Pro | Asp | Pro | Pro | Thr | Asn | Leu | Pro | Glu | Ser | Ser | Glu | Ser | Thr | Asn |
| | | | | 85 | | | | | 90 | | | | | 95 | |
| Asn | Asn | Gln | Gly | Leu | Ala | Glu | Thr | Tyr | Asn | Ser | Leu | Pro | Ala | Ile | Trp |
| | | | | 100 | | | | | 105 | | | | | 110 | |
| Val | Arg | Val | Asp | Pro | Arg | Ser | Ala | Pro | Gly | Pro | Cys | Lys | Asp | Tyr | Glu |
| | | | 115 | | | | | 120 | | | | 125 | | | |
| Arg | Asp | Ser | Cys | Glu | Arg | Val | Glu | Arg | Leu | Val | Gly | Gly | Asn | Gly | Thr |
| | | 130 | | | | | 135 | | | | | 140 | | | |
| Asp | Arg | Gln | Gly | Asn | Thr | Cys | Ser | Ser | Lys | Lys | Asp | Gln | Ala | Gly | Gly |
| 145 | | | | | 150 | | | | | 155 | | | | | 160 |
| Arg | Thr | Cys | Pro | Pro | Val | Arg | Gly | Ser | Gly | Ile | Asn | Arg | Glu | Thr | Leu |
| | | | | 165 | | | | | 170 | | | | | 175 | |

(2) INFORMATION FOR SEQ ID NO:7:

(i) SEQUENCE CHARACTERISTICS:
(A) LENGTH: 127 amino acids
(B) TYPE: amino acid
(C) STRANDEDNESS:
(D) TOPOLOGY: linear (ii) MOLECULE TYPE: protein (ix) FEATURE:
(A) NAME/KEY: Protein
(B) LOCATION: 1..127
(D) OTHER INFORMATION: /note= "tat protein encoded by HIV-2KR"

(xi) SEQUENCE DESCRIPTION: SEQ ID NO:7:

| Met | Glu | Thr | Pro | Ser | Lys | Ala | Pro | Glu | Ser | Ser | Leu | Met | Ser | Cys | Asn |
|---|---|---|---|---|---|---|---|---|---|---|---|---|---|---|---|
| 1 | | | | 5 | | | | | 10 | | | | | 15 | |
| Glu | Pro | Ser | Ser | Cys | Thr | Ser | Glu | Gln | Asp | Val | Lys | Ser | Gln | Glu | Leu |
| | | | 20 | | | | | 25 | | | | | 30 | | |
| Ala | Lys | Gln | Gly | Glu | Arg | Leu | Leu | Ser | Gln | Leu | Tyr | Gln | Pro | Leu | Glu |
| | | | 35 | | | | 40 | | | | | 45 | | | |
| Ala | Cys | Asn | Asn | Pro | Cys | Tyr | Cys | Lys | Lys | Cys | Cys | Tyr | His | Cys | Gln |
| | 50 | | | | | 55 | | | | | 60 | | | | |
| Leu | Cys | Phe | Leu | Lys | Lys | Gly | Leu | Gly | Ile | Cys | Tyr | Glu | Arg | Lys | Gly |
| 65 | | | | | 70 | | | | | 75 | | | | | 80 |
| Arg | Arg | Arg | Arg | Thr | Pro | Arg | Ala | His | Ser | Ser | Ala | Ser | Asp | Lys | |
| | | | | 85 | | | | | 90 | | | | | 95 | |

```
        Ser  Ile  Ser  Thr  Arg  Thr  Gly  Asn  Ser  Gln  Thr  Glu  Lys  Lys  Gln  Thr
                       100                      105                      110

Lys  Thr  Pro  Glu  Thr  Ala  Leu  Glu  Thr  Ala  Arg  Gly  Leu  Gly  Gln
                       115                      120                      125
```

( 2 ) INFORMATION FOR SEQ ID NO:8:

( i ) SEQUENCE CHARACTERISTICS:
        ( A ) LENGTH: 215 amino acids
        ( B ) TYPE: amino acid
        ( C ) STRANDEDNESS:
        ( D ) TOPOLOGY: linear ( i i ) MOLECULE TYPE: protein ( i x ) FEATURE:
        ( A ) NAME/KEY: Protein
        ( B ) LOCATION: 1..215
        ( D ) OTHER INFORMATION: /note= "vif protein encoded by HIV-2KR"

( x i ) SEQUENCE DESCRIPTION: SEQ ID NO:8:

```
        Met  Glu  Glu  Gly  Glu  Arg  Trp  Ile  Val  Val  Pro  Thr  Trp  Arg  Val  Pro
        1                   5                        10                       15

Gly  Arg  Met  Glu  Lys  Trp  His  Ser  Leu  Val  Lys  Tyr  Leu  Lys  His  Arg
                       20                      25                       30

Thr  Lys  Asp  Leu  Glu  Gly  Val  Cys  Tyr  Val  Pro  His  His  Lys  Val  Gly
                       35                      40                       45

Trp  Ala  Trp  Trp  Thr  Cys  Ser  Arg  Val  Ile  Phe  Pro  Leu  Gln  Gly  Asn
                  50                      55                       60

Ser  His  Leu  Glu  Ile  Gln  Ala  Tyr  Trp  Asn  Leu  Thr  Pro  Glu  Lys  Gly
        65                           70                      75                       80

Trp  Leu  Ser  Ser  Tyr  Ala  Val  Arg  Ile  Thr  Trp  Tyr  Thr  Glu  Arg  Phe
                            85                      90                       95

Trp  Thr  Asp  Val  Thr  Pro  Asp  Cys  Ala  Asp  Ser  Leu  Ile  His  Ser  Thr
                       100                     105                      110

Tyr  Phe  Ser  Cys  Phe  Thr  Ala  Gly  Glu  Val  Arg  Arg  Ala  Ile  Arg  Gly
                       115                     120                      125

Glu  Lys  Leu  Leu  Ser  Cys  Cys  Asn  Tyr  Pro  Gln  Ala  His  Arg  Ser  Lys
                  130                     135                      140

Val  Pro  Leu  Leu  Gln  Phe  Leu  Ala  Leu  Val  Val  Gln  Gln  Asn  Gly
        145                          150                     155                      160

Arg  Pro  Gln  Lys  Asn  Ser  Thr  Thr  Arg  Lys  Arg  Trp  Arg  Ser  Asn  Tyr
                            165                     170                      175

Trp  Arg  Gly  Phe  Arg  Leu  Ala  Arg  Lys  Asp  Gly  Arg  Gly  His  Lys  Gln
                       180                     185                      190

Arg  Gly  Ser  Glu  Pro  Pro  Ala  Ser  Gly  Ala  Tyr  Phe  Pro  Gly  Val  Ala
                       195                     200                      205

Lys  Val  Leu  Glu  Ile  Leu  Ala
                       210                215
```

( 2 ) INFORMATION FOR SEQ ID NO:9:

( i ) SEQUENCE CHARACTERISTICS:
        ( A ) LENGTH: 105 amino acids
        ( B ) TYPE: amino acid
        ( C ) STRANDEDNESS:
        ( D ) TOPOLOGY: linear ( i i ) MOLECULE TYPE: protein ( i x ) FEATURE:
        ( A ) NAME/KEY: Protein (B) LOCATION: 1..105
(D) OTHER INFORMATION: /note= "vpr protein encoded by HIV-2KR"

(xi) SEQUENCE DESCRIPTION: SEQ ID NO:9:

| Met | Thr | Glu | Ala | Pro | Ala | Glu | Phe | Pro | Pro | Glu | Asp | Glu | Thr | Pro | Pro |
|---|---|---|---|---|---|---|---|---|---|---|---|---|---|---|---|
| 1 | | | | 5 | | | | | 10 | | | | | 15 | |

| Arg | Gly | Pro | Gly | Asp | Glu | Trp | Val | Ile | Gly | Ile | Leu | Arg | Glu | Leu | Arg |
|---|---|---|---|---|---|---|---|---|---|---|---|---|---|---|---|
| | | | 20 | | | | | 25 | | | | | 30 | | |

| Glu | Glu | Ala | Leu | Lys | His | Phe | Asp | Pro | Arg | Leu | Leu | Thr | Thr | Leu | Gly |
|---|---|---|---|---|---|---|---|---|---|---|---|---|---|---|---|
| | | | 35 | | | | 40 | | | | | 45 | | | |

| Asn | Tyr | Ile | Cys | Ala | Arg | His | Gly | Asp | Thr | Leu | Glu | Ser | Ala | Arg | Glu |
|---|---|---|---|---|---|---|---|---|---|---|---|---|---|---|---|
| | 50 | | | | | 55 | | | | | 60 | | | | |

| Leu | Ile | Asn | Val | Leu | Gln | Arg | Ala | Leu | Phe | Val | His | Phe | Arg | Ala | Gly |
|---|---|---|---|---|---|---|---|---|---|---|---|---|---|---|---|
| 65 | | | | | 70 | | | | | 75 | | | | | 80 |

| Cys | Lys | Ile | Ser | Arg | Ile | Gly | Gln | Thr | Arg | Gly | Glu | Thr | Pro | Phe | Ser |
|---|---|---|---|---|---|---|---|---|---|---|---|---|---|---|---|
| | | | | 85 | | | | | 90 | | | | | 95 | |

| Ala | Ile | Pro | Thr | Pro | Arg | Gly | Met | Gln |
|---|---|---|---|---|---|---|---|---|
| | | | 100 | | | | | 105 |

(2) INFORMATION FOR SEQ ID NO:10:

(i) SEQUENCE CHARACTERISTICS:
(A) LENGTH: 762 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: -
(B) LOCATION: 1..762
(D) OTHER INFORMATION: /label=nef
/ note= "HIV-2KR subsequence encoding
nef gene"

(xi) SEQUENCE DESCRIPTION: SEQ ID NO:10:

| | | | | | | |
|---|---|---|---|---|---|---|
| ATGGGTGCGA | GTGGATCCAA | GAAGTGCTCC | AGGTCCTTGC | AAGGACTACG | AGAGAGACTC | 60 |
| TTGCGAGCGC | GTGGAGAGAC | TTGTGGGGGG | CAATGGGACG | GATCGGCAGG | GGAATACTTG | 120 |
| CAGTTCCAAG | AAGGATCAGG | CAGGGGGCAG | AACTTGCCCT | CCTGTGAGGG | GCAGCGGTAT | 180 |
| CAACAGGGAG | ACTTTATGAA | CACCCCATGG | AGAACTCCAG | CAGCAGGAAG | GGAGGGAACA | 240 |
| TTGTACAAGC | AACAAAATAT | GGATGATGTA | GATGCAGATA | ATGATAACCT | AATAGGGGTC | 300 |
| CCTGTCACAC | CAAGAGTACC | ATTAAGGGCA | ATGACATATA | AGTTGGCAGT | AGATATATCA | 360 |
| CATTTTCTAA | ATGAAAAGGG | GGGACTGGAT | GGGATGTATT | ACAGTGAGAG | AAGACATAGA | 420 |
| ATCTTAGACA | TATACATGGA | AAAGGAAGAA | GGGATAATTC | CAGATTGGCA | GAACTATACT | 480 |
| CATGGGCCAG | GAGTAAGGTA | CCCAAAGTTC | TTTGGGTGGC | TATGGAAGCT | AGTACCAGTA | 540 |
| GACGTCCCAC | AAGGTGAAGA | GGACCACTGC | TTACTACACC | CAGCACAAAC | AAGCGGGTCT | 600 |
| GATGACCCTC | ATGGGGAAAC | ATTAATGTGG | AGGTTTGACC | CTAGGCTGGC | CTATGAGTAT | 660 |
| ACGGCTTTTA | ATCGATACCC | AGAAGAATTT | GGGTATAAGT | CAGGCCTGCC | AGAAGAAGAG | 720 |
| TGGAAGGCAA | AACTGAAAGC | AAGAGGGATA | CCATTTAGTT | AA | | 762 |

(2) INFORMATION FOR SEQ ID NO:11:

(i) SEQUENCE CHARACTERISTICS:
(A) LENGTH: 648 base pairs
(B) TYPE: nucleic acid
(C) STRANDEDNESS: single
(D) TOPOLOGY: linear ( i i ) MOLECULE TYPE: DNA ( i x ) FEATURE:
        ( A ) NAME/KEY: -
        ( B ) LOCATION: 1..648
        ( D ) OTHER INFORMATION: /label=vif
            / note= "HIV-2KR subsequence encoding
               vif gene"

( x i ) SEQUENCE DESCRIPTION: SEQ ID NO:11:

```
ATGGAGGAAG  GCGAGAGGTG  GATAGTAGTT  CCCACTTGGA  GGGTACCAGG  GAGGATGGAG    60
AAGTGGCATA  GCCTTGTCAA  GTATCTAAAA  CACAGAACAA  AAGATCTGGA  AGGGGTGTGC   120
TATGTTCCCC  ACCATAAGGT  GGGATGGGCA  TGGTGGACTT  GCAGCAGGGT  AATATTCCCA   180
TTACAAGGAA  ATAGTCACCT  AGAGATACAG  GCATATTGGA  ACCTAACACC  AGAAAAGGA    240
TGGCTCTCCT  CTTATGCAGT  AAGAATAACC  TGGTATACAG  AGAGGTTCTG  GACAGATGTT   300
ACCCCAGACT  GTGCAGACTC  CCTAATACAT  AGCACTTATT  TCTCTTGTTT  TACGGCGGGT   360
GAAGTAAGAA  GAGCCATCAG  AGGGGAAAAG  TTACTGTCCT  GCTGCAATTA  CCCCCAAGCC   420
CATAGATCTA  AGGTACCGTT  ACTCCAATTT  CTGGCCTTAG  TAGTAGTGCA  ACAAAATGGC   480
AGACCCCAGA  AAAACAGTAC  CACCAGGAAA  CGGTGGCGAA  GTAACTATTG  AGAGGCTTT    540
CGCTTGGCTA  GAAAGGATGG  TAGAGGCCAT  AAACAGAGAG  GCAGTGAACC  ACCTGCCTCG   600
GGAGCTTATT  TTCCAGGTGT  GGCAAAGGTC  CTGGAGATAC  TGGCATGA                 648
```

( 2 ) INFORMATION FOR SEQ ID NO:12:

( i ) SEQUENCE CHARACTERISTICS:
        ( A ) LENGTH: 1070 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: -
        ( B ) LOCATION: 1..1070
        ( D ) OTHER INFORMATION: /note= "HIV-2KR subsequence encoding
               5' long terminal repeat (LTR)"

( x i ) SEQUENCE DESCRIPTION: SEQ ID NO:12:

```
TGGATGGGAT  GTATTACAGT  GAGAGAAGGA  CATAGAATCT  TAGACATATA  CATGGAAAAG    60
GAAGAAGGGA  TAATTCCAGA  TTGGCAGAAC  TATACTCATG  GGCCAGGAGT  AAGGTACCCA   120
AAGTTCTTTG  GGTGGCTATG  GAAGCTAGTA  CCAGTAGACG  TCCCACAAGG  TGAAGAGGAC   180
CACTGCTTAC  TACACCCAGC  ACAAACAAGC  GGGTCTGATG  ACCCTCATGG  GGAAACATTA   240
ATGTGGAGGT  TTGACCCTAG  GCTGGCCTAT  GAGTATACGG  CTTTTAATCG  ATACCCAGAA   300
GAATTTGGGT  ATAAGTCAGG  CCTGCCAGAA  GAAGAGTGGA  AGGCAAAACT  GAAAGCAAGA   360
GGGATACCAT  TTAGTTAAAG  ACAGGAACAG  CTATATTTGG  TCAGAACAGG  AAGTAGATGA   420
TGAAACTGCA  GGGACTTTCC  AGAAGGGGCT  GTAACCAGGG  GAGGGACGTG  GGAGGAACCG   480
GTGGGGAACG  CCCTCATACT  TCTGTATAAA  TGTACCCGCT  GCTTGCATTG  TATTCAGTCG   540
CTCTGCGGAG  AGGCTGGCAG  ATCGAGCCCT  GGGAGGTTCT  CTCCAGCACT  AGCAGGTAGA   600
GCCTGGGTGT  TCCCTGCTAG  ACTCTCACCA  GTACTTGGCC  GGTACTGGGC  AGACGGCTCC   660
ACGCTTGCTT  GCTTAAAGAC  CTCTTAATAA  AGCTGCCAGT  TAGAAGCAAG  TTAAGTGTGT   720
GTTCCCATCT  CTCCTAGTCG  CCGCCTGGTC  ATTCGGTGTT  CACCTAAGTG  ACAAGACCCT   780
GGTCTGTTAG  GACCCTTCTT  GCTTTGGGGA  ACCGAAGCGG  GAAAATACCT  AGCAGATTGG   840
```

| | | | | | |
|---|---|---|---|---|---|
| CGCCCGAACA | GGACTTGAAG | GAGACTGGAA | CACGGCTGAG | TGAAGGCAGT | AAGGGCGGCA | 900 |
| GGAACAAACC | ACGACGGAGT | GCTCCTAGAA | AGGCGCGGGC | CGAGGTACCA | AAGGCGGCGT | 960 |
| GTGGAGCGGG | AGTAAAGAGG | CCTCCGGGTG | AAGGTAAGTA | CCTACACCAA | AAACTGTAGC | 1020 |
| CAGAAAAAGG | CTTGTTATCC | TACCTTTAGA | CAGGTAGAAG | ATTGTGGGAG | | 1070 |

( 2 ) INFORMATION FOR SEQ ID NO:13:

( i ) SEQUENCE CHARACTERISTICS:
        ( A ) LENGTH: 2574 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: -
        ( B ) LOCATION: 1..2574
        ( D ) OTHER INFORMATION: /label=env
            / note= "HIV-2KR subsequence encoding
            env gene"

( x i ) SEQUENCE DESCRIPTION: SEQ ID NO:13:

| | | | | | |
|---|---|---|---|---|---|
| ATGGATAGTA | GAAATCAGCT | AATTGTTGCC | ATTTTACTAA | CTAGTGCTTG | CTTAATATAT | 60 |
| TGCGCCCAAT | ATGTGACTGT | TTTCTATGGC | ATACCCGCGT | GGAAGAATGC | ATCCATTCCC | 120 |
| CTCTTTTGTG | CAACCAGAAA | TAGAGATACT | TGGGGAACCA | TACAGTGCTT | GCCAGACAAT | 180 |
| GATGATTATC | AGGAAATACC | TTTAAATGTG | ACAGAGGCTT | TTGACGCATG | GAACAATACA | 240 |
| GTAACAGAAC | AAGCAGTAGA | AGATGTCTGG | AATCTATTTG | AGACATCAGT | AAAACCATGT | 300 |
| GTCAAATTAA | CACCCTTATG | TGTGCAAATG | GAATGTAACA | GCACAAGTAC | AGAGAGCAGT | 360 |
| AACAGCACAA | GTGAGGGGAG | CACAGTCCCA | GAGATATTAA | ACGAAACTAC | TTCATGCATA | 420 |
| ACCAACAACA | GCTGCTCAGA | TTTAGGGAGT | GAAGAGGTAG | TCGATTGTCG | GTTCAATATG | 480 |
| ACAGGACTAC | AACTAGATAA | GCCACAGCAA | TATAGTGAAA | CATGGTACTC | AAAGGATGTA | 540 |
| GTTTGTGACA | CAACTAATGG | GACCAGCCGC | AAATGTTACA | TGAACCATTG | CAACACATCA | 600 |
| GTCATCACAG | AGTCATGTGA | TAAGCACTAT | TGGGATGCTA | TGAGGTTTAG | ATACTGTGCA | 660 |
| CCACCGGGTT | TATGCTTGCT | AAGATGCAAT | GATACCAATT | ATTCAGGCTT | TGAGCCCAAG | 720 |
| TGTCCTAAAG | TAGTAGCTGC | TACATGCACA | AGAATGATGG | AAACGCAAAC | TTCTACTTGG | 780 |
| TTTGGCTTTA | ATGGCACTAG | GGCAGAAAAT | AGAACATATA | TCTATTGGCA | TGGTAGAGAT | 840 |
| AATAGGACTA | TTATCAGCTT | AAATACACAT | TATAATCTCA | CAATGCATTG | TAAGAGGCCA | 900 |
| GGAAATAAGT | CAGTTTTGCC | AATAACACTT | AGGTCAGGGA | GAGTGTTTCA | CTCCCGACCG | 960 |
| ATCATCAATG | AAAGACCCAA | GCAGGCATGG | TGCTGGTTCG | GAGGTGATTG | GAAGAAAGCC | 1020 |
| ATGCAGGAGG | TGAAACAAAC | CCTTGTGAAA | CATCCCAGGT | ATAGGGAAC | CAACGACACA | 1080 |
| CAGAAAATTA | ACTTTACACA | ACCAGGAAAA | GGTTCAGATG | CAGAAGTGGT | ATACATGTGG | 1140 |
| ACTAACTGCA | GAGGAGAATT | TCTATACTGC | AACATGACTC | GGTTCCTCAA | TTGGATAGAA | 1200 |
| AACAGGGCAC | ACCCACAGCG | CAATTATGCA | CCGTGCCATA | TAAGGCAAAT | AATTAATACC | 1260 |
| TGGCATAGAG | TAGGCCAAAA | TATATATTTG | CCTCCTAGGG | AAGGGGAATT | GGTCTGCAAC | 1320 |
| TCAACAGTAA | CCAGCATAAT | TGCTAACATT | GACATGTTTG | ATAACCAGAC | AAGCATTACC | 1380 |
| TTTAGTGCAG | AGGTGGCAGA | ACTATACCGA | TTGGAATTGG | GAGATTACAA | ATTAGTAGAA | 1440 |
| ATAACACCAA | TTGGCTTCGC | ACCTACATCA | GAAAAAAGGT | ATTCCTCTGC | TCCACAGAGG | 1500 |
| AATAAAAGAG | GTGTGTTTGT | GCTAGGAGTC | TTGGGTTTTC | TCGCAACAGC | AGGTTCTGCA | 1560 |

-continued

| ATGGGCGCGG | CGTCCTTGAC | GCTGTCGGCT | CATCCCGGAC | TTTACTGGGC | TGGGATAGTG | 1620 |
| CAGCAACAGC | AACAGCTGTT | GGACGTGGTC | AAGAGACAAC | AAGAAATGTT | GCGACTGACC | 1680 |
| GTCTGGGGAA | CAAAAAATCT | CCAGACAAGA | GTCACTGCTA | TCGAGAAATA | CCTAAGGGAC | 1740 |
| CAGGCGCGGC | TAAATTCATG | GGGATGTGCA | TTTAGACAAG | TCTGCTACAC | CACTGTACTA | 1800 |
| TGGGAAAATA | ACAGCATAGT | ACCTGATTGG | AACAACATGA | CGTGGCAGGA | ATGGGAACAA | 1860 |
| CAAACCCGCG | ACCTAGAGGC | AAATATCAGT | AGATCGTTAG | AGCAGGCACA | AATCCAACAA | 1920 |
| GAGAAAATA | TGTATGAGCT | ACAAAAATTA | AATAGCTGGG | ATGTTTTTGG | CAACTGGTTT | 1980 |
| GATTTAACCT | CCTGGATTAA | GTATATTCAG | TATGGAGTTT | ATGTAATAAT | AGGAATAATA | 2040 |
| GCTTTAAGAA | TAGTAATATA | TGTAGTACAA | TTACTAAGTA | GACTTAGAAA | GGGCTATAGG | 2100 |
| CCTGTTTTCT | CTTCCCCCCC | CGGTTATATC | AACAGATCC | ATATCCACAA | GGACTGGGAA | 2160 |
| CAGCCAGACA | GAGAAGAAAC | AGACGAAGAC | GCCGGAAACA | GCATTGGAGA | CAGCTCGTGG | 2220 |
| CCTTGGCCAA | TAGCATATAT | ACATTTCCTG | ATCCGCCAGC | TGATTCGCCT | CTTGACCGGG | 2280 |
| CTATACAGCG | TCTGCAAGGA | CTTACTATCC | AGGAGCTTCC | CGACCCTCCA | ACTAATCTTC | 2340 |
| CAGAGTCTTC | AGAGAGCACT | AACAACAATC | AGGGACTGGC | TGAGACTTAC | AATAGCCTAC | 2400 |
| CTGCAATATG | GGTGCGAGTG | GATCCAAGAA | GTGCTCCAGG | TCCTTGCAAG | GACTACGAGA | 2460 |
| GAGACTCTTG | CGAGCGCGTG | GAGAGACTTG | TGGGGGCAA | TGGGACGGAT | CGGCAGGGGA | 2520 |
| ATACTTGCAG | TTCCAAGAAG | GATCAGGCAG | GGGGCAGAAC | TTGCCCTCCT | GTGA | 2574 |

( 2 ) INFORMATION FOR SEQ ID NO:14:

( i ) SEQUENCE CHARACTERISTICS:
        ( A ) LENGTH: 3168 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: -
        ( B ) LOCATION: 1..3168
        ( D ) OTHER INFORMATION: /label=pol
            / note= "HIV-2KR subsequence encoding
            pol gene"

( x i ) SEQUENCE DESCRIPTION: SEQ ID NO:14:

| AAGACAGGGC | TGCTGGAAAT | GTGGCAAATC | AGGACATGTC | ATGGCAAACT | GCCCAGAAAG | 60 |
| ACAGGCTGGT | TTTTTAGGGA | TTGGCCCATG | GGGAAGAAG | CCTCGCAACT | TCCCCGTGAC | 120 |
| CCGAGTCCCG | CAGGGGCTGA | CACCAACAGC | ACCCCCAGCA | GACCCAGCAG | CAGACCTGCT | 180 |
| AGAGAAGTAC | TTGCAGCAAG | GGAGGAAGCA | GAAAGAGCAG | AAAATGAGAC | CATACAAGGA | 240 |
| GGTGACAGAG | GACTTACTGC | ACCTCGAACA | AGGAGAGACA | CCACACAAAG | AGGCGACAGA | 300 |
| GGATTTGCTG | CACCTCAATT | CTCTCTTTGG | AAAAGACCAG | TAGTCACAGC | ATATGTTGAG | 360 |
| GGTCAGCCAG | TAGAAGTCTT | ACTAGACACA | GGGGCTGACG | ACTCAATAGT | AGCAGGAATA | 420 |
| GAGTTGGGGA | GCAATTATAG | TCCAAAAATA | GTAGGGGAA | TAGGGGATT | CATAAACACC | 480 |
| AAGGAATATA | AAAATGTAGA | AATAAAGTA | CTAAATAAAA | AGGTAAAAGC | CACCATAATG | 540 |
| ACAGGTGATA | CCCCAATCAA | CATTTTTGGC | AGAAACATTC | TGACAGCCTT | AGGCATGTCA | 600 |
| TTAAATCTAC | CAGTCGCCAA | GGTAGACCCG | ATAAAGTAA | TACTGAAACC | AGGAAAAGAT | 660 |
| GGACCAAAAG | TAAGACAATG | GCCTCTAACA | AAAGAAAAGA | TAGAGGCACT | AAAAGAAATC | 720 |
| TGTGAAAAAA | TGGAAAGAGA | AGGCCAGCTA | GAGGAAGCTC | CCCCAACTAA | TCCTTATAAT | 780 |

```
ACCCCCACAT TTGCAATTAA GAAAAAGGAC AAAAACAAAT GGAGAATGCT AATAGATTTT     840
AGAGAACTAA ATAAGGTAAC TCAAGAGTTC ACAGAAATTC AGTTAGGAAT TCCACACCCA     900
GCAGGATTAG CCAAGAAAAG AAGAATTACT GTACTAGATA TAGGGGATGC CTACTTTTCC     960
ATACCACTAC ATGAGGACTT TAGACAATAT ACTGCATTTA CTCTACCAAC AGTGAACAAT    1020
GCAGAACCAG GAAAGAGATA TATATATAAA GTCCTACCAC AGGGATGGAA AGGATCGCCA    1080
GCAATTTTTC AACACACAAT GAGGCAGGTC TTAGAGCCAT TCAGAAAAGC AAACCCAGAC    1140
GTCATTCTCG TCCAATATAT GGATGATATC TTAATAGCTA GCGACAGGAC AGACTTAGAG    1200
CATGACAGAA CGGTCCTGCA GTTAAAAGAA CTTTTAAATG GCCTAGGATT CTCCACCCCA    1260
GATGAGAAGT TCCAAAAAGA CCCCCCATAC AAATGGATGG CTATGAACT  ATGGCCAACC    1320
AAATGGAAGC TGCAAAAAAT ACAATTGCCC CAAAAAGAAG TATGGACAGT CAATGACATC    1380
CAAAAGCTAG TAGGTGTCCT AAATTGGGCA GCACAAATCT ACCCAGGGAT AAAGACCAAA    1440
CACTTATGTA GGCTAATTAG AGGAAAAATG ACACTCACGG AAGAAGTACA GTGGACAGAA    1500
CTAGCAGAGG CAGAACTAGA AGAGAACAAA ATTATCTTGA GCCAGGAACA GGAGGGATGC    1560
TATTACCAAG AAGAAAAGGA ATTAGAAGCA ACAGTCCAAA AGGATCAAGA CAATCAGTGG    1620
ACATATAAAA TACACCAAGG AGAGAAAATC CTAAAAGTAG GAAAATATGC AAAGATAAAA    1680
AATACCCATA CCAATGGGGT CAGATTGTTA GCACATGTAG TTCAAAAAAT AGGAAAAGAA    1740
GCACTAGTCA TTTGGGGACG AATACCAAAA TTTCACCTAC CAGTAGAAAG AGAAACCTGG    1800
GAGCAGTGGT GGGATAACTA TTGGCAAGTG ACATGGATCC CAGACTGGGA CTTCGTATCT    1860
ACTCCACCAC TGGTCAGGTT AGCATTTAAC CTAGTAAAAG ATCCCATACC AGGTGAAGAG    1920
ACCTTCTACA CAGATGGATC CTGTAATAGG CAATCAAAAG AGGGAAAAGC AGGATATATA    1980
ACAGATAGAG GGAGAGACAA GGTAAGGATA TTGGAGCAAA CTACCAATCA GCAAGCAGAA    2040
TTAGAAGCCT TCGCAATGGC ATTAACAGAC TCAGGTCCAA AAGCCAATAT TATAGTAGAC    2100
TCACAGTATG TAATGGGAAT AGTAGCGGGC CAGCCAACAG AATCAGAGAG TAAACTAGTA    2160
AACCAAATCA TAGAAGAAAT GATAAAAAAG GAAACACTCT ATGTTGCATG GGTCCCAGCC    2220
CACAAAGGCA TAGGAGGAAA TCAGGAAGTA GATCATTTAG TAAGTCAGGG CATTAGACAA    2280
GTATTATTCC TAGAAAAAAT AGAGCCCGCT CAGGAAGAAC ATGAGAAATA TCATAGCAAT    2340
GTAAAAGAAT TATCCCATAA ATTTGGACTG CCCAAACTAG TGGCAAGACA AATAGTAAAC    2400
ACATGTGCCC AATGTCAACA GAAAGGGGAA GCTATACATG GGCAAGTAGA TGCAGAACTG    2460
GGCACTTGGC AAATGGACTG CACACACTTA GAGGGAAAAA TCATTATAGT AGCAGTACAT    2520
GTTGCAAGCG GGTTTATAGA AGCAGAAGTT ATCCACAGG  AAACGGGAAG GCAAACAGCA    2580
CTCTTCCTAT TAAAACTGGC CAGTAGGTGG CCAATAACAC ACCTGCACAC AGATAATGGT    2640
GCCAACTTCA CCTCACAGGA AGTAAAGATG GTAGCGTGGT GGACAGGTAT AGAACAATCC    2700
TTTGGAGTAC CTTACAATCC ACAAAGCCAA GGAGTAGTAG AAGCAATGAA TCACCACTTA    2760
AAAACCAGA  TAAGCAGAAT TAGAGAGCAG GCAAATACAA TGGAAACAAT AGTATTAATG    2820
GCAGTTCATT GCATGAATTT TAAAAGAAGG GGAGGAATAG GGATATGAC  CCCAGCAGAA    2880
AGACTAATCA ATATGATCAC CACAGAACAA GAAATACAAT TCCTCCACGC AAAAAATTCA    2940
AAATTAAAAA ATTTCCGGGT CTATTTCAGA GAAGGCAGAG ATCAGCTGTG GAAAGGACCT    3000
GGGGAACTAC TGTGGAAGGG AGATGGAGCA GTCATAGTCA AGGTAGGGAC AGACATAAAA    3060
ATAGTGCCAA GAAGGAAAGC TAAGATCATC AGAGACTATG GAGGAAGGCG AGAGGTGGAT    3120
AGTAGTTCCC ACTTGGAGGG TACCAGGGAG GATGGAGAAG TGGCATAG              3168
```

(2) INFORMATION FOR SEQ ID NO:15:

(i) SEQUENCE CHARACTERISTICS:
        (A) LENGTH: 531 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..531
        (D) OTHER INFORMATION: /label=rev
            / note= "HIV-2KR subsequence encoding rev gene"

(xi) SEQUENCE DESCRIPTION: SEQ ID NO:15:

```
ATGAACGGAA GGGCAGACGA AGAAGGACTC CAAGGGCTCA TTCGTCTTCT GCATCAGACA    60
GATCCATATC CACAAGGACT GGGAACAGCC AGACAGAGAA GAAACAGACG AAGACGCCGG   120
AAACAGCATT GGAGACAGCT CGTGGCCTTG GCCAATAGCA TATATACATT TCCTGATCCG   180
CCAGCTGATT CGCCTCTTGA CCGGGCTATA CAGCGTCTGC AAGGACTTAC TATCCAGGAG   240
CTTCCCGACC CTCCAACTAA TCTTCCAGAG TCTTCAGAGA GCACTAACAA CAATCAGGGA   300
CTGGCTGAGA CTTACAATAG CCTACCTGCA ATATGGGTGC GAGTGGATCC AAGAAGTGCT   360
CCAGGTCCTT GCAAGGACTA CGAGAGAGAC TCTTGCGAGC GCGTGGAGAG ACTTGTGGGG   420
GGCAATGGGA CGGATCGGCA GGGGAATACT TGCAGTTCCA AGAAGGATCA GGCAGGGGGC   480
AGAACTTGCC CTCCTGTGAG GGGCAGCGGT ATCAACAGGG AGACTTTATG A            531
```

(2) INFORMATION FOR SEQ ID NO:16:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..78
        (D) OTHER INFORMATION: /label=rev1
            / note= "HIV-2KR subsequence encoding rev1 gene"

(xi) SEQUENCE DESCRIPTION: SEQ ID NO:16:

```
ATGAACGGAA GGGCAGACGA AGAAGGACTC CAAGGGCTCA TTCGTCTTCT GCATCAGACA    60
AGTGAGTATA ATGGATAG                                                  78
```

(2) INFORMATION FOR SEQ ID NO:17:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..27
        (D) OTHER INFORMATION: /note= "left primer for HIV-2KR 5' LTR"

(xi) SEQUENCE DESCRIPTION: SEQ ID NO:17:

GCAAGCTTGG GATGGGATGT ATTACAG                                               27

(2) INFORMATION FOR SEQ ID NO:18:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..28
        (D) OTHER INFORMATION: /note= "right primer for HIV-2KR 5' LTR (xi) SEQUENCE DESCRIPTION: SEQ ID NO:18:

CCAAGCTTCT GCTAGGTATT TTCCCGCT                                              28

(2) INFORMATION FOR SEQ ID NO:19:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..25
        (D) OTHER INFORMATION: /note= "GR72 (outside, left) primer for
            HIV-2KR env"

(xi) SEQUENCE DESCRIPTION: SEQ ID NO:19:

ATGTGGACTA ACTGCAGAGG AGAAT                                                 25

(2) INFORMATION FOR SEQ ID NO:20:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..25
        (D) OTHER INFORMATION: /note= "GR81 (outside, right) primer
            for HIV-2KR env"

(xi) SEQUENCE DESCRIPTION: SEQ ID NO:20:

ATCCAGGAGG TTAAATCAAA CCAGT                                                 25

(2) INFORMATION FOR SEQ ID NO:21:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..32
        (D) OTHER INFORMATION: /note= "GR7 (inside, left) primer for HIV-2KR env"

( x i ) SEQUENCE DESCRIPTION: SEQ ID NO:21:

GGGATCGATT GAAATAACAC CAATTGGCTT CG                    32

( 2 ) INFORMATION FOR SEQ ID NO:22:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: -
        ( B ) LOCATION: 1..32
        ( D ) OTHER INFORMATION: /note= "GR8 (inside, right) primer for HIV-2KR env"

( x i ) SEQUENCE DESCRIPTION: SEQ ID NO:22:

GGGATCGATC ATAGTACAGT GGTGTAGCAG AC                    32

( 2 ) INFORMATION FOR SEQ ID NO:23:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: -
        ( B ) LOCATION: 1..19
        ( D ) OTHER INFORMATION: /note= "NEF9216 (outside, left) primer for HIV-2KR nef"

( x i ) SEQUENCE DESCRIPTION: SEQ ID NO:23:

CCAGCTGATT CGCCTCTTG                                   19

( 2 ) INFORMATION FOR SEQ ID NO:24:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: -
        ( B ) LOCATION: 1..19
        ( D ) OTHER INFORMATION: /note= "NEF10018 (outside, right) primer for HIV-2KR nef"

( x i ) SEQUENCE DESCRIPTION: SEQ ID NO:24:

CCTTCTGGAA AGTCCCTGC                                   19

( 2 ) INFORMATION FOR SEQ ID NO:25:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: -
        ( B ) LOCATION: 1..25
        ( D ) OTHER INFORMATION: /note= "NEF253 (inside, left) primer
            for HIV-2KR nef"

( x i ) SEQUENCE DESCRIPTION: SEQ ID NO:25:

AACAAAATAT GGATGATGTA GATGC                                       25

( 2 ) INFORMATION FOR SEQ ID NO:26:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: -
        ( B ) LOCATION: 1..25
        ( D ) OTHER INFORMATION: /note= "NEF360 (inside, right) primer
            for HIV-2KR nef"

( x i ) SEQUENCE DESCRIPTION: SEQ ID NO:26:

TAGAAAATGT GATATATCTA CTGCC                                       25

( 2 ) INFORMATION FOR SEQ ID NO:27:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: -
        ( B ) LOCATION: 1..18
        ( D ) OTHER INFORMATION: /note= "target sequence in first exon
            of tar for GUX hammerhead ribozyme"

( i x ) FEATURE:
        ( A ) NAME/KEY: misc_feature
        ( B ) LOCATION: 7..9
        ( D ) OTHER INFORMATION: /note= "cleavage site in target
            sequence in first exon of tar for GUX hammerhead
            ribozyme"

( x i ) SEQUENCE DESCRIPTION: SEQ ID NO:27:

CAGGAAGTCA GCCTAAGA                                                      18

( 2 ) INFORMATION FOR SEQ ID NO:28:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( A ) NAME/KEY: misc_RNA
        ( B ) LOCATION: 1..40
        ( D ) OTHER INFORMATION: /note= "hammerhead ribozyme which
            cleaves GUX in the first exon of tar"

( x i ) SEQUENCE DESCRIPTION: SEQ ID NO:28:

UCUUAGGCUC UGAUGAGUCC GUGAGGACGA AGACUUCCUG                   40

(2) INFORMATION FOR SEQ ID NO:29:

(i) SEQUENCE CHARACTERISTICS:
    (A) LENGTH: 119 amino acids
    (B) TYPE: amino acid
    (C) STRANDEDNESS:
    (D) TOPOLOGY: linear (ii) MOLECULE TYPE: peptide (ix) FEATURE:
    (A) NAME/KEY: Peptide
    (B) LOCATION: 1..119
    (D) OTHER INFORMATION: /note= "HIV-2KR rev protein amino acid residues from positions 58 to 176"

(xi) SEQUENCE DESCRIPTION: SEQ ID NO:29:

```
Pro Asp Pro Pro Ala Asp Ser Pro Leu Asp Arg Ala Ile Gln Arg Leu
1               5                   10                  15

Gln Gly Leu Thr Ile Gln Glu Leu Pro Asp Pro Thr Asn Leu Pro
            20                  25                  30

Glu Ser Ser Glu Ser Thr Asn Asn Asn Gln Gly Leu Ala Glu Thr Tyr
            35                  40                  45

Asn Ser Leu Pro Ala Ile Trp Val Arg Val Asp Pro Arg Ser Ala Pro
    50                  55                  60

Gly Pro Cys Lys Asp Tyr Glu Arg Asp Ser Cys Glu Arg Val Glu Arg
65                  70                  75                  80

Leu Val Gly Gly Asn Gly Thr Asp Arg Gln Gly Asn Thr Cys Ser Ser
                85                  90                  95

Lys Lys Asp Gln Ala Gly Gly Arg Thr Cys Pro Pro Val Arg Gly Ser
                100                 105                 110

Gly Ile Asn Arg Glu Thr Leu
                115
```

(2) INFORMATION FOR SEQ ID NO:30:

(i) SEQUENCE CHARACTERISTICS:
    (A) LENGTH: 119 amino acids
    (B) TYPE: amino acid
    (C) STRANDEDNESS:
    (D) TOPOLOGY: linear (ii) MOLECULE TYPE: peptide (ix) FEATURE:
    (A) NAME/KEY: Peptide
    (B) LOCATION: 1..119
    (D) OTHER INFORMATION: /note= "HIV-2ISY rev protein amino acids homologous to HIV-2KR rev protein amino acid residues from positions 58 to 176"

(xi) SEQUENCE DESCRIPTION: SEQ ID NO:30:

```
Pro Asp Pro Pro Ala Asp Pro Pro Leu Asp Gln Thr Ile Gln Gln Leu
1               5                   10                  15

Gln Gly Leu Thr Ile Gln Thr Leu Pro Asp Pro Thr Thr Leu Pro
            20                  25                  30

Glu Ser Ser Glu Ser Thr Asn Asn Asn Gln Arg Leu Ala Glu Thr Gln
            35                  40                  45

Gly Ser Leu Pro Ala Val Trp Val Arg Val Asp Pro Arg Ser Val Pro
    50                  55                  60

Gly Pro Arg Glu Gly Tyr Lys Arg Asp Ser Tyr Glu Arg Gly Glu Glu
65                  70                  75                  80

Leu Val Gly Gly Ser Gly Thr Asn Arg Lys Gly Asp Thr Arg Ser Ser
                85                  90                  95
```

Thr Lys Asp Gln Ala Gly Ser Arg Asn Cys Pro Pro Val Arg Asp Arg
                100                     105                 110

Asp Ile Ser Lys Glu Thr Leu
            115

(2) INFORMATION FOR SEQ ID NO:31:

(i) SEQUENCE CHARACTERISTICS:
        (A) LENGTH: 68 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..68
        (D) OTHER INFORMATION: /note= "HIV-2EHO rev protein amino
            acids homologous to HIV-2KR rev protein amino
            acid residues from positions 58 to 160"

(xi) SEQUENCE DESCRIPTION: SEQ ID NO:31:

Pro Asn Pro Pro Thr Ser Thr Pro Thr Ala Gln Ala Ser Thr Cys Ile
1               5                   10                  15

Pro Pro Ile Trp Asp Gln Leu Val Pro Arg Ser Asn Pro Ser Ser Ser
            20                  25                  30

Gln Gly Tyr Gly Arg Asp Ser Cys Glu Arg Gly Glu Asp Leu Val Gly
        35                  40                  45

Gly Pro Gln Glu Ser Gly Arg Arg Asp His Cys His Pro Gln Glu Asp
    50                  55                  60

Arg Ala Arg Gly
65

(2) INFORMATION FOR SEQ ID NO:32:

(i) SEQUENCE CHARACTERISTICS:
        (A) LENGTH: 68 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..68
        (D) OTHER INFORMATION: /note= "HIV-2UC1 rev protein amino
            acids homologous to HIV-2KR rev protein amino
            acid residues from positions 58 to 160"

(xi) SEQUENCE DESCRIPTION: SEQ ID NO:32:

Pro Asn Pro Pro Thr Ser Thr Pro Thr Ala Gln Ala Phe Thr Cys Ile
1               5                   10                  15

Pro Pro Val Trp Asp Gln Leu Val Pro Arg Ser Asn Pro Ser Ser Asn
            20                  25                  30

Glu Gly Cys Glu Arg Asp Ser Cys Glu His Arg Lys Ser Pro Met Glu
        35                  40                  45

Ser Ser Gln Lys Asp Ser Gly Ser Asn His Arg Asp Pro Gln Glu Asp
    50                  55                  60

Gln Thr Arg Thr
65

(2) INFORMATION FOR SEQ ID NO:33:

( i ) SEQUENCE CHARACTERISTICS:
 ( A ) LENGTH: 40 amino acids
 ( B ) TYPE: amino acid
 ( C ) STRANDEDNESS:
 ( D ) TOPOLOGY: linear ( i i ) MOLECULE TYPE: peptide ( i x ) FEATURE:
 ( A ) NAME/KEY: Peptide
 ( B ) LOCATION: 1..40
 ( D ) OTHER INFORMATION: /note= "HIV-2ROD rev protein amino
  acids homologous to HIV-2KR rev protein amino
  acid residues from positions 58 to 104"

( x i ) SEQUENCE DESCRIPTION: SEQ ID NO:33:

| Pro | Asp | Pro | Pro | Ala | Asp | Ser | Pro | Leu | Asp | Gln | Thr | Ile | Gln | His | Leu |
|---|---|---|---|---|---|---|---|---|---|---|---|---|---|---|---|
| 1 | | | | 5 | | | | | 10 | | | | | 15 | |

| Gln | Gly | Leu | Thr | Ile | Gln | Glu | Leu | Pro | Asp | Pro | Pro | Thr | His | Leu | Pro |
|---|---|---|---|---|---|---|---|---|---|---|---|---|---|---|---|
| | | | 20 | | | | | 25 | | | | | 30 | | |

| Glu | Ser | Gln | Arg | Leu | Ala | Glu | Thr |
|---|---|---|---|---|---|---|---|
| | | 35 | | | | | 40 |

( 2 ) INFORMATION FOR SEQ ID NO:34:

( i ) SEQUENCE CHARACTERISTICS:
  ( A ) LENGTH: 43 amino acids
  ( B ) TYPE: amino acid
  ( C ) STRANDEDNESS:
  ( D ) TOPOLOGY: linear ( i i ) MOLECULE TYPE: peptide ( i x ) FEATURE:
  ( A ) NAME/KEY: Peptide
  ( B ) LOCATION: 1..43
  ( D ) OTHER INFORMATION: /note= "HIV-2BEN rev protein amino
   acids homologous to HIV-2KR rev protein amino
   acid residues from positions 58 to 104"

( x i ) SEQUENCE DESCRIPTION: SEQ ID NO:34:

| Pro | Asp | Pro | Pro | Thr | Asp | Ser | Pro | Leu | Asp | Arg | Ala | Ile | Gln | His | Leu |
|---|---|---|---|---|---|---|---|---|---|---|---|---|---|---|---|
| 1 | | | | 5 | | | | | 10 | | | | | 15 | |

| Gln | Arg | Leu | Thr | Ile | Gln | Glu | Leu | Pro | Asp | Pro | Pro | Thr | Asp | Leu | Pro |
|---|---|---|---|---|---|---|---|---|---|---|---|---|---|---|---|
| | | | 20 | | | | | 25 | | | | | 30 | | |

| Glu | Ser | Asn | Ser | Asn | Gln | Gly | Leu | Ala | Glu | Thr |
|---|---|---|---|---|---|---|---|---|---|---|
| | | 35 | | | | | 40 | | | |

( 2 ) INFORMATION FOR SEQ ID NO:35:

( i ) SEQUENCE CHARACTERISTICS:
  ( A ) LENGTH: 43 amino acids
  ( B ) TYPE: amino acid
  ( C ) STRANDEDNESS:
  ( D ) TOPOLOGY: linear ( i i ) MOLECULE TYPE: peptide ( i x ) FEATURE:
  ( A ) NAME/KEY: Peptide
  ( B ) LOCATION: 1..43
  ( D ) OTHER INFORMATION: /note= "HIV-2GH1 rev protein amino
   acids homologous to HIV-2KR rev protein amino
   acid residues from positions 58 to 104"

( x i ) SEQUENCE DESCRIPTION: SEQ ID NO:35:

| Pro | Asp | Pro | Pro | Thr | Asp | Ser | Pro | Leu | Asp | Arg | Ala | Ile | Gln | Asp | Leu |
|---|---|---|---|---|---|---|---|---|---|---|---|---|---|---|---|
| 1 | | | | 5 | | | | | 10 | | | | | 15 | |

| Gln | Arg | Leu | Thr | Ile | His | Glu | Leu | Pro | Asp | Pro | Pro | Thr | Asp | Leu | Pro |
|---|---|---|---|---|---|---|---|---|---|---|---|---|---|---|---|
| | | | 20 | | | | | 25 | | | | | 30 | | |

```
                 Glu  Ser  Asn  Ser  Asn  Gln  Gly  Leu  Ala  Glu  Thr
                                35                      40
```

( 2 ) INFORMATION FOR SEQ ID NO:36:

( i ) SEQUENCE CHARACTERISTICS:
        ( A ) LENGTH: 43 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Peptide
        ( B ) LOCATION: 1..43
        ( D ) OTHER INFORMATION: /note= "HIV-2D194 rev protein amino
               acids homologous to HIV-2KR rev protein
               amino acid residues from positions
               58 to 104"

( x i ) SEQUENCE DESCRIPTION: SEQ ID NO:36:

```
Pro  Asp  Pro  Pro  Thr  Asp  Ser  Pro  Leu  Asp  Arg  Ala  Ile  Gln  Gln  Leu
1                    5                        10                       15

Gln  Gly  Leu  Thr  Ile  Gln  Glu  Leu  Pro  Asp  Pro  Pro  Thr  Asp  Leu  Pro
               20                       25                       30

Glu  Ser  Asn  Ser  Asn  Gln  Gly  Leu  Ala  Glu  Thr
               35                      40
```

( 2 ) INFORMATION FOR SEQ ID NO:37:

( i ) SEQUENCE CHARACTERISTICS:
        ( A ) LENGTH: 47 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Peptide
        ( B ) LOCATION: 1..47
        ( D ) OTHER INFORMATION: /note= "HIV-2NIHZ rev protein amino
               acids homologous to HIV-2KR rev protein
               amino acid residues from positions
               58 to 104"

( x i ) SEQUENCE DESCRIPTION: SEQ ID NO:37:

```
Pro  Asp  Pro  Pro  Ala  Asp  Ser  Pro  Leu  Asp  Arg  Ala  Ile  Gln  His  Leu
1                    5                        10                       15

Gln  Gly  Leu  Thr  Ile  Gln  Asp  Leu  Pro  Asp  Pro  Pro  Thr  Asn  Leu  Pro
               20                       25                       30

Glu  Ser  Pro  Glu  Ser  Thr  Asn  Ser  Asn  Gln  Arg  Leu  Ala  Glu  Ala
               35                      40                       45
```

( 2 ) INFORMATION FOR SEQ ID NO:38:

( i ) SEQUENCE CHARACTERISTICS:
        ( A ) LENGTH: 47 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Peptide
        ( B ) LOCATION: 1..47
        ( D ) OTHER INFORMATION: /note= "HIV-2ST rev protein amino
               acids homologous to HIV-2KR rev protein amino acid residues from positions 58-104"

(xi) SEQUENCE DESCRIPTION: SEQ ID NO:38:

| Pro | Asp | Pro | Pro | Ala | Asp | Ser | Pro | Leu | Glu | Gln | Thr | Ile | Gln | His | Leu |
|---|---|---|---|---|---|---|---|---|---|---|---|---|---|---|---|
| 1 | | | | 5 | | | | | 10 | | | | | 15 | |
| Gln | Gly | Leu | Thr | Ile | Gln | Glu | Leu | Pro | Asp | Pro | Pro | Thr | Asn | Leu | Pro |
| | | | 20 | | | | | 25 | | | | | 30 | | |
| Glu | Ser | Ser | Glu | Ser | Ile | Asp | Ser | Ser | Gln | Arg | Leu | Ala | Glu | Ile | |
| | | 35 | | | | | 40 | | | | | 45 | | | |

(2) INFORMATION FOR SEQ ID NO:39:

(i) SEQUENCE CHARACTERISTICS:
    (A) LENGTH: 47 amino acids
    (B) TYPE: amino acid
    (C) STRANDEDNESS:
    (D) TOPOLOGY: linear (ii) MOLECULE TYPE: peptide (ix) FEATURE:
    (A) NAME/KEY: Peptide
    (B) LOCATION: 1..47
    (D) OTHER INFORMATION: /note= "SIVMM239 rev protein amino
        acids homologous to HIV-2KR rev protein amino
        acid residues from positions 58 to 104"

(xi) SEQUENCE DESCRIPTION: SEQ ID NO:39:

| Pro | Asp | Pro | Pro | Thr | Asp | Thr | Pro | Leu | Asp | Leu | Ala | Ile | Gln | Gln | Leu |
|---|---|---|---|---|---|---|---|---|---|---|---|---|---|---|---|
| 1 | | | | 5 | | | | | 10 | | | | | 15 | |
| Gln | Asn | Leu | Ala | Ile | Glu | Ser | Ile | Pro | Asp | Pro | Pro | Thr | Asn | Thr | Pro |
| | | | 20 | | | | | 25 | | | | | 30 | | |
| Glu | Ala | Leu | Cys | Asp | Pro | Thr | Glu | Asp | Ser | Arg | Ser | Pro | Gln | Asp | |
| | | 35 | | | | | 40 | | | | | 45 | | | |

(2) INFORMATION FOR SEQ ID NO:40:

(i) SEQUENCE CHARACTERISTICS:
    (A) LENGTH: 47 amino acids
    (B) TYPE: amino acid
    (C) STRANDEDNESS:
    (D) TOPOLOGY: linear (ii) MOLECULE TYPE: peptide (ix) FEATURE:
    (A) NAME/KEY: Peptide
    (B) LOCATION: 1..47
    (D) OTHER INFORMATION: /note= "SIVMM251 rev protein amino
        acids homologous to HIV-2KR rev protein amino
        acid residues from positions 58 to 104"

(xi) SEQUENCE DESCRIPTION: SEQ ID NO:40:

| Pro | Asp | Pro | Pro | Thr | Asp | Thr | Pro | Leu | Asp | Leu | Ala | Ile | Gln | Gln | Leu |
|---|---|---|---|---|---|---|---|---|---|---|---|---|---|---|---|
| 1 | | | | 5 | | | | | 10 | | | | | 15 | |
| Gln | Asn | Leu | Ala | Ile | Glu | Ser | Ile | Pro | Asp | Pro | Pro | Thr | Asn | Thr | Pro |
| | | | 20 | | | | | 25 | | | | | 30 | | |
| Glu | Ala | Leu | Cys | Asp | Pro | Thr | Lys | Gly | Ser | Arg | Ser | Pro | Gln | Asp | |
| | | 35 | | | | | 40 | | | | | 45 | | | |

(2) INFORMATION FOR SEQ ID NO:41:

(i) SEQUENCE CHARACTERISTICS:
    (A) LENGTH: 47 amino acids
    (B) TYPE: amino acid
    (C) STRANDEDNESS:
    (D) TOPOLOGY: linear ( i i ) MOLECULE TYPE: peptide ( i x ) FEATURE:
    ( A ) NAME/KEY: Peptide
    ( B ) LOCATION: 1..47
    ( D ) OTHER INFORMATION: /note= "SIVMNE rev protein amino acids
        homologous to HIV-2KR rev protein amino
        acid residues from positions 58 to 104"

( x i ) SEQUENCE DESCRIPTION: SEQ ID NO:41:

Pro Asp Pro Pro Thr Asn Thr Pro Leu Asp Leu Val Ile Gln Gln Leu
1               5                   10                  15

Gln Asn Leu Ala Ile Glu Ser Ile Pro Asp Pro Pro Thr Asn Ile Pro
            20                  25                  30

Glu Ile Leu His Asp Pro Thr Glu Asn Pro Arg Ser Pro Gln Asp
        35                  40                  45

( 2 ) INFORMATION FOR SEQ ID NO:42:

( i ) SEQUENCE CHARACTERISTICS:
        ( A ) LENGTH: 42 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Peptide
        ( B ) LOCATION: 1..42
        ( D ) OTHER INFORMATION: /note= "SIVSMMH4 rev protein amino
            acids homologous to HIV-2KR rev protein amino
            acid residues from positions 58 to 99"

( x i ) SEQUENCE DESCRIPTION: SEQ ID NO:42:

Pro Asp Pro Pro Val Asp Thr Pro Leu Asp Leu Ala Ile Gln Gln Leu
1               5                   10                  15

Gln Gly Leu Ala Ile Glu Glu Leu Pro Asp Pro Pro Thr Ser Ala Pro
            20                  25                  30

Glu Pro Leu Asn Asp Val Ala Lys Ser Pro
        35                  40

( 2 ) INFORMATION FOR SEQ ID NO:43:

( i ) SEQUENCE CHARACTERISTICS:
        ( A ) LENGTH: 107 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: -
        ( B ) LOCATION: 1..107
        ( D ) OTHER INFORMATION: /note= "HIV-2KR 5' LTR subsequence from
            positions 407 to 513"

( x i ) SEQUENCE DESCRIPTION: SEQ ID NO:43:

CAGGAAGTAG ATGATGAAAC TGCAGGGACT TTCCAGAAGG GGCTGTAACC AGGGGAGGGA    60

CGTGGGAGGA ACCGGTGGGG AACGCCCTCA TACTTCTGTA TAAATGT                107

( 2 ) INFORMATION FOR SEQ ID NO:44:

( i ) SEQUENCE CHARACTERISTICS:
        ( A ) LENGTH: 119 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
    ( A ) NAME/KEY: -
    ( B ) LOCATION: 1..119
    ( D ) OTHER INFORMATION: /note= "HIV-2ST 5' LTR subsequence
        homologous to HIV-2KR 5' LTR positions
        407 to 513"

( x i ) SEQUENCE DESCRIPTION: SEQ ID NO:44:

```
CAGGAAGTAA CTAACAGAAA ACAGCTGAGA CTGCAGGGAC TTTCCAGAAG GGGCTGTTAC      60
CAGGGGAGGG ACATGGGAGG AGCCGGTGGG GAACGCCCTC ATACTTTCTG TATAAATGT      119
```

( 2 ) INFORMATION FOR SEQ ID NO:45:

( i ) SEQUENCE CHARACTERISTICS:
        ( A ) LENGTH: 119 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
    ( A ) NAME/KEY: -
    ( B ) LOCATION: 1..119
    ( D ) OTHER INFORMATION: /note= "HIV-2BEN 5' LTR subsequence
        homologous to HIV-2KR 5' LTR positions
        407 to 513"

( x i ) SEQUENCE DESCRIPTION: SEQ ID NO:45:

```
CAGGAAGTAG CTACTAAGAA ACAGCTGAGG CTGCAGGGAC TTTCCAGAAG GGGCTGTAAC      60
CAAGGGAGGG ACATGGGAGG AGCTGGTGGG GAACGCCCTC ATACTTACTG TATAAATGT      119
```

( 2 ) INFORMATION FOR SEQ ID NO:46:

( i ) SEQUENCE CHARACTERISTICS:
        ( A ) LENGTH: 118 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
    ( A ) NAME/KEY: -
    ( B ) LOCATION: 1..118
    ( D ) OTHER INFORMATION: /note= "HIV-2D194 5' LTR subsequence
        homologous to HIV-2KR 5' LTR positions
        407 to 513"

( x i ) SEQUENCE DESCRIPTION: SEQ ID NO:46:

```
CAGGAAATAG CTACTAAGAA CAGCTGAGAC TGCAGGGACT TTCCAGAAGG GGCTGTAACC      60
AAGGGAGGGA CATGGGAGGA GCTGGTGGGG AACGCCCTCA TATTCTCTGT ATAAATGT       118
```

( 2 ) INFORMATION FOR SEQ ID NO:47:

( i ) SEQUENCE CHARACTERISTICS:
        ( A ) LENGTH: 118 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
    ( A ) NAME/KEY: -
    ( B ) LOCATION: 1..118
    ( D ) OTHER INFORMATION: /note= "HIV-2ISY 5' LTR subsequence
        homologous to HIV-2KR 5' LTR positions 407 to 513"

( x i ) SEQUENCE DESCRIPTION: SEQ ID NO:47:

```
CAGGAAGTAG CTACTGAAAA CAGCTGAGAC TGCAGGGACT TTCCAGAAGG GGCTGTAACC         60

AGGGGAGGGA CATGGGAGGA GCTGGTGGGG AACGCCCTCA TACTTTCTGT ATAAATGT         118
```

( 2 ) INFORMATION FOR SEQ ID NO:48:

( i ) SEQUENCE CHARACTERISTICS:
        ( A ) LENGTH: 118 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: -
        ( B ) LOCATION: 1..118
        ( D ) OTHER INFORMATION: /note= "HIV-2ROD 5' LTR subsequence
            homologous to HIV-2KR 5' LTR positions
            407 to 513"

( x i ) SEQUENCE DESCRIPTION: SEQ ID NO:48:

```
CAGGAAGTAA CTAACAGAAA CAGCTGAGAC TGCAGGGACT TTCCAGAAGG GGCTGTAACC         60

AAGGGAGGGA CATGGGAGGA GCTGGTGGGG AACGCCCTCA TATTCTCTGT ATAAATAT         118
```

( 2 ) INFORMATION FOR SEQ ID NO:49:

( i ) SEQUENCE CHARACTERISTICS:
        ( A ) LENGTH: 119 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: -
        ( B ) LOCATION: 1..119
        ( D ) OTHER INFORMATION: /note= "HIV-2NIHZ 5' LTR subsequence
            homologous to HIV-2KR 5' LTR positions
            407 to 513"

( x i ) SEQUENCE DESCRIPTION: SEQ ID NO:49:

```
CAGGAAGTAG CTACTGAGAA CAGCTGAGAC TGCAGGGACT TTCCAGAAGG GGCTGTAACC         60

AGGAGAGGGA CATGGGAGGA GCTGGTGGGG AACGCCCTTC ATACTTTCTG TATAAATGT         119
```

( 2 ) INFORMATION FOR SEQ ID NO:50:

( i ) SEQUENCE CHARACTERISTICS:
        ( A ) LENGTH: 119 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: -
        ( B ) LOCATION: 1..119
        ( D ) OTHER INFORMATION: /note= "Consensus HIV-2 5' LTR
            subsequence homologous to HIV-2KR 5' LTR
            positions 407 to 513"

( x i ) SEQUENCE DESCRIPTION: SEQ ID NO:50:

```
CAGGAAGTAG CTACTAAGAA ACAGCTGAGA CTGCAGGGAC TTTCCAGAAG GGGCTGTAAC         60

CAGGGGAGGG ACATGGGAGG AGCTGGTGGG GAACGCCCTC ATACTTTCTG TATAAATGT         119
```

ISOLATION OF NOVEL HIV-2 PROVIRUSES

CROSS REFERENCE TO RELATED APPLICATIONS

This application is a continuation-in-part of U.S. provisional application U.S. Ser. No. 60/001,441 (Kraus et al.) filed Jul. 26, 1995.

BACKGROUND OF THE INVENTION

Human immunodeficiency virus (HIV) type 1 (HIV-1) and HIV type 2 (HIV-2) are genetically related, antigenically cross reactive, and share a common cellular receptor (CD4). See, Rosenburg and Fauci (1993) in *Fundamental Immunology*, Third Edition Paul (ed) Raven Press, Ltd., New York (Rosenburg and Fauci 1) and the references therein for an overview of HIV infection. HIV-1 infection is epidemic world wide, causing a variety of immune system-failure related phenomena commonly termed acquired immune deficiency syndrome (AIDS). HIV type 2 (HIV-2) has been isolated from both healthy individuals and patients with AIDS-like illnesses (Andreasson, et al. (1993) *Aids* 7, 989–93; Clavel, et al. (1986) *Nature*, 324, 691–695; Gao, et al. (1992) *Nature* 358, 495–9; Harrison, et al. (1991) *Journal of Acquired Immune Deficiency Syndromes* 4, 1155–60; Kanki, et al. (1992) *American Journal of Epidemiology* 136, 895–907; Kanki, et al. (1991) *Aids Clinical Review* 1991, 17–38; Romieu, et al. (1990) *Journal of Acquired Immune Deficiency Syndromes* 3, 220–30; Naucler, et al. (1993) *International Journal of SYD and Aids* 4, 217–21; Naucler, et al. (1991) *Aids* 5, 301–4). Although HIV-2 AIDS cases have been identified principally from West Africa, sporadic HIV-2 related AIDS cases have also been reported in the United States (O'Brien, et al. (1991) *Aids* 5, 85–8) and elsewhere. HIV-2 will likely become endemic in other regions over time, following routes of transmission similar to HIV-1 (Harrison, et al. (1991) *Journal of Acquired Immune Deficiency Syndromes* 4, 1155–60; Kanki, et al. (1992) *American Journal of Epidemiology* 136, 895–907; Romieu, et al. (1990) *Journal of Acquired Immune Deficiency Syndromes* 3, 220–30). Epidemiological studies suggest that HIV-2 produces human disease with lesser penetrance than HIV-1, and exhibits a considerably longer period of clinical latency (at least 25 years, and possibly longer, as opposed to less than a decade for HIV-1; see, Kanki, et al. (1991) *Aids Clinical Review* 1991, 17–38; Romieu, et al. (1990) *Journal of Acquired Immune Deficiency Syndromes* 3, 220–30, and Travers et al. (1995) *Science* 268: 1612–1615).

The molecular receptor for HIV is the surface glycoprotein CD4 found mainly on a subset of T cells, monocytes, macrophage and some brain cells. HIV has a lipid envelope with viral antigens that bind the CD4 receptor, causing fusion of the viral membrane and the target cell membrane and release of the HIV capsid into the cytosol. HIV causes death of these immune cells, thereby disabling the immune system and eventually causing death of the patient due to complications associated with a disabled immune system. HIV infection also spreads directly from cell to cell, without an intermediate viral stage. During cell-cell transfer of HIV, a large amount of viral glycoprotein is expressed on the surface of an infected cell, which binds CD4 receptors on uninfected cells, causing cellular fusion. This typically produces an abnormal multinucleate syncytial cell in which HIV is replicated and normal cell functions are suppressed.

Molecular analysis suggests that HIV-2 is more stable than HIV-1 in the human population, implying milder pathogenicity of the virus and introduction into the human population at a time earlier than HIV-1 (Clavel, et al. (1986) *Nature*, 324, 691–695; Gao, et al. (1992) *Nature* 358, 495–9; Naucler, et al. (1991) *Aids* 5, 301–4; O'Brien, et al. (1991) *Aids* 5, 85–8; Castro, et al (1990) *Virology* 178, 527–34; Kirchhoff, et al. (1990) *Aids* 4, 847–57; Kuhnel, et al. (1989) *Proc. Natl. Acad. Sci. U.S.A.* 86, 2383–2387; Kumar, et al. (1990) *Journal of Virology* 64, 890–901; Zagury, et al. (1988) *Proc. Natl. Acad. Sci. U.S.A.* 85, 5941–5945; Franchini, et al. (1989) *Proc. Natl. Acad. Sci. U.S.A.* 86, 2433–2437). Overlap of HIV-2 sequences with those of related simian immunodeficiency virus (SIV) isolates also provides evidence indicating that HIV-2 infection of humans originated through introduction of these primate lentiviruses through environmental or occupational (e.g., hunting, or cooking) exposure (Gao, et al (1992) *Nature* 358, 495–9).

Several HIV-2 isolates, including three molecular clones of HIV-2$_{ROD}$, HIV-2$_{SBL-ISY}$, and HIV-2$_{UCI}$, have been reported to infect macaques (*M. mulatta* and *M. nemestrina*) or baboons (Franchini, et al. (1989) *Proc. Natl. Acad. Sci. U.S.A.* 86, 2433–2437; Barnett, et al. (1993) *Journal of Virology* 67, 1006–14; Boeri, et al. (1992) *Journal of Virology* 66, 4546–50; Castro, et al. (1991) *Virology* 184, 219–26; Franchini, et al. (1990) *Journal of Virology* 64, 4462–7; Putkonen, et al. (1990) *Aids* 4, 783–9; Putkonen, et al. (1991) *Nature* 352, 436–8). As human pathogens capable of infection of small primates, HIV-2 molecular clones provide attractive models for studies of AIDS pathogenesis, and for drug and vaccine development against HIV-1 and HIV-2.

Recently, HIV-2 was suggested as a possible vaccine candidate against the more virulent HIV-1 due to its long asymptomatic latency period, and its ability to protect against infection by HIV-1 (see, Travers et al. (1995) *Science* 268: 1612–1615 and related commentary by Cohen et al (1995) *Science* 268:1566). In the nine-year study by Travers et al. (id) of West African prostitutes infected with HIV-2 it was determined that infection with HIV-2 caused a 70% reduction in infection by HIV-1.

One notable characteristic of most HIV-2 isolates, in contrast to HIV-1, is their ability to readily infect primary monocyte-macrophages even after extensive passage on T-cell lines (Franchini, et al. (1989) *Proc. Natl. Acad. Sci. U.S.A.* 86, 2433–2437; Barnett, et al. (1993) *Journal of Virology* 67, 1006–14; Boeri, et al. (1992) *Journal of Virology* 66, 4546–50; Castro, et al. (1991) *Virology* 184, 219–26; Franchini, et al. (1990) *Journal of Virology* 64, 4462–7; Putkonen, et al. (1990) *Aids* 4, 783–9; Putkonen, et al. (1991) *Nature* 352, 436–81; Hattori, et al. (1990) *Proc. Natl. Acad. Sci. U.S.A.* 87, 8080–4). HIV-2, like SIV, encodes a vpx gene (Kappes, et al. (1991) *Virology* 184, 197–209; Marcon, et al. (1991) *Journal of Virology* 65, 3938–42), but lacks the vpu gene found in HIV-1. A consequence of the absence of vpu is that the HIV-2 envelope is not expressed as a bicistronic message. Other differences between HIV-1 and HIV-2 include differential sensitivity to non-nucleoside reverse transcriptase inhibitors (Bacolla, et al. (1993) *Journal of Biological Chemistry* 268, 16571–7), the variability and importance of the V3 region of envelope in neutralization (Bjorling, et al. (1994) *Journal of Immunology* 152, 1952–9; Chiodi, et al. (1993) *Chemical Immunology* 56, 61–77), the involvement of different transcriptional factors and T-cell signaling pathways in activation of the viral LTR (Hannibal, et al. (1993) *Journal of Virology* 67, 5035–40), and the specificity of the Tat and Rev transactivating proteins (Fenrick, et al. (1989) *Journal of Virology* 63, 5006–12; Malim, et al. (1989) *Proc. Natl. Acad. Sci. U.S.A.* 86, 8222–6).

The capacity to infect quiescent cells, which is not shared by oncoretroviruses or MoMLV-derived retroviral vectors, has spurred efforts to develop HIV-based gene therapy vectors. The goal of HIV-based vectors is stable transfer of genes to rarely dividing stem cells and post-mitotic cells in the hematopoietic, nervous, and other body systems. Progress has been made recently with vesicular stomatitis virus envelope glycoprotein (VSV-G)-pseudotyped HIV-1 vectors in this regard (Naldini et al. (1996) *Science* 272:263). Although high titers in the $10^5$ range were achieved, this system relies upon transient transfection to generate vector supernatants. Stable packaging cell lines were not developed. In addition, the vector is derived from HIV-1, a lentivirus with nearly uniform lethality in humans.

Other HIV vector systems have been studied. See, Akidna et al. (1996) *J Virol* 70:2581; Poznansky et al. (1991) *J Virol* 65:532; Parolin et al. (1994) *Journal of Virology* 68:3888; Richardson et al. (1995) *Journal of General Virology* 76:691; Buchschacher et al. (1992) *Journal of Virology* 66:2731; and Marlink et al. (1994) *Science* 265:1587. However, all are derived from HIV-1 and all evince a variety of limitations. Several use wild-type replication competent virus as the source of packaging proteins, and some represent simple pseudotyping of an env gene-mutated full-length provirus by VSV-G (i.e., no packaging construct, lines or vector lacking other structural genes). In general, two problems have been most prominent in this field: (1) titers, with the exception of Naldini et al. (1996; supra), have been exceedingly low ($10^1$–$10^2$) (Poznansky, 1991 and Parolin, 1994, supra) or not reported (Adkina, 1996, supra) and (2) stable packaging lines have not been developed.

Accordingly, the isolation and development of non-pathogenic strains of HIV-2 as vaccines, in vitro diagnostic reagents, cell transduction and gene therapy vectors, and HIV-2 based packaging cell lines is needed. The present invention fulfills these and other needs.

SUMMARY

The molecular and biological properties of a full-length biologically active HIV-2 clone which is infectious for *M. nemestrina* are described. The clone causes asymptomatic infection, and protects against infection with more pathogenic strains of HIV. In addition, the clone provides a ready source of nucleic acid for the production of HIV-2 polypeptides and other immunogenic reagents, e.g., through cloning and expression of the relevant genes. In addition, the clone possesses many features which make it ideal for incorporation into gene therapy vectors, e.g., for the treatment and prevention of HIV infections, and more generally, as a source of components of retroviral vectors. For instance, HIV-$2_{KR}$ has a strong basal promoter, removing the requirement for tat and rev transactivation. Thus, retroviral vectors with the HIV-$2_{KR}$ LTRs do not require tat or rev for transactivation. Furthermore, HIV-2, and HIV-$2_{KR}$ in particular is useful for establishing HIV packaging cell lines, e.g., for use in retroviral vector construction.

The present invention provides an isolated HIV-2 provirus with a full-length HIV-2 genome. The rev gene encoded by the provirus typically hybridizes to the second exon of the HIV-$2_{KR}$ rev gene under stringent conditions, or more preferably under highly stringent conditions. In addition, the proviral HIV-2 LTR has an activating deletion, resulting in high basal activity. The rev gene is a particularly applicable marker for detecting full-length proviruses of the present invention because the second exon of the provirus encodes amino acid residues not found in other known HIV-2 proviruses. Similarly, the activating deletion in the LTR of the proviruses of this invention does not exist in other known HIV-2 strains.

The HIV-2 proviruses of the invention exist as free nucleic acids (RNA or DNA), as a portion of a nucleic acid (e.g., incorporated into a nucleic acid vector (plasmid, virus, etc.), or cellular genome), or as a protein-nucleic acid complex (e.g., encapsidated in a retroviral viral particle such as an HIV-2 capsid/envelope, or as part of a cellular chromosome or episome). Because the proviruses of the invention are amphotropic (i.e., able to grow in multiple cell types outside of the host range of HIV), the proviruses of the invention exist in a variety of cell types (e.g., during replication), including human cells, *M. nemistrtina* cells and murine cells. The amphotropic nature of the provirus makes it a suitable gene therapy vector, and suitable for the production of HIV packaging cell lines.

The HIV-2 proviruses of the present invention are also amenable to cloning and subcloning. Accordingly, the provirus and regions of interest (i.e., nucleic acids encoding HIV-2 polypeptides and cis-active HIV-2 nucleic acids such as the 5' and 3' LTR regions, the MSD and the psi site) are optionally cloned or subcloned into known vectors. Thus, the HIV-2 provirus is optionally cloned or sub-cloned to produce a viral particle (e.g., a bacculovirus, pox virus, Adeno-associated virus or a retrovirus), a plasmid, a recombinant cell, a plant, or an animal (e.g., an insect, or a mammal).

In one preferred embodiment, the HIV-2 provirus of the invention has the nucleic acid sequence described in SEQ ID No: 1 (the full-length HIV-$2_{KR}$ proviral nucleic acid sequence). One of skill will appreciate that many variations of SEQ ID No: 1 yield an essentially identical virus. For example, due to the degeneracy of the genetic code, "silent substitutions" are an implied feature of every nucleic acid sequence which encodes an amino acid. Similarly, "conservative amino acid substitutions," in one or a few amino acids in an amino acid sequence are substituted with different amino acids with highly similar properties, are also readily identified as being highly similar to a particular amino acid sequence, or to a particular nucleic acid sequence which encodes an amino acid. Such conservatively substituted variations of a disclosed sequence are also a feature of the present invention.

Subsequences of the HIV-$2_{KR}$ provirus such as the HIV-$2_{KR}$ 3' LTR, the HIV-$2_{KR}$ 5' LTR, the HIV-$2_{KR}$ env gene, the HIV-$2_{KR}$ nef gene, the HIV-$2_{KR}$ rev gene, the HIV-$2_{KR}$ vpx gene, the HIV-$2_{KR}$ tat gene, the HIV-$2_{KR}$ gag gene, the HIV-$2_{KR}$ pol gene, the HIV-$2_{KR}$ vif gene, and the HIV-$2_{KR}$ vpr gene are also a feature of the present invention. Any unique region of HIV-$2_{KR}$ nucleic acid is useful as a molecular probe to identify the HIV-$2_{KR}$ provirus, and to distinguish the provirus from other known strains of HIV-2. Unique HIV-$2_{KR}$ region are found by comparing HIV-$2_{KR}$ nucleic acid sequences to other known HIV-2 clones and virus sequences, such as HIV-$2_{NIHZ}$. Typically, HIV-$2_{KR}$ is about 80–90% identical to other known strains of HIV-2. Thus, comparison windows of 50, 60, 70, 80 and 90 nucleic acids reveal that no known strain of HIV-2 is completely identical to HIV-$2_{KR}$ over a contiguous region of nucleic acid the size of the comparison window. Therefore, all contiguous nucleic acids of at least about 50 nucleic acids, and more preferably 60 nucleic acids, and still more preferably 70 nucleic acids, typically 80 nucleic acids and most typically 90 nucleic acids from the HIV-$2_{KR}$ sequence described in SEQ ID NO: 1 are novel and useful, e.g., as molecular probes to detect HIV-$2_{KR}$, in biological samples.

Polypeptides and nucleic acids encoded by the HIV-2$_{KR}$ and other proviruses of the present invention are valuable for a variety of purposes, including as immunogens to generate antibodies against HIV viruses (e.g., HIV-1 and HIV-2), as vaccines and other therapeutic compositions, as components of HIV packaging cells, as components of viral complementation assays, as diagnostic reagents for the diagnosis and monitoring of HIV infections, and as components of gene therapy vectors. When administered in a therapeutically effective amount to a mammal, the provirus of the present invention confers resistance to subsequent HIV infections.

In a preferred embodiment, the HIV-2 provirus of the invention comprises a full-length HIV-2 genome and has the following characteristics. The provirus when encapsidated in an HIV viral particle encoded by the provirus, is replication competent in vitro in Molt-4/8 cells; the provirus is infectious in primary human and macaque lymphocytes when encapsidated in an HIV viral particle; the provirus, when encapsidated in an HIV viral particle encoded by the provirus, has reduced infectivity for macaque peripheral blood mononuclear cells compared to HIV-$2_{NIHZ}$ and HIV-$2_{rod}$; the provirus, when encapsitated in an HIV viral particle encoded by the provirus, produces an attenuated infection in *M. nemestrina*; the provirus, when encapsitated in an HIV viral particle encoded by the provirus, produces an infection in Hu-PBL-SCID mice; the second exon of the rev gene encoded by the provirus encodes an amino acid sequence 180 amino acids in length; the proviral LTR has an activating deletion; and, the proviral LTR has high basal activity.

The invention provides high efficiency packaging vectors, packaging cells which express the vectors and nucleic acids which are packaged by the vectors. The high efficiency HIV-2 packaging vectors have a first high efficiency packaging vector nucleic acid, which encodes a first portion of an HIV-2 particle. The particle packages HIV-2 packagable nucleic acids (e.g., a nucleic acid encoding an HIV-2 packaging site). To increase safety, high efficiency packaging vectors are optionally present as multiple complementary nucleic acids, each of which encodes only a portion of the genes necessary for HIV packaging. When the complementary nucleic acids are co-expressed in a cell they provide all of the trans-active factors necessary for HIV packaging. Thus, in one embodiment, the present invention provides a first high efficiency packaging vector nucleic acid, a second high efficiency vector nucleic acid, a third high efficiency vector nucleic acid, and so on.

The high efficiency packaging vector nucleic acid lacks cis active sequences (e.g., the HIV-2 psi site) necessary for packaging the nucleic acid into an HIV viral particle; thus, the encoded HIV-2 particle is itself non-virulent (not capable of a productive infection which produces progeny virus; i.e., the particle is not replicative in the absence of a source of complementary viral components). The high efficiency packaging vector nucleic acid, when transfected into a population of cells, renders the cells competent to package HIV-2 packagable RNA with a cell supernatant titre of at least $1\times10^3$ transducing units per ml, and preferably $1\times10^4$ transducing units per ml. The HIV-2 packagable RNA comprises an HIV packaging site. Example high efficiency packaging nucleic acids include the plasmids pEP32, pEP40, pEP41, pEP42, and pEP43.

The HIV-2 packaging cell lines express the high efficiency packaging vectors of the invention. In one class of embodiments, the host range of viral particles produced by the packaging cell is modified by pseudotyping the vector by expressing the vesicular stomatitis virus envelope glycoprotein in the cell.

HIV-2 particles produced by the packaging cells of the invention typically include an HIV-2 packagable RNA which has the cis-active sequences necessary for packaging, but which lacks sequences encoding trans active HIV sequences which provide the structural components of the viral particle. A preferred the HIV-2 packaging site is derived from HIV-$2_{KR}$. Because the packaged nucleic acid does not comprise sequences necessary for HIV particle formation, the particle is non-virulent. Deletion of portions of complete HIV-2 genes from HIV-2 packagable nucleic acids can include deletion of some, or all of the genes for gag, pol, vif, vpx, vpr, env, rev, tat, and nef. The HIV-2 particles optionally comprise VSV-G envelope protein, which expands the infective range of the particle (e.g., to CD34 stem cells).

In one class of embodiments, the packagable nucleic acid further comprises an HIV-2 LTR, p17 subsequence, and HIV-2 RRE subsequence. These sequences aid in packaging, processing and integration of the packagable nucleic acid in a target cell (e.g., a $CD4^+$ or $CD34^+$ cell).

The packagable nucleic acids of the invention optionally include marker genes which encode detectable markers. The inclusion of detectable markers provides a means of monitoring the infection and stable transduction of target cells. Markers include components of the beta-galactosidase gene and nucleic acid subsequences encoding the green fluorescence protein.

BRIEF DESCRIPTION OF THE DRAWINGS

FIG. 1 provides a genetic analysis of HIV-$2_{KR}$. [A] Open reading frame analysis of HIV-$2_{KR}$ produced from complete nucleotide sequence data obtained from double-stranded sequencing of the lambda proviral clone. Note the presence of long rev reading frame overlapping a substantial portion of nef, detailed in the alignment below, the presence of full length env (no truncation in transmembrane protein) and nef reading frames, and typical organization of vif, vpr, vpx, and other frames, all full-length and open. The predicted amino acid sequence of HIV-$2_{KR}$ REV protein and those of previously sequenced HIV-2 and SIV clones (Los Alamos database) were aligned and edited to show identity with the HIV-$2_{KR}$ sequence (SEQ ID NOs: 29–42) as [.], gaps as [–], and differences as the differing residue. Note that the HIV-$2_{KR}$ sequence extends for nearly 69 residues past the end of most other HIV-2 and SIV rev protein sequences. [B] Homology of HIV-$2_{KR}$ with other HIV-2 and SIV viruses was calculated for the gag, pot, tat, rev, vif, vpr, vpx, env, and nef genes, using a hierarchical multiple alignment scoring program to obtain similarity scores (Maximum Match=17, Minimum Gap=3, Mismatch=–8, Gap-Open Penalty=8, Gap-Extension Penalty=3). [C] Using Neighbor-Joining analysis to construct an unrooted Phylogenetic tree, HIV-$2_{KR}$ grouped closely with all other previously sequenced HIV-2 clones, except for HIV-$2_{UCl}$, and HIV-$2_{EHO}$, which grouped more closely with $SIV_{AGM}$.

FIG. 2 shows the high basal activity of the HIV-$2_{KR}$ LTR. [A] Alignments (SEQ ID NOs: 43–50) were performed as in FIG. 1A and FIG. 1B. Predicted nuclear factor binding sites (TFD Data Base, David Gosh) are shown in the top portion of this figure. Note the gap at position 429–430 in KR compared to other HIV-2 LTR sequences, suspected to be responsible for the increased basal activity. [B] Basal and stimulated activity of the HIV-$2_{KR}$, HIV-$2_{ST}$, and HIV-$1_{IIIB}$ LTR promoters in U937 cells. CAT indicator plasmids were constructed as indicated in the Materials and Methods section of the Examples. For the assay, 5 mg of the different LTR-CAT constructs were transfected into 1.5×10⁶ U937 cells using the cationic lipid technique (DoTAP™). Transfected cells were stimulated 20 hours later with either PHA (2 mg/ml) or GM-CSF (8 ng/ml), and incubated overnight. After harvesting the cells and extracting the cell lysate (See, Methods and Materials for Example 1), chloramphenicol transferase activity was quantitated using a commercial CAT-ELISA kit (Promega).

FIG. 3 shows the Kinetics of Macrophage Infection by HIV-2$_{KR}$. Replication kinetics of HIV-2$_{KR}$ in human peripheral blood derived monocyte-macrophages were compared with those of other HIV-2 isolates and clones. Macrophages obtained from PBMC from normal donors were obtained by adherence onto fibronectin coated flasks, and cultured in the presence of 10% endothelial conditioned medium (containing M-CSF), 10% human serum, and 10% fetal calf serum (see, Materials and Methods from Example 1). Infection of 1000×TCID$_{50}$ of HIV-2$_{KR}$, HIV-2$_{ROD}$, or HIV-2$_{NIHz}$ was performed after treatment of cells with polybrene (8 mg/ml) for 30 minutes at 37° C. Cells were washed extensively with Hanks balanced salt solution after 3 hours of incubation with virus in media. Coulter SIV p26 EIA was used to quantify virus production at intervals after infection. Note the prompt rise in p26 production by HIV-2$_{KR}$ infected monocytes, sustained over several weeks in culture. WPI-Weeks Post Infection. The zero timepoint was obtained after extensive washing following initial infection (a 24 hour time point was also obtained and was comparable).

FIG. 4 shows the cytopathic effects of HIV-2$_{KR}$ in vitro. The cytopathic effects of HIV-2$_{KR}$ infection in on monocytes and lymphoblastoid cells were compared. Infection of lymphoblastoid Molt-4/Clone 8 cells [A,C,E] and primary human monocyte macrophages [B,D,F] with HIV-2$_{KR}$ [A,B], HIV-2$_{ROD}$ [C,D], and HIV-1 [E,F]. Approximately [A] Molt4/Clone 8 cells 5 days post-infection with 100× TCID$_{50}$ of HIV-2KR, [B] Monocytes 6 weeks after infection with 100×TCID$_{50}$ HIV-2$_{KR}$, [C] Molt4/Clone 8 cells 5 days post-infection with 100×TCID$_{50}$ HIV-2$_{ROD}$, [D] Monocytes 6 weeks after infection with an equivalent dose of HIV-²$_{ROD}$, [E] Molt-4/Clone 8 cells 5 days post-infection with 100× TCID$_{50}$ HIV-1$_{MN}$, and [F] Monocytes 6 weeks after infection with an equivalent infectious dose of HIV-1$_{IIIB}$. Note the distinct contrast between HIV-2$_{KR}$ and HIV-2$_{ROD}$ in antigen production (FIG. 3) and production of multinucleate giant cells in infected monocyte-macrophage cultures.

FIG. 10 shows viral antigen expression by G418-selected cell lines.

FIG. 11 shows G418 stable viral producer and packaging cell lines, including viral antigen production. Stable cell lines were derived by selection and maintenance in G418 600 μg/ml after transfection of CsCl-purified plasmid DNA previously linearized in prokaryotic sequences. Adherent cell lines were derived using polybrene-DMSO transfection and suspension cell lines by lipofection. Single cell clones were obtained from 96-well plates seeded with limiting dilutions of cells resulting in less than 12 clones per plate. Viral titrations were carried out by end-point dilution infection of Molt4 clone 8 T cells in 96-well plates scored for syncytia at 10 days. p26 was assayed by the Coulter antigen capture kit.

Figure 12:
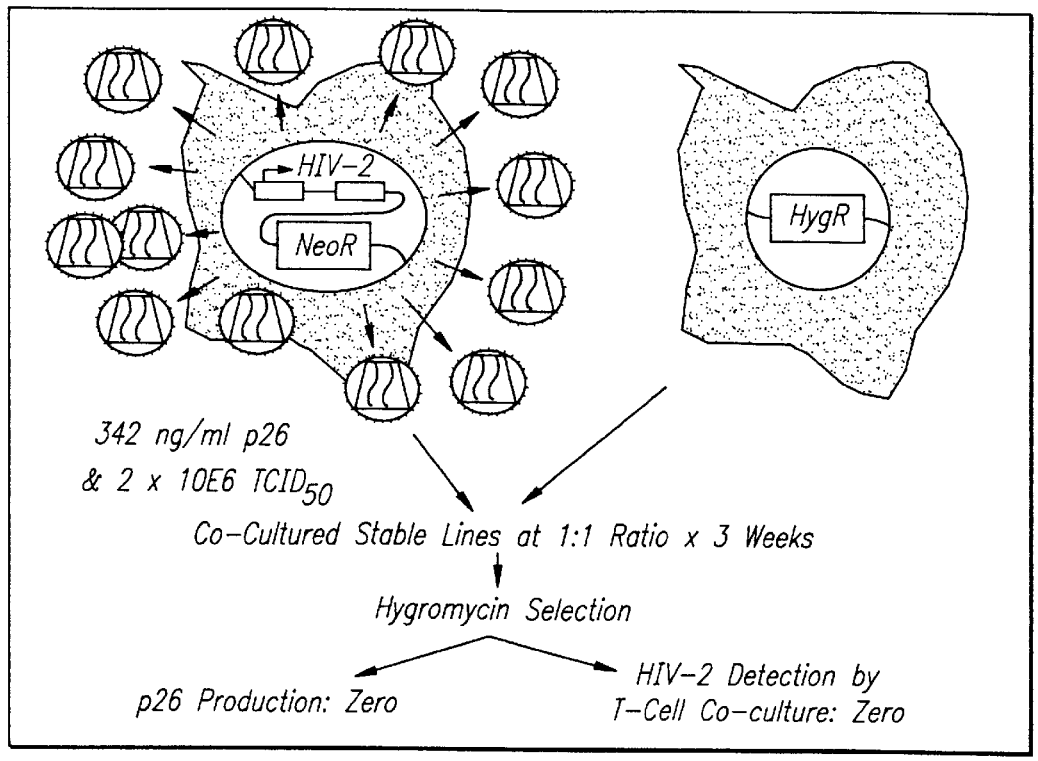

FIG. 12 shows a strategy for testing cell to cell spread of HIV-2 in producer cell lines.

Figure 13:
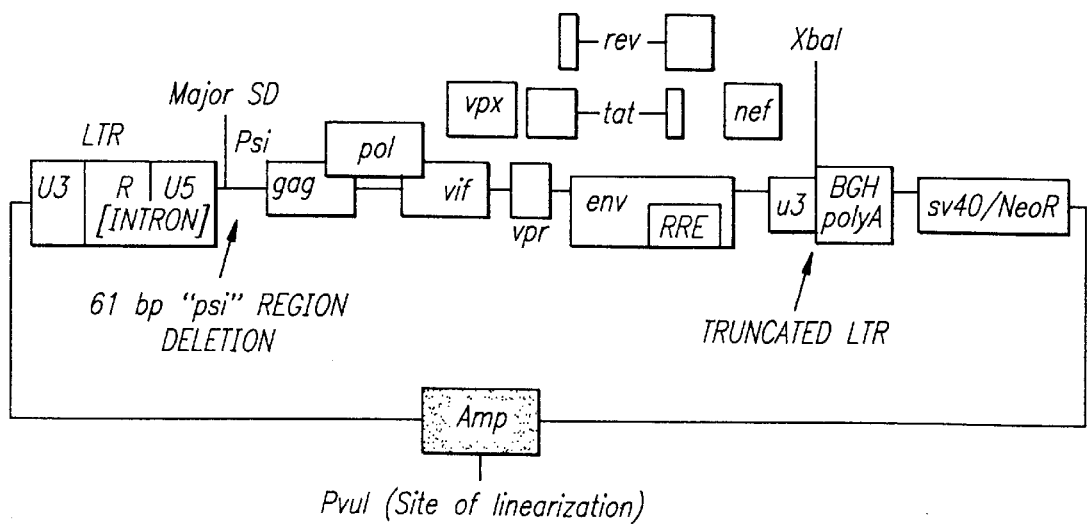

FIG. 13 shows HIV-2 expression plasmid 40, with XbaI and PvuI sites indicated.

Figure 14:
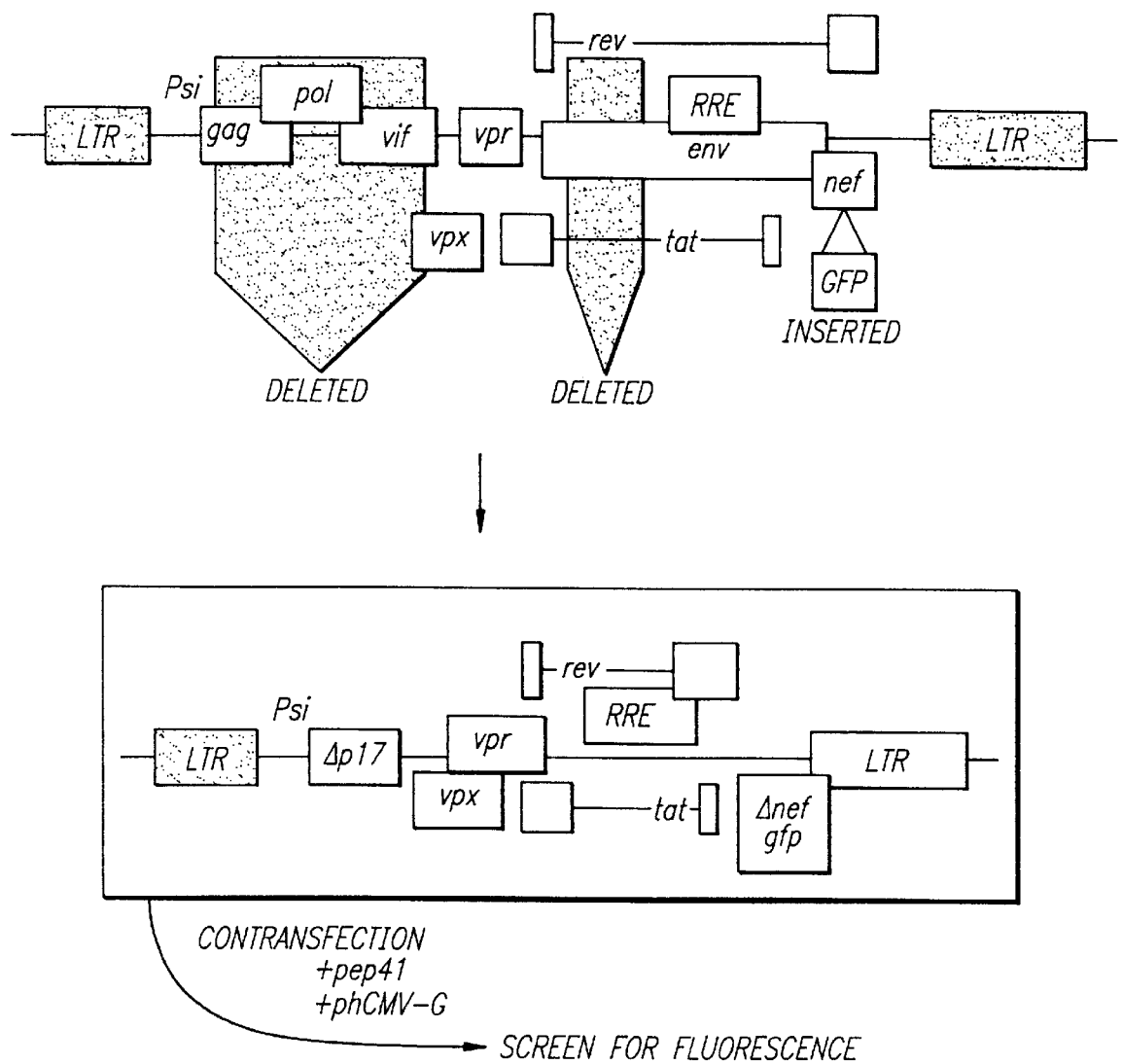

FIG. 14 shows the construction of a GFP cell transduction vector.

DEFINITIONS

Unless defined otherwise, all technical and scientific terms used herein have the same meaning as commonly understood by one of ordinary skill in the art to which this invention belongs. Singleton et al (1994) *Dictionary of Microbiology and Molecular Biology*, second edition, John Wiley and Sons (New York) provides one of skill with a general dictionary of many of the terms used in this invention. Although any methods and materials similar or equivalent to those described herein can be used in the practice or testing of the present invention, the preferred methods and materials are described. For purposes of the present invention, the following terms are defined below.

An "HIV-2 provirus" includes nucleic acids encoded by the HIV-2 genome. The nucleic acid is typically a DNA or RNA encoding an entire HIV-2 genome incorporated into a vector (e.g., a bacterial or eukaryotic plasmid, or a virus such as a λ-phage), or cell chromosome, but in the context of this invention also includes HIV-2 encoded DNA which is not incorporated into a vector (e.g., a restriction fragment) and RNA (e.g., HIV-2 genomic RNA which is to be incorporated into an HIV capsid). An HIV-2 provirus also optionally includes nucleic acids unrelated to HIV (e.g., vector or chromosomal sequences which flank HIV-2 encoded DNA).

A "full-length HIV-2 genome" consists of a nucleic acid (RNA or DNA) encoded by an HIV-2 virus or viral clone which includes the 5' and 3' LTR regions and the genes between the LTR regions which are present in a typical wild-type HIV-2 virus (e.g., env, nef, rev, vpx, tat, gag, pol, vif, and vpr).

An "activating deletion" in an HIV-2 LTR is a nucleic acid subsequence deletion, as compared to related HIV-2 strains, which increases the basal activity of the LTR promoter.

"High basal activity" in the context of a particular HIV-2 LTR refers to an ability of the LTR to direct expression of the HIV-2 transcript in excess of a wild-type strain of HIV-2 such as HIV-2$_{ST}$ (Kumar, et al. (1990) *Journal of Virology* 64, 890–901). Typically, the basal activity is at least about 1.5 times greater than HIV-2$_{ST}$, and preferably, the basal activity is about twice that of the HIV-2$_{ST}$ LTR.

A "constitutive" promoter is a promoter which is active under most environmental and developmental conditions.

"Encapsidation" generically refers to the process of incorporating a nucleic acid sequence (e.g., a provirus) into a viral particle. In the context of HIV-2, the nucleic acid is typically an RNA. A "viral particle" is a generic term which includes a viral "shell", "particle" or "coat", including a protein "capsid", a "lipid enveloped structure", a "protein-nucleic acid capsid", or a combination thereof (e.g., a lipid-protein envelope surrounding a protein-nucleic acid particle).

The term "identical" in the context of two nucleic acid or polypeptide sequences refers to the residues in the two sequences which are the same when aligned for maximum correspondence. When percentage of sequence identity is used in reference to proteins or peptides it is recognized that residue positions which are not identical often differ by conservative amino acid substitutions, where amino acids residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4: 11–17 (1988) e.g., as implemented in the program PC/GENE (Intelligenetics, Mountain View, Calif., USA).

A "comparison window", as used herein, refers to a segment of at least about 50 contiguous positions, usually about 50 to about 200, more usually about 100 to about 150 in which a sequence is compared to a reference sequence of the same number of contiguous positions after the two sequences are optimally aligned.

Methods of alignment of sequences for comparison are well known in the art. Optimal alignment of sequences for comparison may be conducted by the local homology algorithm of Smith and Waterman (1981) Adv. Appl. Math. 2: 482; by the homology alignment algorithm of Needleman and Wunsch (1970) J. Mol. Biol 48: 443; by the search for similarity method of Pearson and Lipman (1988) Proc. Natl. Acad. Sci. USA 85: 2444; by computerized implementations of these algorithms (including, but not limited to CLUSTAL in the PC/Gene program by Intelligenetics, Mountain View, Calif., GAP, BESTFIT, FASTA, and TFASTA in the Wisconsin Genetics Software Package, Genetics Computer Group (GCG), 575 Science Dr., Madison, Wis., USA); the CLUSTAL program is well described by Higgins and Sharp (1988) Gene, 73: 237–244 and Higgins and Sharp (1989) CABIOS 5: 151–153; Corpet, et al. (1988) Nucleic Acids Research 16, 10881–90; Huang, et al. (1992) Computer Applications in the Biosciences 8, 155–65, and Pearson, et al. (1994) Methods in Molecular Biology 24, 307–31. Alignment is also often performed by inspection and manual alignment.

"Conservatively modified variations" of a particular nucleic acid sequence refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every nucleic acid sequence herein which encodes a polypeptide also describes every possible silent variation. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence. Furthermore, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W. H. Freeman and Company.

An "inducible" promoter is a promoter which is under environmental or developmental regulation.

The terms "isolated" or "biologically pure" refer to material which is substantially or essentially free from components which normally accompany it as found in its native state. The isolated nucleic acids of this invention do not contain materials normally associated with their in situ environment, in particular, nuclear, cytosolic or membrane associated proteins or nucleic acids other than those nucleic acids which are indicated.

The term "labeled nucleic acid probe" refers to a nucleic acid probe that is bound, either covalently, through a linker, or through ionic, van der Waals or hydrogen "bonds" to a label such that the presence of the probe may be detected by detecting the presence of the label bound to the probe.

The term "label" refers to a composition detectable by spectroscopic, photochemical, biochemical, immunochemical, or chemical means. For example, useful labels include $^{32}$P, $^{35}$S, fluorescent dyes, electron-dense reagents, enzymes (e.g., as commonly used in an ELISA), biotin, dioxigenin, or haptens and proteins for which antisera or monoclonal antibodies are available.

The term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. Unless otherwise indicated, a particular nucleic acid sequence optionally includes the complementary sequence thereof.

The term "operably linked" refers to functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "recombinant" when used with reference to a cell indicates that the cell replicates or expresses a nucleic acid, or expresses a peptide or protein encoded by nucleic acid whose origin is exogenous to the cell. Recombinant cells can express genes that are not found within the native (non-recombinant) form of the cell. Recombinant cells can also express genes found in the native form of the cell wherein the genes are re-introduced into the cell or a progenitor of the cell by artificial means.

The term "subsequence" in the context of a particular nucleic acid sequence refers to a region of the nucleic acid equal to or smaller than the specified nucleic acid.

"Stringent conditions" in the context of nucleic acid hybridization are sequence dependent and are different under different environmental parameters. An extensive guide to the hybridization of nucleic acids is found in Tijssen (1993) *Laboratory Techniques in biochemistry and molecular biology—hybridization with nucleic acid probes* part I chapter 2 "overview of principles of hybridization and the strategy of nucleic acid probe assays", Elsevier, N.Y. Generally, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Highly stringent conditions are selected to be equal to the $T_m$ point for a particular probe. Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

A "vector" is a composition which can transduce, transfect, transform or infect a cell, thereby causing the cell to express nucleic acids and/or proteins other than those native to the cell, or in a manner not native to the cell. A cell is "transduced" by a nucleic acid when the nucleic acid is translocated into the cell from the extracellular environment. Any method of transferring a nucleic acid into the cell may be used; the term, unless otherwise indicated, does not imply any particular method of delivering a nucleic acid into a cell. A cell is "transformed" by a nucleic acid when the nucleic acid is transduced into the cell and stably replicated. A vector includes a nucleic acid (ordinarily RNA or DNA) to be expressed by the cell. A vector optionally includes materials to aid in achieving entry of the nucleic acid into the cell, such as a viral particle, liposome, protein coating or the like. A "cell transduction vector" is a vector which encodes a nucleic acid capable of stable replication and expression in a cell once the nucleic acid is transduced into the cell.

A "packaging vector" is a vector which encodes components necessary for production of HIV particles by a cell transduced by the packaging vector. The packaging vector optionally includes all of the components necessary for production of HIV particles, or optionally includes a subset of the components necessary for HIV packaging. For instance, in one preferred embodiment, a packaging cell is transduced with more than one packaging vector nucleic acid, each of which has a complementary role in the production of an HIV particle.

Two HIV-based packaging vectors are "complementary" when the two together encode the functions necessary for HIV packaging, and when each individually does not encode all of the functions necessary for packaging. Thus, when the two vectors transduce a single cell they together encode the information for production of HIV-based packaging particles. The use of such complementary vectors increases the safety of any packaging cell made by transduction with a packaging vector nucleic acid.

Packaging vectors encode HIV particles. The HIV particles are competent to package target RNA which has an HIV packaging site. "High efficiency packaging vectors" package target RNAs such that packaging cells stably transduced with the packaging vector and transduced with a target packagable nucleic acid corresponding to the target packagable RNA produce packaged target RNA at a titer of at least about $10^3$ to about $10^4$ transducing units per ml of cell supernatant or more, more preferably at least about $10^4$ to about $10^5$ transducing units per ml or more and often $10^5$ to $10^6$ transducing units or more. A "transducing unit" is a measure of the number of infective viral particles in a sample, typically as measured by an effect on a population of transducible cells. For example, where the cell population is exposed to a virulent viral particle, cell death in a population of cells (e.g., TCID50/ml, or viral plaque forming units/ml) is a measurement of transduction. Where the viral particle is not virulent, but carries a marker, the transfer of the marker (e.g., neomycin resistance, or LacZ staining) is monitored. See, Examples 10 and 11. Transducing units can be correlated to the number of viral particles in a sample,. e.g., using an ELISA assay to quantify the number of particles, and an activity assay (TCID50/ml, plaque formation assay, or marker detection) to measure the effect of the particles on a population of cells.

DETAILED DESCRIPTION

This invention provides HIV-2 nucleic acids, polypeptides, structural components (e.g., capsids and envelopes), whole viruses, subclones, immunogenic compositions, gene therapy vectors, cell systems and proviruses. The compositions are useful as components of diagnostic assays, for the synthesis of diagnostic reagents, as vaccines against HIV infection, for the production of HIV-2 based retroviral packaging cells, and as components of cell transduction and gene therapy vectors.

Proviruses such as HIV-$2_{KR}$ which are isolated from a particular library of HIV molecular clones generated from the viral infection of a single individual cannot be isolated using a molecular probe to a portion of the provirus from a different molecular library. This is because the provirus is unique to the specific molecular library. Accordingly, any prior art disclosure of a molecular probe directed to a particular unique provirus cannot be used to isolate the unique proviruses of the invention in the absence of a molecular library containing a clone of the provirus.

The present invention provides unique HIV-2 proviruses including the HIV-$2_{KR}$ provirus. The complete sequence of the HIV-$2_{KR}$ proviral clone is provided, enabling one of skill to generate the clone synthetically, or by modification of other known HIV clones. In addition, the clone was deposited as a plasmid ("D53") with the ATCC on Jul. 26, 1995. Making HIV-2 nucleic acids, proviruses and provirus fragments The present invention provides a variety of HIV-2 nucleic acids, including proviruses and provirus fragments such as provirus subclones, PCR primers and molecular probes. In one preferred embodiment, the invention provides the HIV-2 proviral molecular clone HIV-$2_{KR}$. The complete sequence of the clone is given in SEQ ID NO: 1, and the sequence has been deposited with GenBank (GenBank No. U22047). In addition, a plasmid (D53) with an HIV-$2_{KR}$ provirus containing the complete HIV-$2_{KR}$ sequence was deposited with the ATCC.

Given the sequence of a provirus of the present invention such as HIV-$2_{KR}$, one of skill can construct a variety of clones containing derivative proviruses and provirus subsequences. Cloning methodologies to accomplish these ends, and sequencing methods to verify the sequence of nucleic acids are well known in the art. Examples of appropriate cloning and sequencing techniques, and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, N.Y., (Sambrook); and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), and Applied Biosystems (Foster City, Calif.), as well as many other commercial sources known to one of skill.

The nucleic acid compositions of this invention, whether RNA, cDNA, genomic DNA, or a hybrid of the various combinations, are isolated from natural sources or synthesized in vitro. The nucleic acids claimed are present in transformed or transfected whole cells, in transformed or transfected cell lysates, or in a partially purified or substantially pure form.

In vitro amplification techniques are suitable for amplifying provirus sequences for use as molecular probes or generating proviral nucleic acid fragments for subsequent subcloning. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA) are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) C&EN 36–47; *The Journal Of NIH Research* (1991) 3, 81–94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077–1080; Van Brunt (1990) *Biotechnology* 8, 291–294; Wu and Wallace, (1989) *Gene* 4, 560; Barringer et al. (1990) *Gene* 89, 117, and Sooknanan and Malek (1995) *Biotechnology* 13: 563–564. Improved methods of cloning in vitro amplified nucleic acids are described in Wallace et at., U.S. Pat. No. 5,426,039. Improved methods of amplifying large nucleic acids are summarized in Cheng et al. (1994) *Nature* 369: 684–685 and the references therein. One of skill will appreciate that essentially any RNA can be converted into a double stranded DNA suitable for restriction digestion, PCR expansion and sequencing using reverse transcriptase and a polymerase. See, Ausbel, Sambrook and Berger, all supra.

Oligonucleotides for use as probes, e.g., in in vitro amplification methods, or for use as gene probes are typically chemically synthesized according to the solid phase phosphoramidite triester method described by Beaucage and Caruthers (1981), *Tetrahedron Letts.,* 22(20):1859–1862, e.g., using an automated synthesizer, as described in Needham-VanDevanter et al. (1984) *Nucleic Acids Res.,* 12:6159–6168. Purification of oligonucleotides, where necessary, is typically performed by either native acrylamide gel electrophoresis or by anion-exchange HPLC as described in Pearson and Regnier (1983) *J. Chrom.* 255:137–149. The sequence of the synthetic oligonucleotides can be verified using the chemical degradation method of Maxam and Gilbert (1980) in Grossman and Moldave (eds.) Academic Press, New York, *Methods in Enzymology* 65:499–560.

The polypeptides of the invention can be synthetically prepared in a wide variety of well-know ways. For instance, polypeptides of relatively short size, can be synthesized in solution or on a solid support in accordance with conventional techniques. See, e.g., Merrifield (1963) *J. Am. Chem. Soc.* 85:2149–2154. Various automatic synthesizers are commercially available and can be used in accordance with known protocols. See, e.g., Stewart and Young (1984) *Solid Phase Peptide Synthesis,* 2d. ed., Pierce Chemical Co.

Making Conservative Modifications of the Nucleic Acids and Polypeptides of the Invention One of skill will appreciate that many conservative variations of the proviral sequences disclosed yield an essentially identical virus. For example, due to the degeneracy of the genetic code, "silent substitutions" (i.e., substitutions of a nucleic acid sequence which do not result in an alteration in an encoded polypeptide) are an implied feature of every nucleic acid sequence which encodes an amino acid. Similarly, "conservative amino acid substitutions," in one or a few amino acids in an amino acid sequence are substituted with different amino acids with highly similar properties (see, the definitions section, supra), are also readily identified as being highly similar to a disclosed amino acid sequence, or to a disclosed nucleic acid sequence which encodes an amino acid. Such conservatively substituted variations of each explicitly disclosed sequence are a feature of the present invention.

One of skill will recognize many ways of generating alterations in a given nucleic acid sequence. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, Giliman and Smith (1979) *Gene* 8:81–97; Roberts et al. (1987) *Nature* 328:731–734 and Sambrook, Innis, Ausbel, Berger, Needham VanDevanter and Mullis (all supra).

Most commonly, HIV-2 polypeptide sequences are altered by altering the corresponding nucleic acid sequence and expressing the polypeptide. However, HIV-2 polypeptide sequences are also optionally generated synthetically on commercially available peptide synthesizers to produce any desired polypeptide (see, Merrifield, and Stewart and Young, supra).

One of skill can select a desired nucleic acid or polypeptide of the invention based upon the sequences provided and upon knowledge in the art regarding HIV strains generally. The life-cycle, genomic organization, developmental regulation and associated molecular biology of HIVs have been the focus of over a decade of intense research. The specific effects of many mutations in the HIV genome are known. Moreover, general knowledge regarding the nature of proteins and nucleic acids allows one of skill to select appropriate sequences with activity similar or equivalent to the nucleic acids and polypeptides disclosed in the sequence listings herein. The definitions section herein describes exemplar conservative amino acid substitutions.

Finally, most modifications to nucleic acids and polypeptides are evaluated by routine screening techniques in suitable assays for the desired characteristic. For instance, changes in the immunological character of a polypeptide can be detected by an appropriate immunological assay. Modifications of other properties such as nucleic acid hybridization to a target nucleic acid, redox or thermal stability of a protein, hydrophobicity, susceptibility to proteolysis, or the tendency to aggregate are all assayed according to standard techniques.

Use of The Nucleic Acids of The Invention as Molecular Probes

The nucleic acids of the invention are useful as molecular probes, in addition to their utility in encoding the polypeptides described herein. A wide variety of formats and labels are available and appropriate for nucleic acid hybridization, including those reviewed in Tijssen (1993) *Laboratory Techniques in biochemistry and molecular biology— hybridization with nucleic acid probes* parts I and II, Elsevier, N.Y. and Choo (ed) (1994) *Methods In Molecular Biology Volume* 33- *In Situ Hybridization Protocols* Humana Press Inc., New Jersey (see also, other books in the Methods in Molecular Biology series); see especially, Chapter 21 of Choo (id) "Detection of Virus Nucleic Acids by Radioactive and Nonisotopic in Situ Hybridization".

For instance, PCR is routinely used to detect HIV nucleic acids in biological samples (see, Innis, supra for a general description of PCR techniques). Accordingly, in one class of embodiments, the nucleic acids of the invention are used as PCR primers, or as positive controls in PCR reactions for the detection of HIV in a biological sample such as human blood. Briefly, nucleic acids encoded by the nucleic acid constructs of the invention are used as templates to synthetically produce oligonucleotides of about 20–100 nucleotides with sequences similar or identical to the selected nucleic acid. The oligonucleotides are then used as primers in PCR reactions to detect HIV nucleic acids in biological samples such as human blood. The nucleic acids of the invention (i.e., a nucleic acid corresponding to the region to be amplified) are also used as amplification templates in separate reactions to determine that the PCR reagents and hybridization conditions are appropriate.

Other methods for the detection of HIV nucleic acids in biological samples using nucleic acids of the invention include Southern blots, northern blots, in situ hybridization (including Fluorescent in situ hybridization (FISH), reverse chromosome painting, FISH on DAPI stained chromosomes, generation of Alphoid DNA probes for FISH using PCR, PRINS labeling of DNA, free chromatin mapping and a variety of other techniques described in Choo (supra)). A variety of automated solid-phase detection techniques are also appropriate. For instance, very large scale immobilized polymer arrays (VLSIPS™) are used for the detection of nucleic acids. See, Tijssen (supra), Fodor et al. (1991) *Science*, 251: 767–777 and Sheldon et al. (1993) *Clinical Chemistry* 39(4): 718–719.

Expression of HIV-2 polypeptides

Once an HIV-2 provirus nucleic acid or HIV-2 provirus subsequence nucleic acid is isolated and cloned, one may express the nucleic acid in a variety of recombinantly engineered cells known to those of skill in the art. Examples of such cells include bacteria, yeast, filamentous fungi, insect (especially employing baculoviral vectors), and mammalian cells. It is expected that those of skill in the art are knowledgeable in the numerous expression systems available for cloning and expression of HIV-2 nucleic acids.

In brief summary, the expression of natural or synthetic nucleic acids encoding, e.g., HIV-2$_{KR}$ polypeptides is typically achieved by operably linking a nucleic acid encoding the polypeptide of interest to a promoter (which is either constitutive or inducible), and incorporating the construct into an expression vector. The vectors can be suitable for replication and integration in prokaryotes, eukaryotes, or both. Typical cloning vectors contain transcription and translation terminators, transcription and translation initiation sequences, and promoters useful for regulation of the expression of the particular nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. See, e.g., Sambrook and Ausbel (both supra).

To obtain high levels of expression of a cloned nucleic acid it is common to construct expression plasmids which typically contain a strong promoter to direct transcription, a ribosome binding site for translational initiation, and a transcription/translation terminator. For example, as described herein, the polypeptides encoded by the HIV-2 proviruses of the present invention (including HIV-$2_{KR}$), which are useful as antigenic reagents and as components of diagnostic assays, are optionally expressed in bacterial cells such as *E. coli*. Examples of regulatory regions suitable for this purpose in *E. coli* are the promoter and operator region of the *E. coli* tryptophan biosynthetic pathway as described by Yanofsky, C., 1984, *J. Bacteriol.,* 158:1018–1024 and the leftward promoter of phage lambda ($P_l$) as described by Herskowitz and Hagen, 1980, *Ann. Rev. Genet.,* 14:399–445. The inclusion of selection markers in DNA vectors transformed in bacteria such as *E. coli* is also useful. Examples of such markers include genes specifying resistance to ampicillin, tetracycline, or chloramphenicol. See, Sambrook, Ausbel, and Berger for details concerning selection markers, e.g., for use in *E. coli*. Expression systems for expressing polypeptides are available using *E. coli*, Bacillus sp. (Palva, I. et al., 1983, *Gene* 22:229–235; Mosbach, K. et al., *Nature,* 302:543–545) and Salmonella. *E. coli* systems are the most common, and best defined prokaryotic expression systems and are, therefore, preferred when expression is performed in prokaryotes.

Polypeptides produced by prokaryotic cells often require exposure to chaotropic agents for proper folding. During purification from, e.g., *E. coli*, the expressed protein is optionally denatured and then renatured. This is accomplished, e.g., by solubilizing the bacterially produced antibodies in a chaotropic agent such as guanidine HCl. The antibody is then renatured, either by slow dialysis or by gel filtration. See, U.S. Pat. No. 4,511,503.

Methods of transfecting and expressing genes in eukaryotic cells are also known in the art. For example, synthesis of heterologous proteins in yeast is well known and described. See, e.g., Sherman et al. (1982) *Methods in Yeast Genetics*, Cold Spring Harbor Laboratory. Examples of promoters for use in yeast include GAL1,10 (Johnson and Davies (1984) *Mol. Cell. Biol.* 4:1440–1448) ADH2 (Russell et al. (1983) *J. Biol. Chem.* 258:2674–2682), PH05 (*EMBO J.* (1982) 6:675–680), and MFα1 (Herskowitz and Oshima (1982) in *The Molecular Biology of the Yeast Saccharomyces* (eds. Strathern, Jones, and Broach) Cold Spring Harbor Lab., Cold Spring Harbor, N.Y., pp. 181–209). A multicopy plasmid with selective markers such as Leu-2, URA-3, Trp-1, and His-3 is also commonly used. A number of yeast expression plasmids like YEp6, YEp13, YEp4 can be used as expression vectors. An HIV-2 gene of interest can be fused to any of the promoters in various yeast vectors. The above-mentioned plasmids have been fully described in the literature (Botstein et al. (1979) *Gene* 8:17–24; Broach, et al. (1979) *Gene,* 8:121–133).

Two procedures are commonly used in transforming yeast cells. In one case, yeast cells are first converted into protoplasts using zymolyase, lyticase or glusulase, followed by addition of DNA and polyethylene glycol (PEG). The PEG-treated protoplasts are then regenerated in a 3% agar medium under selective conditions. Details of this procedure are given in Beggs (1978) *Nature* (London) 275:104–109, and Hinnen et al. (1978) *Proc. Natl. Acad. Sci. USA* 75:1929–1933. The second procedure does not involve removal of the cell wall. Instead the cells are treated, e.g., with lithium chloride or acetate and PEG and put on selective plates (Ito, et al. (1983) *J. Bact.* 153:163–168).

The polypeptides of interest are isolated from yeast by lysing the cells and applying standard protein isolation techniques to the lysates. The polypeptides of this invention are purified to substantial purity by standard techniques well known in the art, including selective precipitation with such substances as ammonium sulfate, column chromatography, immunopurification methods, and others. See, for instance, Scopes (1982) *Protein Purification: Principles and Practice* Springer-Verlag New York. The monitoring of the purification process is accomplished by using Western blot techniques or radioimmunoassays or other standard immunoassay techniques, or by monitoring the protein directly, e.g., by coomassie blue or silver-stain polyacrylamide gel electrophoresis.

Transducing cells with nucleic acids can involve, for example, incubating viral vectors (e.g., retroviral or adeno-associated viral vectors) containing nucleic acids which encode polypeptides of interest with cells within the host range of the vector. See, e.g., *Methods in Enzymology*, vol. 185, Academic Press, Inc., San Diego, Calif. (D. V. Goeddel, ed.) (1990) or M. Krieger, *Gene Transfer and Expression—A Laboratory Manual*, Stockton Press, New York, N.Y., (1990) and the references cited therein. The culture of cells used in conjunction with the present invention, including cell lines and cultured cells from tissue or blood samples is well known in the art. Freshney (*Culture of Animal Cells, a Manual of Basic Technique*, third edition Wiley-Liss, New York (1994)) and the references cited therein provides a general guide to the culture of cells.

Illustrative of cell cultures useful for the production of HIV-2 polypeptides are cells of insect or mammalian origin. Mammalian cell systems often will be in the form of monolayers of cells, although mammalian cell suspensions are also used. Illustrative examples of mammalian cell lines include VERO and HeLa cells, Chinese hamster ovary (CHO) cell lines, W138, BHK, Cos-7 or MDCK cell lines (see, e.g., Freshney, supra).

As indicated above, the vector, e.g., a plasmid, which is used to transform the host cell, preferably contains nucleic acid sequences to initiate transcription and sequences to control the translation of the encoded polypeptide. These sequences are referred to generally as expression control sequences. When the host cell is of insect or mammalian origin, illustrative expression control sequences are obtained from the SV-40 promoter (*Science* (1983) 222:524–527), the CMV I.E. Promoter (*Proc. Natl. Acad. Sci.* (1984) 81:659–663) or the metallothionein promoter (*Nature* (1982) 296:39–42). The cloning vector containing the expression control sequences is cleaved using restriction enzymes and adjusted in size as necessary or desirable and ligated with DNA coding for the HIV-2 polypeptide of interest by means well known in the art.

As with yeast, when higher animal host cells are employed, polyadenlyation or transcription terminator sequences from known mammalian genes are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague et al. (1983) *J. Virol.* 45: 773–781).

Additionally, gene sequences to control replication in a particular host cell are incorporated into the vector such as those found in bovine papilloma virus type-vectors. See, Saveria-Campo (1985), "Bovine Papilloma virus DNA a Eukaryotic Cloning Vector" in *DNA Cloning* Vol II *a Practical Approach Glover* (ed) IRL Press, Arlington, Va. pp. 213–238.

Host cells are competent or rendered competent for transformation by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, receptor-mediated endocytosis, electroporation and micro-injection of the DNA directly into the cells.

Transformed cells are cultured by means well known in the art. See, Freshny (supra), Kuchler et al. (1977) *Biochemical Methods in Cell Culture and Virology*, Kuchler, R. J., Dowden, Hutchinson and Ross, Inc. The expressed polypeptides are isolated from cells grown as suspensions or as monolayers. The latter are recovered by well known mechanical, chemical or enzymatic means. See, Scopes, supra.

Making Antibodies to HIV-2 provirus polypeptides

HIV-2 provirus polypeptides (including HIV-$2_{KR}$) polypeptides are optionally bound by antibodies in one class of embodiments of the present invention. The polypeptides are used as diagnostic reagents as described herein, or are used as immunogens for the production of antibodies which are also useful, e.g., as diagnostic reagents. Methods of producing polyclonal and monoclonal antibodies are known to those of skill in the art. See, e.g., Coligan (1991) *Current Protocols in Immunology* Wiley/Greene, N.Y.; and Harlow and Lane (1989) *Antibodies: A Laboratory Manual* Cold Spring Harbor Press, N.Y.; Stites et al. (eds.) *Basic and Clinical Immunology* (4th ed.) Lange Medical Publications, Los Altos, Calif., and references cited therein; Goding (1986) *Monoclonal Antibodies: Principles and Practice* (2d ed.) Academic Press, New York, N.Y.; and Kohler and Milstein (1975) Nature 256: 495–497. Other suitable techniques for antibody preparation include selection of libraries of recombinant antibodies in phage or similar vectors. See, Huse et al. (1989) *Science* 246: 1275–1281; and Ward, et al. (1989) *Nature* 341: 544–546. Specific monoclonal and polyclonal antibodies and antisera will usually bind with a $K_D$ of at least about 0.1 mM, more usually at least about 1 $\mu$M, preferably at least about 0.1 $\mu$M or better, and most typically and preferably, 0.1 $\mu$M or better.

Frequently, the polypeptides and their corresponding antibodies will be labeled by joining, either covalently or non covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced. See, Cabilly, U.S. Pat. No. 4,816,567; and Queen et al. (1989) *Proc. Nat'l Acad. Sci. USA* 86: 10029–10033.

The immunogenic compositions of this invention (e.g., peptides, nucleic acids, viral particles, viral capsids, etc.) are also used for affinity chromatography in isolating and quantitating HIV-2 antibodies and anti-sera. Columns are prepared, e.g., with the antibodies linked to a solid support, e.g., particles, such as agarose, Sephadex, or the like, where a cell lysate is passed through the column, washed, and treated with increasing concentrations of a mild denaturant, whereby purified antibodies are released.

Immunoassay formats

In one preferred class of embodiments, the HIV-2 polypeptides of the present invention are used for the detection of HIV infection in human (or animal) patients. For instance, HIV-2 polypeptides (e.g., polypeptides encoded by HIV-2$_{KR}$) are useful in western blots for the detection of antibodies to HIV in a patient's blood. Such tests are well known, and are presently a standard method by which HIV-1 and HIV-2 infections are detected in patient populations. The HIV-2 polypeptides of the invention (individually or as part of an intact HIV-2 virus in a viral particle) can be used in known and standard immunoassay methods for the detection of HIV infections. A variety of immunoassay formats are known and available.

A particular protein can be quantified by a variety of immunoassay methods. For a review of immunological and immunoassay procedures in general, see Stites and Terr (eds.) 1991 *Basic and Clinical Immunology* (7th ed.). Moreover, the immunoassays of the present invention can be performed in any of several configurations, e.g., those reviewed in Maggio (ed.) (1980) *Enzyme Immunoassay* CRC Press, Boca Raton, Fla.; Tijan (1985) "Practice and Theory of Enzyme Immunoassays," *Laboratory Techniques in Biochemistry and Molecular Biology*, Elsevier Science Publishers B.V., Amsterdam; Harlow and Lane, supra; Chan (ed.) (1987) *Immunoassay: A Practical Guide* Academic Press, Orlando, Fla.; Price and Newman (eds.) (1991) *Principles and Practice of Immunoassays* Stockton Press, N.Y.; and Ngo (ed.) (1988) *Non isotopic Immunoassays* Plenum Press, N.Y.

Immunoassays often utilize a labeling agent to specifically bind to and label the binding complex formed by the capture agent and the analyte (HIV-2 polypeptides are either the capture agent, or the analyte, depending on the format of the assay). The labeling agent may itself be one of the moieties comprising the capture agent/analyte complex. Thus, the labeling agent is optionally a labeled HIV-2 polypeptide or a labeled HIV-2 antibody. Alternatively, the labeling agent is optionally a third moiety, such as another antibody, that specifically binds to the capture agent/polypeptide complex, or to a modified capture group (e.g., biotin) which is covalently linked to the peptide or antibody.

In one embodiment, the labeling agent is an antibody that specifically binds to the capture agent, which is an HIV-2 polypeptide antibody. Such agents are well known to those of skill in the art, and most typically comprise labeled antibodies that specifically bind antibodies of the particular animal species from which the capture agent is derived (e.g., an anti-species antibody). Thus, for example, where the capture agent is a mouse antibody, the label agent may be a goat anti-mouse IgG, i.e., an antibody specific to the constant region of the mouse antibodies.

Other proteins capable of specifically binding immunoglobulin constant regions, such as streptococcal protein A or protein G are also useful as labeling agents. These proteins are normal constituents of the cell walls of streptococcal bacteria. They exhibit a strong non-immunogenic reactivity with immunoglobulin constant regions from a variety of species. See, generally Kronval, et al., (1973) *J. Immunol.,* 111:1401–1406, and Akerstrom, et al., (1985) *J. Immunol.,* 135:2589–2542.

Alternatively, the HIV-2 polypeptide can be labeled directly, e.g., by producing the polypeptide in a cell culture containing radioactive amino acids, or by radiolabeling purified HIV-2 polypeptide.

In another embodiment, the capture agent is an HIV-2 polypeptide and the analyte is an HIV-2 polypeptide analyte. In this embodiment, the polypeptide is typically labeled directly (e.g., by radio labeling) or by using an antibody label distinct from the analyte antibody.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentration of capture agent and analyte, and the like. Usually, the assays are carried out at ambient temperature, although they can be conducted over a range of temperatures, such as 5° C. to 45° C.

Non Competitive Assay Formats

Immunoassays for detecting a polypeptide or antibody may be either competitive or noncompetitive. Noncompetitive immunoassays are assays in which the amount of captured analyte is directly measured. In one preferred "sandwich" assay, for example, the capture agent is bound directly to a solid substrate where it is immobilized. These immobilized capture agents then "capture" or "bind" analyte present in a test sample. The analyte thus immobilized is then bound by a labeling agent, such as an antibody bearing a label. Alternatively, the labeling agent may lack a direct label, but it may, in turn, be bound by a labeled third moiety such as an antibody specific to antibodies of the species from which the labeling agent is derived.

Sandwich assays for an analyte are optionally constructed. As described above, the immobilized capture agent specifically binds to the analyte in the sample. The labeled anti-analyte (labeling agent) then binds to the capture agent-analyte complex. Free labeling agent is washed away and the remaining bound labeled complex is detected (e.g., using a gamma detector where the label is radioactive).

Competitive Assay Formats

In competitive assays, the amount of analyte present in the test sample is measured indirectly by measuring the amount of an added (exogenous) analyte displaced (or competed away) from a capture agent by the analyte present in the sample. In one competitive assay, a known amount of analyte is added to the sample and the sample is contacted with a capture agent that specifically binds the analyte. The amount of analyte bound to the capture agent is inversely proportional to the concentration of analyte present in the sample.

In a preferred embodiment, the capture agent is immobilized on a solid substrate. The amount of analyte bound to the capture agent is determined either by measuring the amount of analyte present in an analyte-capture agent complex, or alternatively by measuring the amount of remaining uncomplexed analyte. The amount of analyte in a sample to be assayed may also be detected by providing exogenous labeled analyte to the assay.

A hapten inhibition assay is another preferred competitive assay. In this assay, a known analyte is immobilized on a solid substrate. A known amount of anti-analyte is added to the sample, and the sample is then contacted with the capture agent. In this case, the amount of anti-analyte bound to the immobilized capture agent is proportional to the amount of analyte present in the sample. Again, the amount of immobilized analyte is detected by quantitating either the immobilized fraction of anti-analyte or the fraction of the anti-analyte that remains in solution. Detection is direct where the anti-analyte is labeled, or indirect where a labeled moiety is subsequently added which specifically binds to the anti-analyte as described above.

Assays for HIV-2 Proviral Genes and Gene Products

Uses for HIV-2 Polypeptides and Nucleic Acids; Sample Collection and Processing

An HIV-2 transcript, antibody or polypeptide is preferably quantified in a biological sample, such as a cell, or a tissue sample derived from a patient. In a preferred embodiment, antisera to HIV-2 polypeptides are quantified in serum (See, supra). In another preferred embodiment, HIV-2 nucleic acids are detected in an infected patient using gene probes derived from the nucleic acids of the invention. For instance, in one embodiment, HIV nucleic acids in a biological sample are amplified by an in vitro amplification technique (e.g., PCR or LCR) and detected using labeled HIV-$2_{KR}$ nucleic acids.

The HIV-2 nucleic acids of the invention are also useful as control reagents. For instance, the HIV-$2_{KR}$ transcript or a portion thereof is useful as a control template to monitor the efficiency of in vitro amplification reactions. For instance, in a PCR reaction, in order to determine that all of the reagents are working properly (buffers, taq polymerase, etc.), one reaction (or a set of reactions at various concentrations of template) is set up using the HIV-$2_{KR}$ nucleic acid as a template (e.g., with HIV-2 primers) and run in parallel with nucleic acid from biological samples taken from patients as PCR templates. The presence of such as "positive control" reaction is a straightforward way of showing that a biological sample which tests "negative" (i.e., the in vitro amplification method does not produce an amplification product) does so because there is no template in the sample, and not because the reagents are defective.

Although the sample is typically taken from a human patient, the assays can be used to detect HIV-2 polypeptides or antibodies (including recombinant antibodies) in cells from eukaryotes in general, including plants, vertebrates and invertebrates, and in mammals in particular, such as dogs, cats, sheep, cattle and pigs, and most particularly primates such as humans, chimpanzees, gorillas, macaques, and baboons, and rodents such as mice, rats, and guinea pigs. As shown in the examples below, mice and macaques are both infected by HIV-$2_{KR}$.

The sample is pretreated as necessary by dilution in an appropriate buffer solution or concentrated, if desired. Many standard aqueous buffer solutions employing one of a variety of buffers, such as phosphate, Tris, or the like, at physiological pH are appropriate.

Quantification of Polypeptides, nucleic acids and Antibodies

HIV-2 antibodies, and the polypeptides and nucleic acids of the invention are detected and quantified by any of a number of means well known to those of skill in the art. These include analytic biochemical methods such as spectrophotometry, radiography, electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like. The detection of nucleic acids proceeds by well known methods such as Southern analysis, northern analysis, gel electrophoresis, PCR, radiolabeling and scintillation counting, and affinity chromatography.

Reduction of Non Specific Binding

One of skill will appreciate that it is often desirable to reduce non specific binding in immunoassays and during analyte purification. Where the assay involves an HIV-2 polypeptide, antibody, or other capture agent immobilized on a solid substrate, it is desirable to minimize the amount of non specific binding to the substrate. Means of reducing such non specific binding are well known to those of skill in the art. Typically, this involves coating the substrate with a proteinaceous composition. In particular, protein compositions such as bovine serum albumin (BSA), nonfat powdered milk, and gelatin are widely used.

Other Assay Formats

Western blot analysis can also be used to detect and quantify the presence of a polypeptide or antibody (peptide, transcript, or enzymatic digestion product) in the sample. The technique generally comprises separating sample products by gel electrophoresis on the basis of molecular weight, transferring the separated proteins to a suitable solid support, (such as a nitrocellulose filter, a nylon filter, or derivatized nylon filter), and incubating the sample with labeling antibodies that specifically bind to the analyte protein (antibody or HIV-2 polypeptide). The labeling antibodies specifically bind to analyte on the solid support. These antibodies are directly labeled, or alternatively are subsequently detected using labeling agents such as antibodies (e.g., labeled sheep anti-mouse antibodies where the antibody to an analyte is a murine antibody) that specifically bind to the labeling antibody.

Other assay formats include liposome immunoassays (LIAs), which use liposomes designed to bind specific molecules (e.g., antibodies) and release encapsulated reagents or markers. The released chemicals are then detected according to standard techniques (see, Monroe et al., (1986) *Amer. Clin. Prod. Rev.* 5:34–41).

Labels

Labeling agents include e.g., monoclonal antibodies, polyclonal antibodies, proteins such as those described herein, or other polymers such as affinity matrices, carbohydrates or lipids. Detection proceeds by any known method, such as immunoblotting, western analysis, gel-mobility shift assays, fluorescent in situ hybridization analysis (FISH), tracking of radioactive or bioluminescent markers, nuclear magnetic resonance, electron paramagnetic resonance, stopped-flow spectroscopy, column chromatography, capillary electrophoresis, Southern blotting, northern blotting, southwestern blotting, northwestern blotting, or other methods which track a molecule based upon size, charge or affinity. The particular label or detectable group used and the particular assay are not critical aspects of the invention. The detectable moeity can be any material having a detectable physical or chemical property. Such detectable labels have been well-developed in the field of gels, columns, solid substrates and immunoassays and, in general, any label useful in such methods can be applied to the present invention. Thus, a label is any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, Texas red, rhodamine, and the like), radio-labels (e.g., $^3$H, $^{125}$I, $^{35}$S, $^{14}$C, or $^{32}$P), enzymes (e.g., LacZ, CAT, horse radish peroxidase, alkaline phosphatase and others, commonly used as detectable enzymes, either as marker gene products or in an ELISA), nucleic acid intercalators (e.g., ethidium bromide) and colorimetric labels such as colloidal gold or colored glass or plastic (e.g. polystyrene, polypropylene, latex, etc.) beads.

The label is coupled directly or indirectly to the desired component of the assay according to methods well known in the art. As indicated above, a wide variety of labels are used, with the choice of label depending on the sensitivity required, ease of conjugation of the compound, stability requirements, available instrumentation, and disposal provisions.

Non radioactive labels are often attached by indirect means. Generally, a ligand molecule (e.g., biotin) is covalently bound to a polymer. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with labeled, anti-ligands. Alternatively, any haptenic or antigenic compound can be used in combination with an antibody.

Labels can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labelling or signal producing systems which may be used, used, see, U.S. Pat. No. 4,391,904, which is incorporated herein by reference.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence, e.g., by microscopy, visual inspection, via photographic film, by the use of electronic detectors such as charge coupled devices (CCDs) or photomultipliers and the like. Similarly, enzymatic labels may be detected by providing appropriate substrates for the enzyme and detecting the resulting reaction product. Finally, simple colorimetric labels are often detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of antibodies. In this case, antigen-coated (e.g., HIV-2 polypeptide-coated) particles are agglutinated by samples comprising the target antibodies. In this format, none of the components need be labeled and the presence of the target antibody is detected by simple visual inspection.

Substrates

As mentioned above, depending upon the assay, various components, including HIV-2 components, or anti-HIV-2 antibodies, are optionally bound to a solid surface. Many methods for immobilizing biomolecules to a variety of solid surfaces are known in the art. For instance, the solid surface may be a membrane (e.g., nitrocellulose), a microtiter dish (e.g., PVC, polypropylene, or polystyrene), a test tube (glass or plastic), a dipstick (e.g. glass, PVC, polypropylene, polystyrene, latex, and the like), a microcentrifuge tube, or a glass, silica, plastic, metallic or polymer bead. The desired component may be covalently bound, or noncovalently attached through nonspecific bonding.

A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials which are appropriate depending on the assay include paper, glasses, ceramics, metals, metalloids, semiconductive materials, cements and the like. In addition, substances that form gels, such as proteins (e.g., gelatins), lipopolysaccharides, silicates, agarose and polyacrylamides can be used. Polymers which form several aqueous phases, such as dextrans, polyalkylene glycols or surfactants, such as phospholipids, long chain (12–24 carbon atoms) alkyl ammonium salts and the like are also suitable. Where the solid surface is porous, various pore sizes may be employed depending upon the nature of the system.

In preparing the surface, a plurality of different materials are optionally employed, e.g., as laminates, to obtain various properties. For example, protein coatings, such as gelatin can be used to avoid non specific binding, simplify covalent conjugation, enhance signal detection or the like.

If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature. See, for example, *Immobilized Enzymes*, Ichiro Chibata, Halsted Press, New York, 1978, and Cuatrecasas, *J. Biol. Chem.* 245 3059 (1970) which are incorporated herein by reference.

In addition to covalent bonding, various methods for noncovalently binding an assay component can be used. Noncovalent binding is typically nonspecific absorption of a compound to the surface. Typically, the surface is blocked with a second compound to prevent nonspecific binding of labeled assay components. Alternatively, the surface is designed such that it nonspecifically binds one component but does not significantly bind another. For example, a surface bearing a lectin such as Concanavalin A will bind a carbohydrate containing compound but not a labeled protein that lacks glycosylation. Various solid surfaces for use in noncovalent attachment of assay components are reviewed in U.S. Pat. Nos. 4,447,576 and 4,254,082.

Infectivity Assays, Trans-complementation and Packaging Cells

The viruses of this invention can be used to determine whether cells have been infected with a particular virus. In one embodiment of this method, one group of cells in a sample to be tested is transduced with a nucleic acid construct containing a packagable or "encapsulateable" HIV-2 nucleic acid of the invention (e.g., an HIV-$2_{KR}$ subsequence with cis-active sequences necessary for packaging the HIV-$2_{KR}$ nucleic acid into an HIV-2 viral capsid)

which does not encode trans- active sequences necessary for packaging the nucleic acid (e.g., viral particle proteins). Another group of cells serves as a control. Both groups of cells are incubated under appropriate conditions and for a sufficient time for viral replication. After incubation, each group is examined for evidence of packaging of the nucleic acid construct into viral particles. Evidence of packaging of the test nucleic acid in the test group but not in the control group, indicates that cells in the test group are infected by a retrovirus (e.g., HIV-2).

Packaging Cells

The present invention provides stable HIV-2 based packaging cells. Prior art packaging systems are derived from HIV-1 and all evince a variety of limitations. Several use wild-type replication competent virus as the source of packaging proteins, and some represent simple pseudotyping of an env gene-mutated full-length provirus by VSV-G (i.e., they have no packaging construct, lines or vector lacking other structural genes). In general, two problems have been most prominent in this field: (1) titers have been exceedingly low ($10^1$–$10^2$) and (2) stable packaging lines have not been developed.

The packaging cell lines of the invention are different in two major ways. First, they are based upon HIV-2, a virus less pathogenic than HIV-1. In addition to this serious safety issue, e.g., for delivery of anti-HIV-1 genes to treat HIV disease, an HIV-1-based system is self-inactivating in direct proportion to the efficacy of the antiviral gene carried by gene therapy vectors directed against HIV-1.

HIV-$2_{KR}$ and conservative modifications thereof, are a preferred source of material for constructing packaging cell lines of the invention. HIV-$2_{KR}$ replicates to high titers in T cell lymphoblastoid lines, primary human macrophages and peripheral blood lymphocytes. HIV-$2_{KR}$ infects non-human primates and induces cell-mediated immunity against disease causation by a more pathogenic HIV-2 strain (HIV-2 EHO) but has itself proven completely apathogenic as well as unrecoverable by culture even years following intravenous challenge of rhesus macaques. Although HIV-$2_{KR}$ is preferred, other HIV-2 isolates, and components thereof can also be used in the packaging cells of the invention. Such clones are known to persons of skill, and publicly available. Well-established repositories of sequence information include GenBank, EMBL, DDBJ and the NCBI.

The invention provides stable packaging cell lines in addition to a transient transfection system for HIV-2. Stable cell lines have been difficult to make for HIV because of the genetic complexity of the viruses and because of the toxicity of HIV proteins in many cell lines. The HIV-2 envelope can be used for CD4-specific targeting from these lines. For transient packaging, the VSV-G protein, recently shown to have numerous advantages for virion particle stability and extended host range can be used.

The establishment of stable cell lines producing high titers of fully characterized transducing particles is a major step forward in the utilization of HIV-2 derived constructs for gene therapy. Suitable cells for transduction by the packaging nucleic acids of the invention to make packaging cells include established mammalian cell lines, and primary cells isolated from patients. Example cells include HeLa cells, Molt 4 clone 8 cells, Cos cells, CV-1 cells, 293 cells and Daudi cells.

High Efficiency Packaging Nucleic Acids

Trans active genes rendered inactive in a vaccine or gene therapy vector as described herein are also capable of trans-complementation in order to render the construct rescuable. This form of transcomplementation is used in creating HIV packaging cell lines and in performing co-infection assays and diagnostic methods. For instance, cells transduced with HIV-2 proviral sequences which lack the nucleic acid packaging site located in and around the major splice donor site and the gag initiator codon adjacent to the 5' LTR produce HIV trans active components, but do not specifically incorporate HIV-2 nucleic acids into the capsids produced, and therefore produce little or no live virus. As described in the Examples below, a 61 base-pair psi region deletion (from nt 1007–1067 of HIV-$2_{KR}$) from an infective HIV-2 proviral clone was sufficient to completely block packaging of nucleic acids with the deletion. However, as shown in the examples, the deletion clone (e.g., pEP40) produced high levels of HIV-2 trans active components sufficient to package HIV-2 packagable nucleic acids. pEP40 is an example of a high efficiency packaging vector which produces high levels of trans active components in packaging cells.

The high efficiency packaging vector nucleic acids of the invention encode some or all of the proteins needed to produce an HIV-2 particle. Typically, packaging vector nucleic acids are derived from an HIV viral genome, or a portion thereof. Packaging vector nucleic acids lack the nucleic acids necessary for packaging of an RNA corresponding to the packaging vector nucleic acid into an HIV capsid. That is, packaging vector nucleic acids are not themselves encapsulated in the HIV particles which they encode, i.e., the high efficiency packaging vector nucleic acids are not themselves virulent. Typically, nucleic acids corresponding to a substantial portion of the HIV-2 psi site are deleted or altered in the packaging vector relative to the wild-type HIV genomic RNA nucleic acid.

cis- and trans- active sequences are optionally deleted from a high efficiency packaging vector relative to a full-length HIV-2 genome to increase the safety of the vector. Where the sequences are required for HIV-2 packaging of an HIV-2 packagable nucleic acid or particle formation, the missing components are encoded by a second vector nucleic acid. For example, high efficiency packaging vectors optionally comprise deletion of an LTR (reducing the ability of the virus to integrate into a packaging cell chromosome) and/or a deletion in the env gene, with env components being supplied in trans from a second vector nucleic acid. See also, the Examples.

The particles encoded by the high efficiency packaging vector nucleic acids of the invention typically package the high efficiency packaging vector nucleic acid at a level less than 10%, and more typically less than 1%, of the level that they package a nucleic acid which has a wild-type HIV packaging site. The level of nucleic acid incorporation is optionally measured by RT-PCR. An alternative indication that the high efficiency packaging vector is not packaged into HIV particles is to co-culture cells transduced by the vector with permissive cells such as Molt-4 clone 8 cells, and test for transmission to the permissive cells. If no transmission is observed, the packaging vector nucleic acid is not packaged at a significant level. As described in the examples below, a deletion in the psi region from an HIV-$2_{KR}$ genomic clone eliminated packaging as tested by co-culture of transduced cells with permissive cell types.

Packagable Nucleic Acids

If packaging cells transduced with the high efficiency packaging nucleic acids of the invention are subsequently transduced with a vector nucleic acid which lacks coding sequences for HIV trans active functions, but includes an HIV packaging signal, the vector nucleic acid is packaged into an HIV capsid and envelope, which is capable of transducing a target cell. Packagable nucleic acids encode an RNA which is competent to be packaged by an HIV particle. Such nucleic acids can be constructed by recombinantly combining an HIV packaging site with a nucleic acid of choice. The packaging site (psi site) is located adjacent to the 5' LTR, primarily between the MSD site and the gag initiator codon (AUG) in the leader sequence of the gag gene. Thus, the minimal packaging site includes a majority of nucleic acids between the MSD and the gag initiator codon from either HIV-1 or HIV-2. Preferably, a complete packaging site includes sequences from the 5' LTR and the 5' region of gag gene for maximal packaging efficiency. When an HIV-2 packaging site is used, the first ATG of gag to the MSD is optionally included as the HIV-2 packaging site. The first 30 nucleotides of gag are optionally included as part of the HIV-2 packaging site. In some embodiments, the first 50 nucleotides of gag are included as part of the HIV-2 packaging site. Optionally, the first 75 nucleotides of gag are also included as part of the HIV-2 packaging site. The first 100 nucleotides of gag can be included as part of the HIV-2 packaging site.

Other functions of HIV replication not supplied by trans-complementation which are necessary for replication of the vector are present in the packagable vector nucleic acid. This optionally includes, e.g., the TAR sequence, the sequences necessary for HIV packaging, the RRE sequence if the instability elements of the p17 gene of gag is included, and sequences encoding the polypurine tract. HIV sequences that contain these functions include a portion of the 5' long terminal repeat (LTR) and sequences downstream of the 5' LTR responsible for efficient packaging. See, Garzino-Demo et al. (1995) *Hum. Gene Ther.* 6(2): 177–184. For a general description of the structural elements of the HIV genome, see, Holmes et al. PCT/EP92/02787.

The p17 gene contains INS (instability) elements that cause rapid degradation of the LTR promoter-mediated transcript in the absence of the Rev-RRE interaction. Therefore, if the INS sequences are included in the vector, the RRE is also typically included. However, if the HIV portion does not contain the INS sequence of p17, then the RRE sequence is optionally omitted. RRE is normally located in the envelope gene of HIV and is the sequence to which the rev protein binds.

The TAR sequence is located in the R portion of the 5' LTR. It is the sequence to which the tat protein binds. The sequences for packaging optionally include sequences from the U5 portion of the 5' LTR, downstream of it into part of p17, as well as the U3R portion of the 3' LTR. The polypurine tract is the sequence upstream from the 3' LTR site where RNAse H cleaves during plus ("+") strand DNA synthesis. It mediates plus strand synthesis.

The complete LTRs are optionally included to facilitate packaging of the packagable nucleic acid, and to permit chromosomal integration of a DNA corresponding to the packagable nucleic acid in a target cell. The target cell is any cell within the host range of HIV particle, or where the particle is pseudotyped, in the host range of the pseudotyped HIV particle.

The primate lentiviruses, including HIV-1, HIV-2 and SIV are structurally and functionally similar. Cognate portions of any of these viruses can be used in the vectors of the present invention, or in trans-complementation assays in a manner similar to that described for HIV-2.

Cellular Transduction and Gene Therapy

The present invention provides several features that allow one of skill to generate powerful retroviral cell transduction vectors. These vectors comprise an HIV-2 packagable nucleic acid packaged in an HIV-2 particle, typically using a packaging cell line of the invention. Cell transduction vectors have considerable commercial utility as a method of introducing genes into target cells. In particular, gene therapy procedures, in which the cell transduction vectors of the invention are used to transduce target cells with a therapeutic nucleic acid in an in vivo or ex vivo procedure are used to combat chronic illnesses such as HIV.

Gene therapy provides a method for combating chronic infectious diseases such as HIV, as well as non-infectious diseases such as cancer. Yu et al. (1994) *Gene Therapy* 1:13–26 and the references therein provides a general guide to gene therapy strategies for HIV infection. See also, Sodoski et al. PCT/US91/04335. One general limitation of common gene therapy vectors such as murine retroviruses is that they only infect actively dividing cells, and they are generally non-specific. In contrast, non-dividing cells are infected by HIV viruses (including HIV-$2_{KR}$), and vectors which utilize an HIV particle.

HIV based vectors are primarily used to transduce CD4$^+$ cells and hematopoietic stem cells. HIV viruses also infect a few other cell-types in vitro which exhibit little or no CD4 expression, such as peripheral blood dendritic cells, follicular dendritic cells, epidermal Langerhans cells, megakaryocytes, microglia, astrocytes, oligodendroglia, CD8$^+$ cells, retinal cells, renal epithelial cells, cervical cells, rectal mucosa, trophoblastic cells, and cardiac myocytes (see, Rosenburg and Fauci 1, supra); the infection of these cell types by HIV in vivo, however, is rare. Lists of CD4$^+$ and CD4$^-$ cell types which are infectable by HIV have been compiled (see, Rosenburg and Fauci 1 supra; Rosenburg and Fauci (1989) *Adv Immunol* 47:377–431; and Connor and Ho (1992) in *AIDS: etiology, diagnosis, treatment, and prevention*, third edition Hellman and Rosenburg (eds) Lippincott, Philadelphia).

The present invention provides HIV-2 nucleic acids and polypeptides. These nucleic acids and capsids are useful as components of gene therapy vectors. Retroviral vectors packaged into HIV envelopes primarily infect CD4$^+$ cells, (i.e., by interaction between the HIV envelope glycoprotein and the CD4 "receptor") including non-dividing CD4$^+$ cells such as macrophage. For instance, the capsid polypeptides of the present invention package gene therapy vectors which include HIV packaging sequences. Thus, in one preferred embodiment, the nucleic acids of the present invention are used in cell transduction or gene therapy vectors to package therapeutic nucleic acids into an HIV-2 particle for delivery to CD4$^+$ cells. This is accomplished by incorporating cis active nucleic acids from the nucleic acids of the present invention (e.g., promoter sequences, packaging sequences, integration or cellular targeting sequences) into the vector, or by using trans active nucleic acids and polypeptides (capsid and envelope proteins and transcription factors) to replicate and package the gene therapy vector into an HIV particle. The cis active sequences of the invention are optionally used with non-retroviral gene therapy vectors such as adeno associated virus vectors to provide, e.g., promoter, integration or cellular targeting sequences.

HIV cell transduction vectors are particularly desirable because of their ability to be pseudotyped to infect non-dividing hematopoietic stem cells (CD34$^+$). This is done by transducing the packaging cell line used to package the vector with a nucleic acid which encodes the vesicular stomatitis virus (VSV) envelope glycoprotein, which is then expressed on the surface of the HIV vector. VSV infects CD34$^+$ cells, and pseudotype HIV-2 vectors expressing VSV envelope proteins are competent to transduce these cells.

CD34$^+$ cells are important target cells for ex vivo gene therapy, because these cells differentiate into many different cell types, and because the cells are capable of re-engraftment into a patient undergoing ex vivo therapy. Stem cells differentiate in vivo into a variety of immune cells, including CD4$^+$ cells which are the primary targets for HIV infection.

HIV-2 vectors are pseudotyped by transducing packaging cell lines used to package the vector with a nucleic acid which encodes the vesicular stomatitis virus (VSV) envelope glycoprotein protein, which is expressed on the surface of the HIV particle. VSV infects both dividing and non-dividing CD34$^+$ cells, and pseudotype vectors expressing VSV envelope proteins are competent to transduce these cells. See, Naldini et al. (1996) *Science* 272:263; and Akkina et al. (1996) *J Virol* 70:2581.

One class of embodiments utilizes the LTR sequences described herein as a component of a gene therapy vector. The LTR sequences described herein are particularly useful because they have a high level of basal promoter activity in CD4 cells, and have no tat or rev requirement. The LTR sequences, in addition to binding tat and rev are responsive to cellular cytokines (such as IL-2 and SP-1) which act to permit transcription of the viral genome. Thus, in one embodiment, a therapeutic gene of choice is placed under the control of an LTR promoter of the present invention. See, e.g., Poznansky et al. (1991) *Journal or Virology* 65(1): 532–536 for a description of the region flanking the 5' LTR's ability to package vector nucleic acids.

In one preferred embodiment, the HIV-2 proviruses of the present invention are used to make retroviral vectors for gene therapy. Copending applications Ser. No. 08/245,742 (Wong-Staal et al., see also PCT application PCT/US94/05700 (WO 94/26877) and Chatterjee et al. (*Science* (1992), 258: 1485–1488, hereinafter Chatterjee et al. 1) describe anti-sense inhibition of HIV-1 infectivity in target cells using viral vectors with a constitutive expression cassette expressing anti-TAR RNA. Chatterjee et al. (PCT application PCT/US91/03440 (1991), hereinafter Chatterjee et al. 2) describe viral vectors, including AAV-based vectors which express antisense TAR sequences. Chatterjee and Wong (*Methods, A companion to Methods in Enzymology* (1993), 5: 51–59) further describe viral vectors for the delivery of antisense RNA. For a general review of gene therapy procedures, see Anderson, *Science* (1992) 256:808–813; Nabel and Felgner (1993) *TIBTECH* 11: 211–217; Mitani and Caskey (1993) *TIBTECH* 11: 162–166; Mulligan (1993) *Science* 926–932; Dillon (1993) *TIBTECH* 11: 167–175; Miller (1992) *Nature* 357: 455–460; Van Brunt (1988) *Biotechnology* 6(10): 1149–1154; Vigne (1995) *Restorative Neurology and Neuroscience* 8: 35–36; Kremer and Perricaudet (1995) *British Medical Bulletin* 51(1) 31–44; Haddada et al. (1995) in Current Topics in *Microbiology and Immunology* Doerfler and Böhm (eds) Springer-Verlag, Heidelberg Germany; and Yu et al. (1994) *Gene Therapy* 1: 13–26, and the references cited therein. Copending application Ser. No. 08/442,061, filed May 16, 1995 and PCT publication WO 94/26877 (PCT/US94/05700) describe a variety of anti-HIV therapy genes, and gene therapy strategies generally, including the use of suicide genes, trans-dominant genes, ribozymes, anti-sense genes, and decoy genes in gene therapy vectors.

Ex Vivo Therapy

Ex vivo methods for inhibiting viral replication in a cell in an organism involve transducing the cell ex vivo with a vector of this invention, and introducing the cell into the organism. The cells are CD4$^+$ cells such as CD4$^+$ T cells or macrophage isolated or cultured from a patient, or are CD34$^+$ hematopoietic stem cells.

T cells are used in some embodiments in ex vivo procedures. Several techniques are known for isolating T cells. One procedure for isolating T cells is described in Leavitt et al. *Hum. Gene Ther.* (1994) 5:1115–1120. Wong-Staal et al. WO 94/26877 also describes methods of isolating and transducing T cells. HIV inhibitors are typically added to cultures of T-cells to inhibit HIV growth when the T cells are isolated from potentially HIV-positive sources. For example, delaviridine can be added to cultures of T cells to inhibit HIV growth.

The expression of surface markers facilitates identification and purification of T cells. Methods of identification and isolation of T cells include FACS, incubation in flasks with fixed antibodies which bind the particular cell type and panning with magnetic beads.

In one embodiment, CD34$^+$ stem cells are used in ex-vivo procedures for cell transduction and gene therapy. The advantage to using stem cells is that they can be differentiated into other cell types in vitro, or can be introduced into a mammal (such as the donor of the cells) where they will engraft in the bone marrow. Methods for differentiating CD34$^+$ cells in vitro into clinically important immune cell types using cytokines such a GM-CSF, IFN-γ and TNF-α are known (see, Inaba et al. (1992) *J. Exp. Med.* 176, 1693–1702, and Szaboles et al. (1995) 154: 5851–5861). Methods of pseudotyping HIV-based vectors so that they can transduce stem cells are described above.

Stem cells are isolated for transduction and differentiation using known methods. For example, in mice, bone marrow cells are isolated by sacrificing the mouse and cutting the leg bones with a pair of scissors. Stem cells are isolated from bone marrow cells by panning the bone marrow cells with antibodies which bind unwanted cells, such as CD4$^+$ and CD8$^+$ (T cells), CD45$^+$ (panB cells), GR-1 (granulocytes), and Ia$^d$ (differentiated antigen presenting cells). For an example of this protocol see, Inaba et al. (1992) *J. Exp. Med.* 176, 1693–1702.

In humans, CD34$^+$ hematopoietic stem cells can be obtained from a variety of sources including cord blood, bone marrow, and mobilized peripheral blood. Purification of CD34$^+$ cells can be accomplished by antibody affinity procedures. An affinity column isolation procedure for isolating CD34$^+$ cells is described by Ho et al. (1995) *Stem Cells* 13 (suppl. 3): 100–105. See also, Brenner (1993) *Journal of Hematotherapy* 2: 7–17. Yu et al. (1995) *PNAS* 92: 699–703 describe a method of transducing CD34$^+$ cells from human fetal cord blood using retroviral vectors.

Freshney et al., supra and the references cited therein provide a general discussion of how to isolate and culture cells from patients. Alternatively, the cells used for ex vivo procedures can be those stored in a cell bank (e.g., a blood bank). In one class of preferred embodiments, the gene therapy vector utilizes an anti-viral therapeutic agent (e.g., suicide gene, trans-dominant gene, anti-HIV ribozyme, anti-sense gene, or decoy gene) which inhibits the growth or replication of an HIV virus, under the control of an activated HIV-2 LTR of the invention (e.g., an LTR such as the HIV-2$_{KR}$ LTR which has high basal activity). The gene therapy vector inhibits viral replication in any of those cells already infected with HIV virus, in addition to conferring a protective effect to cells which are not infected by HIV. In addition, in preferred embodiments, the vector is replicated and packaged into HIV capsids using the HIV replication machinery, thereby causing the anti-HIV therapeutic gene to propagate in conjunction with the replication of an HIV virus. Thus, an organism infected with HIV can be treated for the infection by transducing a population of its cells with a vector of the invention and introducing the transduced cells back into the organism as described herein. Thus, the present invention provides a method of protecting cells in vitro, ex vivo or in vivo, even when the cells are already infected with the virus against which protection is sought.

Vaccines and Immunogenic Compositions

A variety of vaccine constructs conferring resistance by an organism to HIV-1 and pathogenic forms of HIV-2 are provided by the present invention. In one embodiment, the HIV-$2_{KR}$ clone herein is packaged into an HIV-2 particle (capsid/envelope) and used to infect an organism. As described in the examples below, this strategy conferred resistance in live M. nemistrina to highly pathogenic strains of HIV-2. Moreover, resistance to HIV-1 is conferred upon infection of humans with HIV-2 (see, Travers et al. (1995) Science 268: 1612–1615 and related commentary by Cohen et al (1995) Science 268: 1566). Thus, the present invention provides a provirus which confers resistance to HIV-1 and HIV-2 when administered as a vaccine. Furthermore, HIV particles which lack nucleic acids, e.g., produced using a high efficiency packaging vector and a packaging cell, can be used as immunogenic compositions and vaccines.

In addition to full length clones, deletion mutants of the full-length constructs provided herein produce attenuated forms of HIV-2 which are less pathogenic than the full-length constructs. For instance, Looney and Wong-Staal (PCT/US93/12088) describe multiple gene mutants of HIV and provide strategies for attenuating HIV clones. These strategies can be applied to the clones of the present invention to produce attenuated forms of HIV-2, including attenuated forms of HIV-$2_{KR}$.

In addition to HIV-based vaccines, the present invention provides a variety of vaccines which incorporate an immunogenic fragment of an HIV polypeptide into a vaccine vector. Many vaccine vectors are known in the art. For instance, HIV sequences of the invention can be used to modify viruses that transfect host cells in the patient. Live attenuated viruses, such as vaccinia or adenovirus, are convenient alternatives for vaccines because they are inexpensive to produce and are easily transported and administered. Vaccinia vaccine vectors and methods useful in immunization protocols are described, for example, in U.S. Pat. No. 4,722,848.

Suitable viruses for use in the present invention include, but are not limited to, pox viruses, such as canarypox and cowpox viruses, and vaccinia viruses, alpha viruses, adenoviruses, adeno associated viruses and other animal viruses. The recombinant viruses can be produced by methods well known in the art, for example, using homologous recombination or ligating two plasmids to form a vaccine provirus. A recombinant canarypox or cowpox virus can be made, for example, by inserting the nucleic acids encoding HIV env polypeptides into plasmids so that they are flanked by vaccine viral vector sequences. The nucleic acids encoding the HIV env are then inserted into the virus genome through homologous recombination or by using standard cloning techniques.

A recombinant adenovirus can be produced, for example, by ligating together two plasmids each containing about 50% of the adeno virus viral sequence and the a DNA sequence encoding env. Recombinant RNA viruses such as the alpha virus can be made via a cDNA intermediate using cloning methods known in the art.

In the case of vaccinia virus (for example, strain WR), the nucleic acid sequence encoding an HIV polypeptide can be inserted in the genome by a number of methods including homologous recombination using a transfer vector, e.g., pTKgpt-OFIS as described in Kaslow et al. (1991) Science 252:1310–1313.

Alternately the nucleic acid encoding an HIV polypeptide can be inserted into another plasmid designed for producing recombinant vaccinia, such as pGS62, Langford et al. (1986) Mol. Cell. Biol. 6:3191–3199. This plasmid consists of a cloning site for insertion of foreign genes, the P7.5 promoter of vaccinia to direct synthesis of the inserted gene, and the vaccinia TK gene flanking both ends of the foreign gene.

Confirmation of production of recombinant virus can be achieved by DNA hybridization using cDNA encoding the polypeptide, by PCR (or other in vitro technique as described above), and by immunodetection techniques using antibodies specific for the expressed polypeptide. Virus stocks are prepared, e.g., by infection of cells such as HELA S3 spinner cells and harvesting of virus progeny.

A recombinant vaccine virus of the present invention can be used to induce antibodies to HIV polypeptides in mammals, such as mice, rabbits or humans, useful in a variety of in vitro assays as described above. In addition, a recombinant virus can be used to produce the polypeptide by infecting host cells in vitro, which in turn express the polypeptide (see, above).

The present invention also provides a variety of immunogenic compositions, including intact viruses, polypeptides, viral capsids, viral envelopes, viral particles and nucleic acids, all of which are encoded by the proviruses of the invention. For instance, the present invention describes the provirus HIV-$2_{KR}$, which is optionally encapsidated in a viral capsid and/or a viral envelope. HIV-$2_{KR}$ also encodes peptides and nucleic acids which are themselves immunogenic. These immunogenic peptides and nucleic acids are optionally incorporated into immunogenic vectors as described above, or are optionally used as immunogenic or immunodetective reagents. Any of these compositions encoded by the provirus HIV-$2_{KR}$ can be administered, preferably with an immunogenic adjuvant to raise antibodies and antisera in mice, rabbits, humans, macaques and other mammals. Many methods for the generation of antibodies and antisera are known. See, Coligan, Harlow and Lane, Stites et al., Goding, Kohler and Milstein, Huse et al. and Ward (all supra). These antibodies are useful as diagnostic reagents to detect HIV in biological samples.

In Vivo Therapy and Vaccination

Gene therapy vectors containing nucleic acid or polypeptide sequences of the invention can be administered directly to the organism for transduction of cells in vivo. In addition, the viruses of the present invention, or immunogenic or recombinant forms thereof can also be administered directly to an organism to confer resistance to HIV infection. As discussed herein, HIV-2 infection dramatically reduces the infection rate of an organism by HIV-1. As discussed in the examples herein, infection of an organism with the non-pathogenic HIV strains provided in this invention prevent infection of the organism by pathogenic strains of HIV. Examples of retroviral packaging cells, HIV-2 packagable nucleic acids and packaging systems for making pseudotype vectors are provided.

Administration of gene therapy vectors, cells transduced ex vivo, and HIV vaccines can be by any of the routes normally used for introducing a cell or molecule into ultimate contact with blood or tissue cells. As described herein, preferred vectors and vaccines utilize HIV viral particles, but other arrangements are also feasible, such as adeno-associated capsids (see, Ser. No. 08/442,061), polypeptides, and any of the numerous vaccine vectors known in the art (see, supra). Gene therapy vectors and vaccines of the present invention can be used to treat and prevent virally-mediated diseases such as AIDS in patients. The vectors, transduced cells, or vaccines are administered in any suitable manner, preferably with pharmaceutically acceptable carriers. Suitable methods of administering such vectors and vaccines in the context of the present invention to a patient are available, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention.

Formulations suitable for oral administration can consist of (a) liquid solutions, such as an effective amount of the vector dissolved in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art.

The vectors and vaccines, alone or in combination with other suitable components, can be made into aerosol formulations to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the vector with a suppository base. Suitable suppository bases include natural or synthetic triglycerides or paraffin hydrocarbons. In addition, it is also possible to use gelatin rectal capsules which consist of a combination of the vector with a base, including, for example, liquid triglyercides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Parenteral administration the preferred method of administration. The formulations of vector can be presented in unit-dose or multi-dose sealed containers, such as ampules and vials, and in some embodiments, can be stored in a freeze-dried (lyophilized) condition requiring only the addition of the sterile liquid carrier, for example, water, for injections, immediately prior to use. For many vectors, this mode of administration will not be appropriate, because many virions are destroyed by lyophilization. Other vectors (e.g., vectors utilizing an AAV capsid) tolerate lyophilization well.

Extemporaneous injection solutions and suspensions can be prepared from sterile powders, granules, and tablets of the kind previously described. Cells transduced by the vector as described above in the context of ex vivo therapy can also be administered parenterally as described above, except that lyophilization is not generally appropriate, since cells are destroyed by lyophilization.

The dose administered to a patient, in the context of the present invention should be sufficient to effect a beneficial therapeutic response in the patient over time, or to inhibit infection by a pathogenic strain of HIV. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, vaccine, or transduced cell type in a particular patient. In determining the effective amount of the vector to be administered in the treatment or prophylaxis of virally-mediated diseases such as AIDS, the physician needs to evaluate circulating plasma levels, vector toxicities, progression of the disease, and, in the case of vaccine compositions, the production of anti-HIV antibodies. In general, the dose of a naked nucleic acid composition such as a DNA vaccine or gene therapy vector is from about 1 $\mu$g to 100 $\mu$g for a typical 70 kilogram patient.

In ex vivo procedures, prior to infusion of transduced cells, blood samples are obtained and saved for analysis. Between $1 \times 10^6$ and $1 \times 10^{10}$ transduced cells are typically infused intravenously over 60–200 minutes. Vital signs and oxygen saturation by pulse oximetry are closely monitored. Leukopheresis, transduction and reinfusion may be repeated every 2 to 3 months for a total of 4 to 6 treatments in a one year period. After the first treatment, infusions can be performed on a outpatient basis at the discretion of the clinician. If the reinfusion is given as an outpatient, the participant is generally monitored for 4 to 8 hours or more following the therapy.

Transduced cells are prepared for reinfusion according to established methods. See, Abrahamsen et al. (1991) *J. Clin. Apheresis* 6:48–53; Carter et al. (1988) *J. Clin. Apheresis* 4:113–117; Aebersold et al. (1988), *J. Immunol. Methods* 112: 1–7; Muul et al. (1987) *J. Immunol. Methods* 101:171–181 and Carter et al. (1987) *Transfusion* 27:362–365. After a period of about 2–4 weeks in culture, the cells may number between $1 \times 10^6$ and $1 \times 10^{10}$. In this regard, the growth characteristics of cells vary from patient to patient and from cell type to cell type. About 72 hours prior to reinfusion of the transduced cells, an aliquot is taken for analysis of phenotype, and percentage of cells expressing the therapeutic agent.

If a patient undergoing infusion of a vector or transduced cell develops fevers, chills, or muscle aches, he/she receives the appropriate dose of aspirin, ibuprofen or acetaminophen. Patients who experience reactions to the infusion such as fever, muscle aches, and chills are premedicated 30 minutes prior to the future infusions with either aspirin, acetaminophen, or diphenhydramine. Meperidine is used for more severe chills and muscle aches that do not quickly respond to antipyretics and antihistamines. Cell infusion is slowed or discontinued depending upon the severity of the reaction.

In the practice of this invention, compositions can be administered, for example, by intravenous infusion, orally, topically, intraperitoneally, intravesically or intrathecally. The preferred method of administration will often be oral, rectal or intravenous, but the vectors can be applied in a suitable vehicle for the local and topical treatment of virally-mediated conditions. The vectors of this invention can supplement treatment of virally-mediated conditions by any known conventional therapy, including cytotoxic agents, nucleotide analogues and biologic response modifiers.

For administration, vectors, vaccines and transduced cell types of the present invention can be administered at a rate determined by the LD-50 of the vector, vaccine, or transduced cell type, and the side-effects of the vector or cell type at various concentrations, as applied to the mass and overall health of the patient. Administration can be accomplished via single or divided doses.

Anti-viral Agents

The gene therapy vectors of this invention typically include at least one "anti-viral agent" or "viral inhibitor" operably linked to an expression control sequence (such as an LTR of the invention). As used herein the terms "anti-viral agent" and "viral inhibitor" refer to any nucleic acid whose product, upon transcription or translation, inhibits the replication of a specified virus. Anti-viral agents are known in the art. The literature describes such genes and their use. See, for example, Yu et al., (1994) *Gene Therapy,* 1:13; Herskowitz (1987) *Nature,* 329:212 and Baltimore (1988) *Nature,* 335:395. Anti-viral agents useful in this invention include, without limitation, anti-sense genes, ribozymes, decoy genes, transdominant genes/proteins and suicide genes.

(i) Antisense genes

An antisense nucleic acid is a nucleic acid that, upon expression, hybridizes to a particular mRNA molecule, to a transcriptional promoter or to the sense strand of a gene. By hybridizing, the antisense nucleic acid interferes with the transcription of a complementary nucleic acid, the translation of an mRNA, or the function of a catalytic RNA. Antisense molecules useful in this invention include those that hybridize to HIV genes and gene transcripts. Two target sequences for antisense molecules are the first and second exons of the HIV genes tat and rev. Chatterjee and Wong, supra, and Marcus-Sekura (*Analytical Biochemistry* (1988) 172, 289–285) describe the use of anti-sense genes to block or modify gene expression.

(ii). Ribozymes

A ribozyme is a catalytic RNA molecule that cleaves other RNA molecules having particular nucleic acid sequences. Ribozymes useful in this invention are those that cleave HIV gene transcripts. Ojwang et al. (1992) *Proc. Nat'l. Acad. Sci., U.S.A.* 89:10802–10806 provide an example of an HIV-1 pol-specific hairpin ribozyme. Wong-Staal et al. PCT/US94/05700 (WO 94/26877) provide examples of hairpin and hammerhead ribozymes (e.g., those which cut at the sequence GUX). A hammerhead ribozyme directed against the sequence 5'-CAGGAA<u>GTCA</u> GCCTAAGA-3' (SEQ ID NO: 27) in the first exon of tar has the sequence: 5'-UCUUAGGCU [CUGAUGAGUC CGUGAGGACG AA] GACUUCCUG-3'(SEQ ID NO: 28).

(iii). Decoy Nucleic Acids

A decoy nucleic acid is a nucleic acid having a sequence recognized by a regulatory nucleic acid binding protein (i.e., a transcription factor). Upon expression,the transcription factor binds to the decoy nucleic acid, rather than to its natural target in the genome. Useful decoy nucleic acid sequences include any sequence to which a viral transcription factor binds. For instance, the TAR sequence, to which the tat protein binds, and HIV RRE sequence, to which the rev proteins binds are suitable sequences to use as decoy nucleic acids. Thus, most gene therapy vectors containing the HIV LTRs of the present invention serve as decoy nucleic acids.

(iv). Transdominant Proteins

A transdominant protein is a protein whose phenotype, when supplied by transcomplementation, will overcome the effect of the native form of the protein. For example, tat and rev can be mutated to retain the ability to bind to TAR and RRE, respectively, but to lack the proper regulatory function of those proteins. In particular, rev can be made transdominant by eliminating the leucine-rich domain close to the C terminus which is essential for proper normal regulation of transcription. Tat transdominant proteins can be generated by mutations in the RNA binding/nuclear localization domain.

(v). Suicide Genes

A suicide gene produces a product which is cytotoxic. In the gene therapy vectors of the present invention, a suicide gene is operably linked to an expression control sequence in the vector which is stimulated upon infection by HIV (e.g., an LTR which requires tat for activation in a vector which does not encode tat). Upon infection of the cell by competent virus, the suicide gene product is produced, thereby killing the cell and blocking replication of the virus.

Examples of antisense molecules, ribozymes and decoy nucleic acids and their use can be found in Weintraub (Jan. 1990) *Sci. Am.* 262:40–46; Marcus-Sekura (1988) *Anal. Biochem.* 172:289–95; and Hasselhoff et al. (1988) *Nature* 334:585–591.

Discussion of the Accompanying Sequence Listing

SEQ ID NO: 1 provides the complete sequence of the HIV-2 provirus HIV-$2_{KR}$. The information is presented as a DNA sequence (i.e., the sequence of the HIV-$2_{KR}$ provirus as it appears, e.g., cloned in a bacterial plasmid). One of skill will readily understand that the sequence also describes the full-length genomic RNA of HIV-$2_{KR}$ (i.e., by substitution of the T residues with U residues) and a variety of conservatively modified variations of the sequence provided. SEQ ID NO: 10 and SEQ ID NO: 11 provide subsequences of the full-length HIV-$2_{KR}$ sequence comprising the nucleic acid sequences encoding the HIV genes nef and vif, respectively. SEQ ID NO: 12 provides the sequence of the 5' HIV-$2_{KR}$ LTR. SEQ ID NO: 13–15 provide subsequences of the full-length HIV-$2_{KR}$ sequence comprising the nucleic acid sequences encoding the HIV genes env, pol, and rev. SEQ ID NO: 16 provides the HIV rev1 subsequence. One of skill will readily understand that each of the subsequences of the HIV-$2_{KR}$ sequence also describe the full-length genomic RNA of HIV-$2_{KR}$ (i.e., by substitution of the T residues with U residues) and a variety of conservatively modified variations of the sequences provided.

SEQ ID NO: 2 provides the amino acid sequence of the env protein encoded by HIV-$2_{KR}$. SEQ ID NO: 3 provides the amino acid sequence of the gag protein encoded by HIV-$2_{KR}$. SEQ ID NO: 4 provides the amino acid sequence of the nef protein encoded by HIV-$2_{KR}$. SEQ ID NO: 5 provides the amino acid sequence of the pol protein encoded by HIV-$2_{KR}$. SEQ ID NO: 6 provides the amino acid sequence of the rev protein encoded by HIV-$2_{KR}$. SEQ ID NO: 7 provides the amino acid sequence of the tat protein encoded by HIV-$2_{KR}$. SEQ ID NO: 8 provides the amino acid sequence of the vif protein encoded by HIV-$2_{KR}$. SEQ ID NO: 9 provides the amino acid sequence of the vpr protein encoded by HIV-$2_{KR}$. A variety of conservatively modified variations of the amino acid sequences provided will be apparent to one of skill, and one of skill will recognize that a variety of nucleic acid sequences encode each of the polypeptides due to the codon degeneracy present in the genetic code.

SEQ ID NOS: 17–26 describe exemplar oligonucleotides derived from the HIV-2 proviruses of the invention.

EXAMPLES

The following examples are provided by way of illustration only and not by way of limitation. Those of skill will readily recognize a variety of noncritical parameters which can be changed or modified to yield essentially similar results.

Example 1

Isolation and Charactetization of HIV-$2_{KR}$

A lambda-phage clone containing a full-length HIV-2 provirus, designated HIV-$2_{KR}$, was obtained from the genomic DNA of Molt 4 Clone 8 (Molt-4/8) lymphoblastic cells infected with the HIV-$2_{PEI2}$ strain, isolated from the peripheral blood mononuclear cells of a single HIV-2 seropositive AIDS patient. HIV-$2_{KR}$ is distinct from all known HIV-2 isolates, possessing, inter alia, both a unique deletion in the LTR promoter region, and a long rev reading frame uncommon among HIV-2 sequences. HIV-$2_{KR}$ is replication competent in vitro, producing p26 protein and infectious progeny virions after direct transfection into Molt-4/8 cells, and in vivo in Macaques. Like the parental HIV-$2_{PEI2}$ isolate, HIV-$2_{KR}$ replicated in a variety of established human T-cell (Molt-4/8, SupT1, H9, C8166) and myelomonocytic (U937) cell lines, and displayed cytopathic effects upon infection of Molt-4/8 cells. In addition, HIV-$2_{KR}$ was found to be infectious for primary human and macaque lymphocytes, and primary human monocyte-macrophage cultures. Intravenous inoculation of cell-free HIV-$2_{KR}$ into *Macaca nemestrina* resulted in persistent low-level infection, with transient viremia and a transient decline in CD4 lymphocyte numbers. HIV-$2_{KR}$ also provided protection against more pathogenic strains of HIV-2 in *M. nemestrina.*

Growing Plasmid D53 Deposited with the ATCC

The HIV-$2_{KR}$ genome was deposited with the ATCC on Jul. 26, 1995. The form of the deposit is as a plasmid (D53) which contains the complete HIV-$2_{KR}$ genome, as well as an ampicillin selectable marker gene. An aliquot of the plasmid can be obtained from the ATCC. The plasmid can be transformed into DH5α *E. Coli* and plated onto LB-Amp agar plates. Colonies are then picked and grown in standard LB-amp media at 37° C. through late log phase growth (0.6 to 0.7 OD at $600_{mn}$), harvested, and the plasmid DNA is purified. The plasmid is verified, e.g., by restriction analysis (See, FIG. 5 for a restriction map of the D53 plasmid, see also, SEQ ID NO: 1 for the sequence of the HIV-$2_{KR}$ proviral portion of the plasmid). See, Sambrook for a description of experimental protocols suitable for growing and harvesting cells, plasmid DNA purification, and restriction analysis.

Materials and Methods

The following materials and methods were used in Example 1. Molecular cloning of proviral HIV-2 DNA. Genomic DNA was extracted from Molt-4/8 cells from a patient chronically infected with HIV-$2_{PEI2}$ (see, Kirchhoff, et al. (1990) *Aids* 4, 847–57 for a general description of the method). After partial digestion with Sau3A, 9–20 kb fragments were ligated to EMBL-4 arms. The ligated DNA was packaged into phage using Stratagene Gigapack™ Gold extract. The genomic library was screened by using a pol probe derived from HIV-$2_{ISY}$. One hybridization positive λ-phage clone was found to contain a complete provirus (designated HIV-$2_{KR}$). The insert DNA was subcloned into two plasmids. Plasmid pRTsac, containing the 3' portion of the provirus, was created by cloning a Sac I fragment extending from a site in HIV-$2_{KR}$ tat to a site in the 3' cellular flank into the Sac I site of pUC19c. Plasmid pKTM, containing the 5' portion of the provirus, was created by first cloning a proviral EcoRI—SacI fragment into pSVL opened with EcoRI and SacI, and then cloning a EcoRI fragment containing a fragment extending from the 5' cellular flank to the proviral EcoRI site into the EcoRI site of the first plasmid (only the correct orientation was observed after ligation). The viral sequence was obtained by dideoxynucleotide chain termination double-strand sequencing (BioRad DNA sequencing kit). Sequences were read and entered manually. Sequence data was analyzed using hierarchical multiple sequence alignment and FASTA similarity comparisons (Corpet, et al. (1988) *Nucleic Acids Research* 16, 10881–90; Huang, et al. (1992) *Computer Applications in the Biosciences* 8, 155–65; Pearson, et al. (1994) *Methods in Molecular Biology* 24, 307–31).

HIV-2 and HIV-1 LTR Reporter Plasmids. Plasmid pC15CAT (Arya, et al. (1985) *Science* 229, 69–73) contains a Hind III fragment of the HIV-$1_{IIIB}$ LTR driving the bacterial chloramphenicol acetyl transferase (CAT) gene. Plasmid HIV2CAT (Kumar, et al. (1990) *Journal of Virology* 64, 890–901) contains the U3 and R portions of the HIV-$2_{ST}$ LTR upstream of the CAT. Reporter construct pCV-KRLTR was created by cloning an 840 bp PCR amplified fragment (including the complete U3 & R regions and all but 104 bp of the U5 region of the HIV-$2_{KR}$ LTR, sequences −534 to +288 from the transcription start site) of the HIV-$2_{KR}$ LTR into the Hind III site of pCV-LTR-basic (Promega). Primers used were (Left) 5'-gca-agc-ttg-gga-tgg-gat-gta-tta-cag-3' (SEQ ID NO: 17) and (Right) 5'-cca-agc-ttc-tgc-tag-gta-ttt-tcc-cgc-t-3'(SEQ ID NO: 18).

Choramphenicol Acetyl Transferase Assay. This assay was performed according to standard techniques (Arya, et al. (1985) *Science* 229, 69–73). Briefly, 48 hours after cationic lipid (DoTap™, Boehringer Mannheim) transfection of 1.5× $10^6$ cells with 5 mg of reporter plasmid, cells were washed three times in phosphate buffered saline, pelleted at 4° C., resuspended in 150 ml 0.25M Tris pH 7.8, subjected to three cycles of freeze thawing in dry ice—ethanol bath and vortexed for 30 seconds. The extract was cleared of debris by low speed centrifugation (15 minutes, 12000 RPM, 4° C.). For EIA determination of CAT activity, 75 ml of extract was serially diluted and tested according to the manufacturers directions (Promega). To determine the effect of various stimuli on promoter activity, cells were treated immediately after transfection with GM-CSF (8 ng/ml, Genzyme) and LPS (10 ng/ml *Salmonella typhimurium* lipopolysaccharide, Sigma), PHA-P and PMA (2 mg/ml and $10^{-8}$M respectively).

Virus Propagation In Human Primary Cells And Permanent Cell Lines. Human T-lymphocytic cell lines were propagated in RPMI 1640 supplemented with 10% fetal calf serum (FCS), 200 mM L-glutamine, and penicillin/streptomycin. Human peripheral blood lymphocytes (PBMCs) and human monocyte macrophages were isolated from healthy donors as previously described (Fisher, et al. (1988) *Nature* 334, 444–447). The PBMCs were stimulated with 2.5 μg of phytohemagglutamin per ml in RPMI 1640 supplemented with 10% FCS three days before infection. Monocytes were prepared from heparinized peripheral blood by Ficoll-Hypaque separation, low-speed centrifugation through heat-inactivated FCS, and separation of adherent cells in fibronectin coated (2 mg/ml) 162 $cm^2$ flasks for one hour. Adherent cells were detached at 4° C. using calcium-free phosphate-buffered saline with 1 mM EDTA, and replated at a density of $10^6$ cells/cm$^2$ in 24-well tissue culture plates coated with autologous serum in medium containing 10% FCS, 10% autologous serum, 10% endothelial cell conditioned medium.

DNA Transfection In Permanent T Cells Lines. Molt4/8 cells ($3 \times 10^6$) were used for transfections. Phage DNA or ligated KTM-RTsac proviral DNA (1–2 μg viral DNA) was transfected into using cationic lipid transfection (DOTAP™). The cells were cultured in 10 ml RPMI 1640 medium. Every two days 50% of the medium was replaced. Viral production was monitored by testing for p26 in the cell supernatant (Coulter™ SIV EIA).

Immunoprecipitation Of Viral Proteins. HIV-2$_{KR}$ infected cells were starved in methionine and cysteine free medium. After one hour the cells were incubated in medium supplemented with 200 mCi/ml each $^{35}$S-Methionine and $^{35}$S-Cysteine for six hours. The cells were washed three times in PBS and lysed in RIPA buffer (5 mM Tris-HCl/50 mM NaCl/0.1% SDS/1% TritonX-100/1% deoxycholic acid/1 mM phenylmethylsulfonyl fluoride). The cell lysate was centrifuged at 12000×g, 4° C., for 30 min. and the supernatant was transferred to a new tube. Aliquots of the supernatant were incubated with sera from HIV-1 and HIV-2 infected patients and the immune complexes were isolated with S. aureus protein A bound to Sepharose. After incubation, the samples were washed five times with RIPA-buffer and electrophoresed on a 11.5% SDS/polyacrylamide gel. The gel was dried and immunoprecipitated bands visualized using autoradiography.

Western Blotting. Supernatant from Molt 4/Clone 8 cells infected with HIV-2KR was cleared by low-speed centrifugation (2000×g for 20 minutes) and virus pelleted at 100,000×g for one hour at 4° C. (45Ti rotor). The pellet was resuspended in Hank's balanced salt solution and centrifuged over a discontinuous RNAase free sucrose gradient (20%–40% w/v) at 100,000×g for one hour (50Ti rotor). The interphase was collected, resuspended in sample buffer (5×sample buffer: 325 mM Tris, 10% SDS, 50% glycerol, 0.05% bromphenol blue, 20% β-mercaptoethanol) and samples run on a 10.5% polyacrylamide gel. After electrophoretic transfer to nitrocellulose, strips were blocked with 0.65% Tween 20, and incubated overnight with pooled HIV-1 (9 donors) or HIV-2 (courtesy P. Kanki) seropositive sera at a 1:100 dilution. Strips were then incubated with goat antihuman horseradish peroxidase conjugate and blots developed with diaminobenzidine.

Viral Quantitation and Infection of M. nemestrina. Infectious virus supernatant was harvested from transfected Molt-4/8 cells, cleared by low speed centrifugation, aliquoted, and stored in liquid nitrogen. Concentrated viral stocks were made by ultracentrifugation of cleared virus supernatant (200×). Viral pools were titered on HeLa CD4 (HT4–6C), Molt 4/Clone 8 cells, and human and M. nemestrina PBMC. Coulter™ SIV p26 EIA kits were used to quantitate viral antigen in infection experiments. Juvenile M. nemestrina were infected with 1000 HT4–6C syncytia forming units (SFU) by intravenous injection, unless otherwise stated.

Polymerase Chain Reaction. Integrated provirus was detected in DNA extracted from the PBMC of infected M. nemestrina using nested PCR. Amplification was carried out for 35 cycles (30" at 94° C., 60" at 55° C., 60" at 74° C.) for each primer-pair. Primer pairs used for HIV-2 env were GR72 (outside, left) 5'-ATG-TGG-ACT-AAC-TGC-AGA-GGA-GAA-T-3' (SEQ ID NO: 19), GR81 (outside, right): 5'-ATC-CAG-GAG-GTT-AAA-TCA-AAC-CAG-T-3' (SEQ ID NO: 20), GR7 (inside, left): 5'-GGG-ATC-GAT-TGA-AAT-AAC-ACC-AAT-TGG-CTT-CG-3' (SEQ ID NO: 21), and GR8 (inside, right): 5'-GGG-ATC-GAT-CAT-AGT-ACA-GTG-GTG-TAG-CAG-AC -3' (SEQ ID NO: 22). Primer pairs used for HIV-2 nef were NEF9216 (outside, left): 5'-CCA-GCT-GAT-TCG-CCT-CTT-G-3' (SEQ ID NO: 23), NEF10018 (outside, right): 5'-CCT-TCT-GGA- AAG-TCC-CTG-C-3' (SEQ ID NO: 24), NEF253 (inside, left): 5'-AAC-AAA-ATA-TGG -ATG-ATG-TAG-ATG-C-3' (SEQ ID NO: 25), and NEF360 (inside, right): 5'-TAG-AAA-ATG-TGA-TAT-ATC-TAC-TGC-C-3' (SEQ ID NO: 26).

Molecular Cloning And DNA Sequence Of The Complete HIV-2$_{KR}$ Provirus

A recombinant λ-phage containing a complete provirus was obtained from a genomic library constructed from the DNA of Molt-4/Clone 8 cells from a patient infected with HIV-2$_{PEI2}$ using a $^{32}$P labelled probe derived from the HIV-2$_{SBL\text{-}ISY}$ pol region. One positive clone containing the full length viral DNA was selected and designated HIV-2$_{KR}$. This clone contained both LTR's as well as 5' and 3' cellular flanking sequences. Restriction enzyme analysis demonstrated that HIV-2$_{KR}$ was distinct previously described HIV-2 isolates.

Figure 1A:
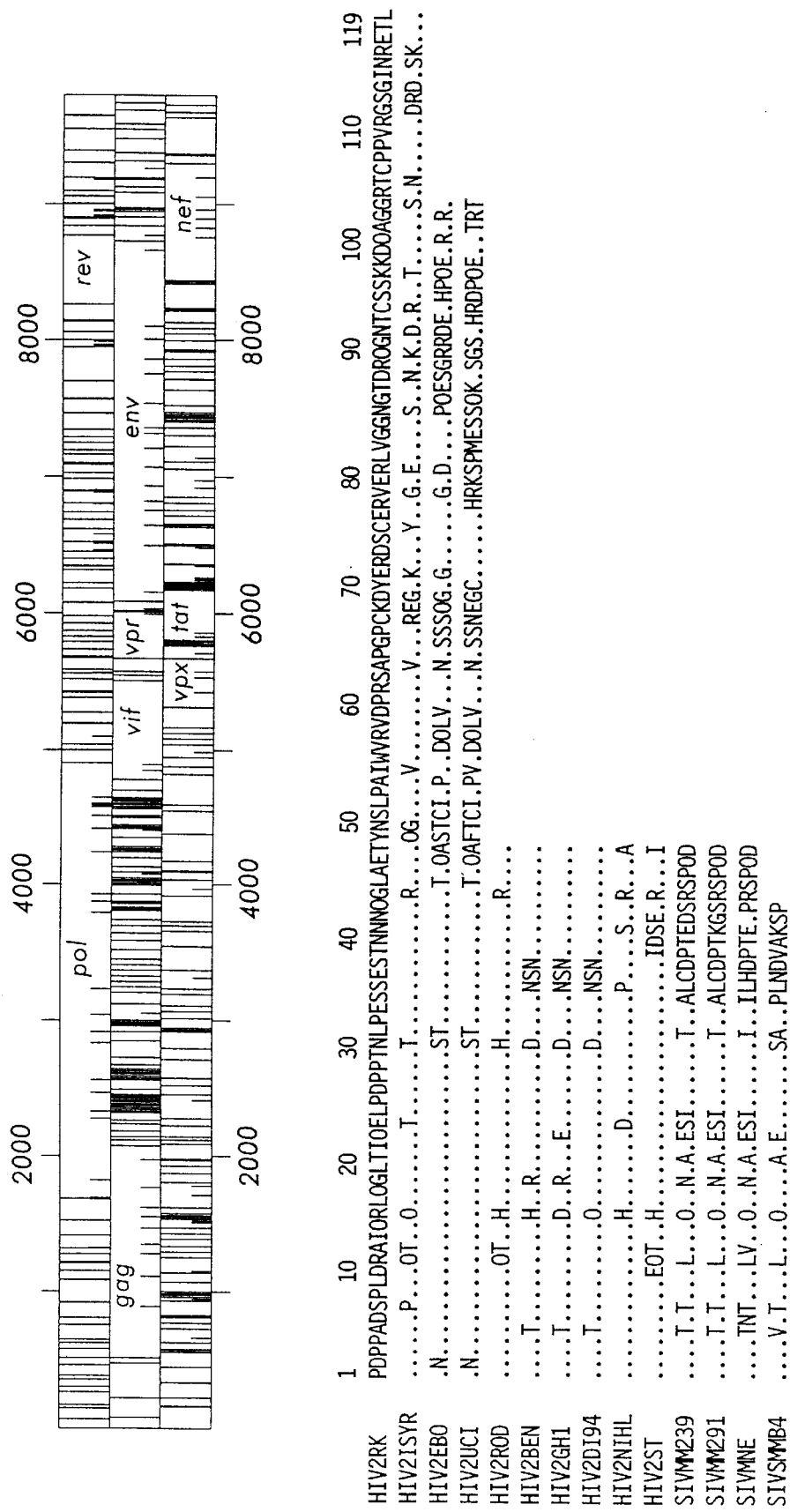
Figure 1C:
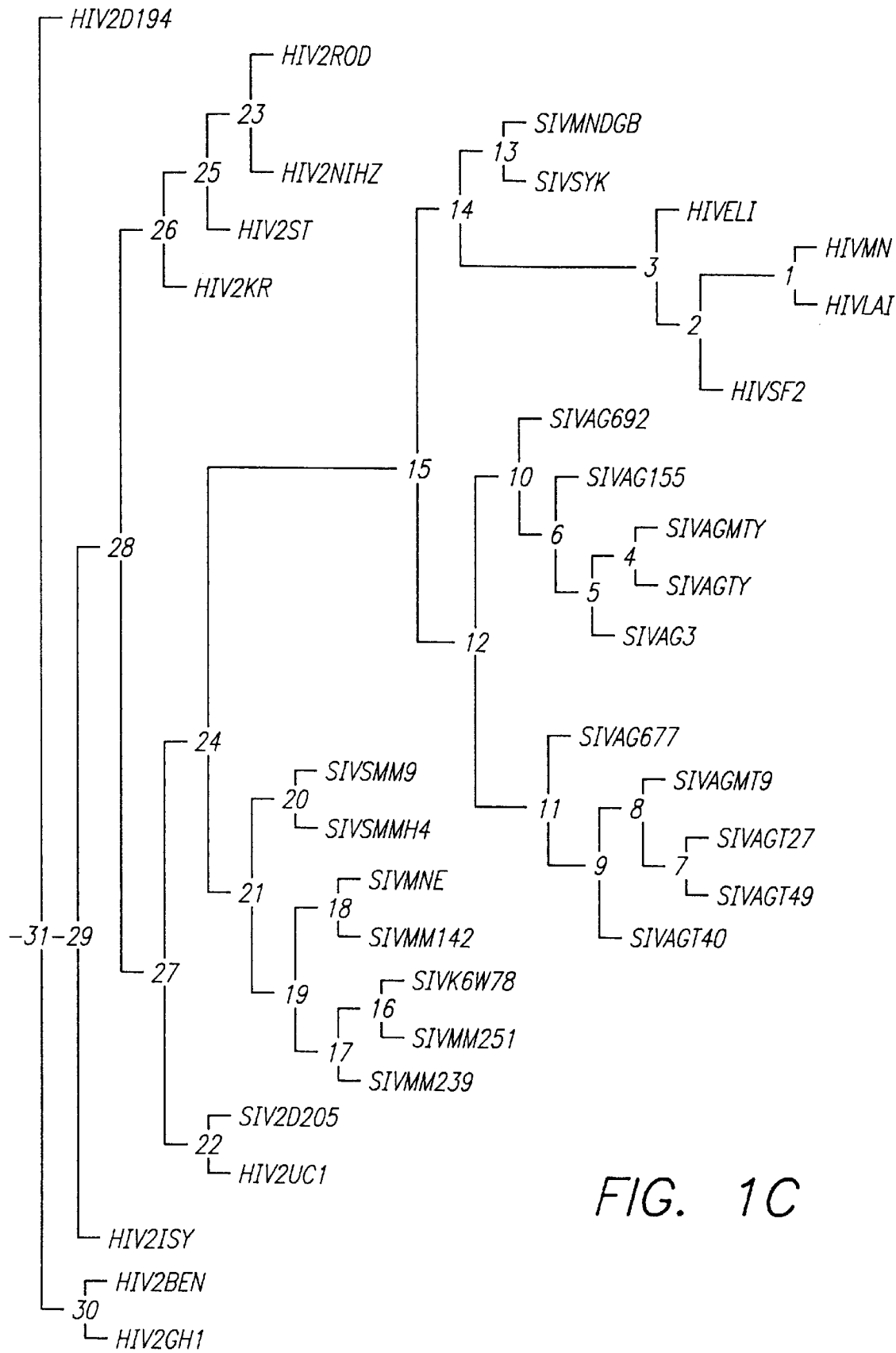

The complete nucleotide sequence of the proviral DNA was obtained, and compared with those of other HIV-2 isolates. Analysis of the open reading frames (orfs) of HIV-2$_{KR}$ revealed a genetic organization similar to that of previously characterized HIV-2 isolates (FIG. 1A). Open reading frames corresponding to the nine previously identified HIV-2 viral genes were all present. The sequences of the HIV-2$_{KR}$ env and nef genes do not show premature stop codons. Alignments of predicted amino acid sequences of viral proteins were performed using a hierarchical multiple alignment technique (Corpet, et al. (1988) Nucleic Acids Research 16, 10881–90; Huang, et al. (1992) Computer Applications in the Biosciences 8, 155–65), and the homology of HIV-2$_{KR}$ to other HIV-2 viruses (Andreasson, et al. (1993) Aids 7, 989–93; Clavel, et al. (1986) Nature, 324, 691–695; Gao, et al. (1992) Nature 358, 495–9; Naucler, et al. (1991) Aids 5, 301–4; O'Brien, et al. (1991) Aids 5, 85–8; Castro, et al. (1990) Virology 178, 527–34; Kirchhoff, et al. (1990) Aids 4, 847–57; Kuhnel, et al. (1989) Proc. Natl. Acad. Sci. U.S.A. 86, 2383–2387; Kumar, et al. (1990) Journal of Virology 64, 890–901; Zagury, et al. (1988) Proc. Natl. Acad. Sci. U.S.A. 85, 5941–5945; Franchini, et al. (1989) Proc. Natl. Acad. Sci. U.S.A. 86, 2433–2437; Barnett, et al. (1993) Journal of Virology 67, 1006–14) was calculated using the FASTA algorithm (Pearson, et al. (1994) Methods in Molecular Biology 24, 307–31) (FIG. 1B). For comparison, SIV$_{AGM}$ and HIV-1$_{BRU}$ sequences were also included. The nucleotide sequence of HIV-2$_{KR}$ is more similar to that of other HIV-2 sequences (89–94% homology) than to SIV$_{AGM}$ (70% homology), or HIV-1 (59% homology.) The greatest similarity with other HIV-2 viruses was present in the gag gene (93–98%), while the greatest average divergence was surprisingly seen in the nef and pol genes. Phylogenetic analysis of gag coding sequences using the neighbor-joining method (Felsenstein, et al. (1988) Annual Review of Genetics 22, 521–65) (FIG. 1C) revealed that HIV-2$_{KR}$ clustered closely with HIV-2$_{ROD}$, HIV-2$_{NIHz}$, and HIV-2$_{ST}$ (1–2 map units), moderately closely to HIV-2$_{ISY}$ (3 map units), less closely to HIV-2$_{D194}$, HIV-2$_{BEN}$ and HIV-2$_{GHI}$ (5–6 map units), and least closely with HIV-2$_{UCI}$ (8 map units).

Several distinctive molecular features were identified. First, as for HIV-2$_{ISY}$ (SEQ ID NO: 30), HIV-2$_{UCI}$ (SEQ ID NO: 32), HIV-2$_{EHO}$ (SEQ ID NO: 31), the second coding exon of the KR rev gene is considerably larger than other HIV-2 rev reading frames (471 bp, 180 amino acid residues), extending an additional 72 residues further than the rev proteins of HIV-2$_{ROD}$ (SEQ ID NO: 33), HIV-2$_{BEN}$ (SEQ ID NO: 34), HIV-2$_{GH1}$(SEQ ID NO: 35), HIV-2$_{D194}$ (SEQ ID NO: 36), HIV-2$_{NIHZ}$ (SEQ ID NO: 37), HIV-2$_{ST}$ (SEQ ID NO: 38), SIV$_{MM239}$ (SEQ ID NO: 39), SIV$_{MM251}$ (SEQ ID NO: 40), or SIV$_{MNE}$ (SEQ ID NO: 41)(see FIG. 1A, lower section). Secondly, a deletion of 9–10 bp (depending on alignment parameters) corresponding to approximately a single turn of the DNA helix is noted in the LTR (FIG. 2A) just before the SpI binding sites. This deletion is not seen in other HIV-2 isolates, and is not similar to the NFkB duplication (Novembre, et al. (1991) *Journal of Medical Primatology* 20, 188–92) previously described in the SIV$_{MMpbj}$ LTR.

Transcriptional Activity of the HIV-2$_{KR}$ LTR.

Figure 2B:
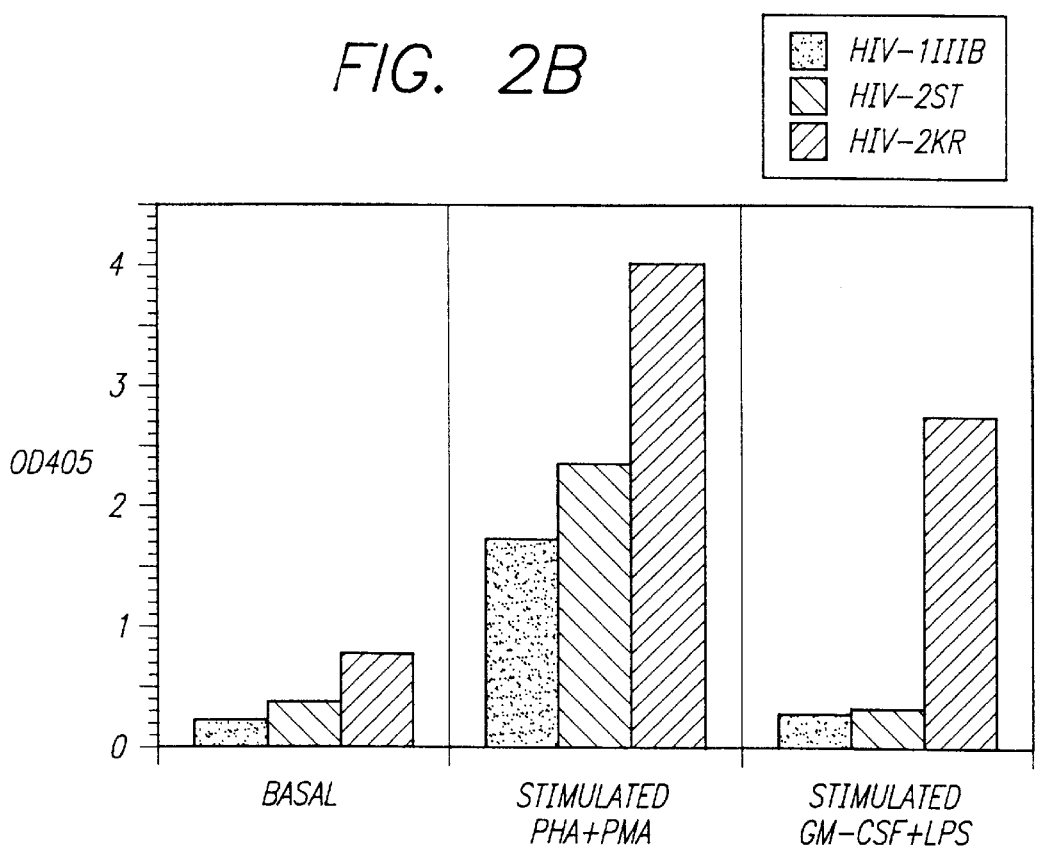

To determine if the unique deletion in the HIV-2$_{KR}$ LTR affected transcriptional activity, a reporter plasmid was constructed using a promoterless pCV based construct containing the chloramphenicol acetyltransferase gene (see, Material and Methods). The basal and stimulated transcriptional activity of the HIV-2$_{KR}$ plasmid was then compared with that of similar reporter constructs (Arya, et al. (1985) *Science* 229, 69–73; Kumar, et al. (1990) *Journal of Virology* 64, 890–901) containing the HIV-1$_{IIIB}$ LTR and the HIV-2$_{ST}$ LTR in a transient transfection assay using U937 cells. As seen in FIG. 2B, the basal activity of the HIV-2$_{KR}$ LTR was twofold that of HIV-2$_{ST}$, and 3-fold that of the HIV-1$_{IIIB}$ LTR. This increased activity was also evident after stimulation with PHA and PMA (FIG. 2B, second panel). Only the HIV-2$_{KR}$ LTR exhibited significant transactivation after simulation with GM-CSF and LPS (FIG. 2B, third panel). The U3 promoter regions of the HIV-2$_{KR}$ and HIV-2$_{ST}$ LTR included in the reporter plasmids are essentially identical except for a 24 bp region containing this 9 bp deletion (see FIG. 2A.) The biological significance of the greater basal activity of the HIV-2$_{KR}$ LTR was demonstrated by the construction of a fully replicative HIV-2$_{KR}$ mutant deleted of the first coding exon of tat.

Replication and Biological Activity Of HIV-2$_{KR}$.

The recombinant λ-phage DNA, containing the complete HIV-2$_{KR}$ provirus was transfected into Molt-4/8 cells. The supernatant of the transfected cells were monitored for p26 core antigen. Giant multinucleated cells appeared in the transfected Molt-4/8 cultures about 7–10 days post transfection concurrent with the detection of p26 antigen in the supernatant. Radioimmunoprecipitation of $^{35}$S-Cysteine and methionine labeled HIV-2$_{KR}$ infected cells and western blotting of single-banded HIV-2$_{KR}$ viral pellets performed using human sera from HIV-1 and HIV-2 seropositive individuals revealed production of all structural viral proteins (Castro, et al. (1990) *Virology* 178, 527–34). A typical pattern of cross-reactivity was demonstrated by the HIV-1 positive sera, which detected only the HIV-2$_{KR}$ p26 protein. Infected Molt-4/8 cultures producing HIV-2$_{KR}$ were expanded and supernatants harvested to obtain characterized pools of cell free virus and virus antigen (see, Material and Methods), for further experiments.

Figure 3:
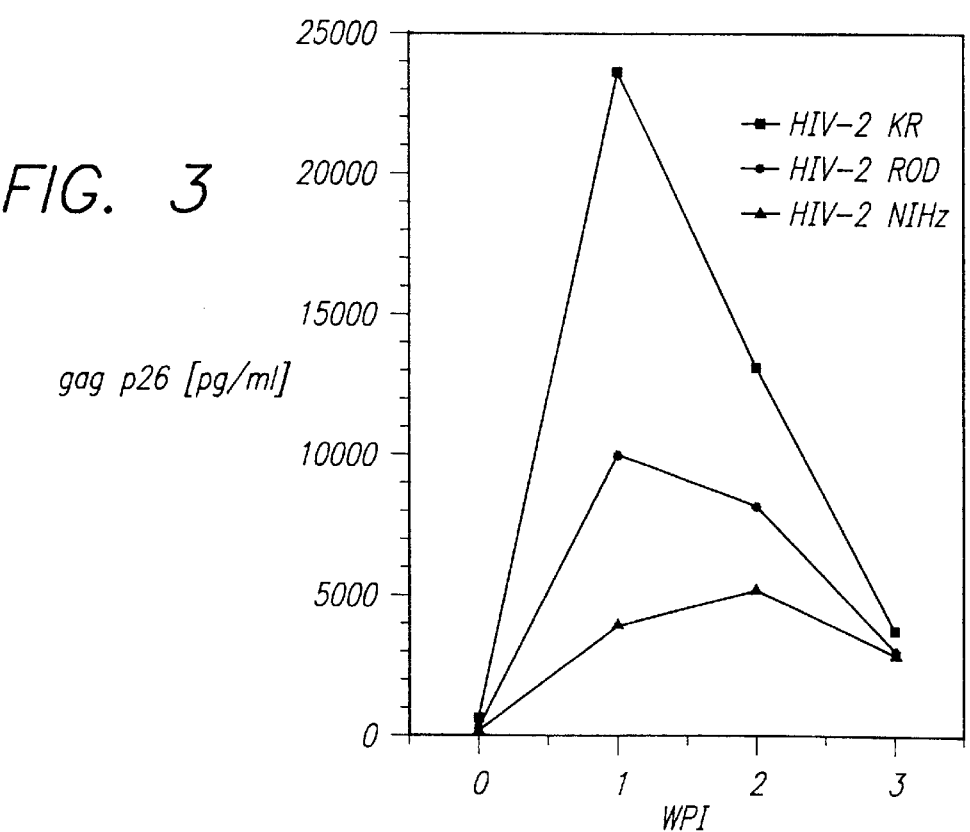
Figure 5:
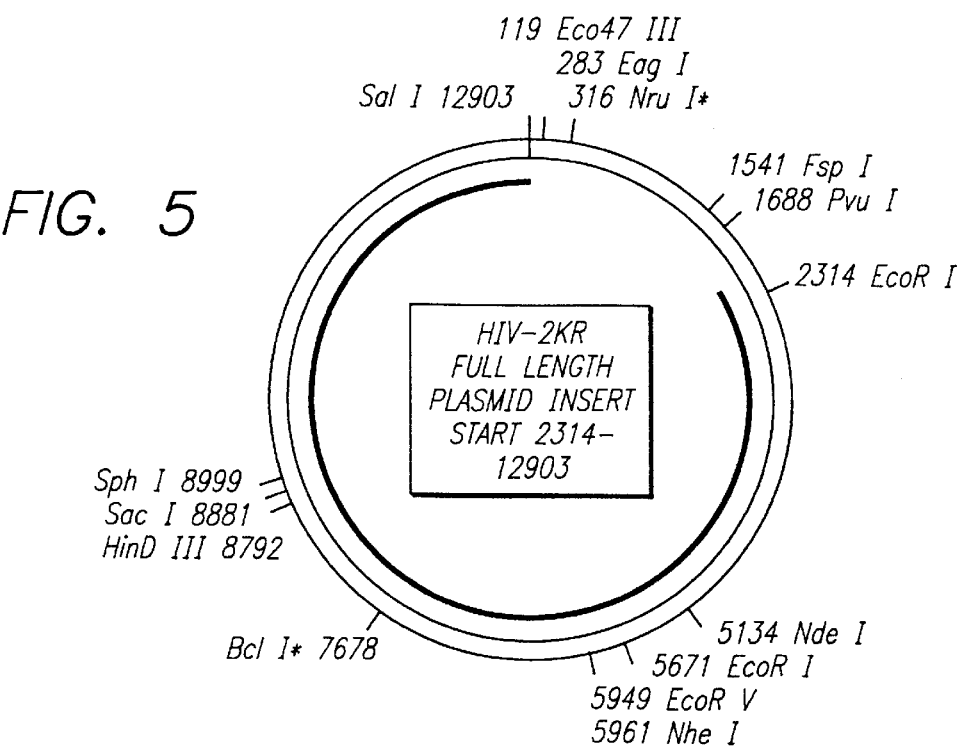
FIG. 5 is a restriction map for the D53 plasmid deposited with the ATCC.
Figure 6:
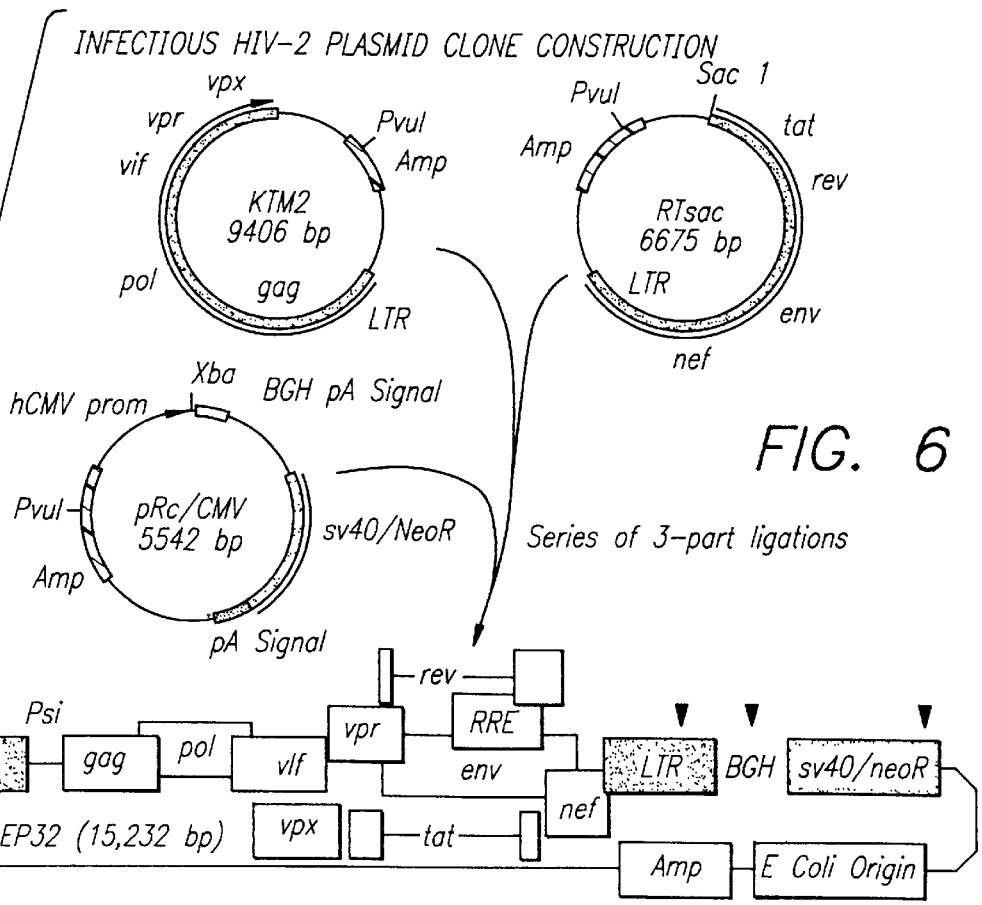
FIG. 6 shows the construction of infectious HIV-2 plasmid clone pEP32.
Figures 1, 7:
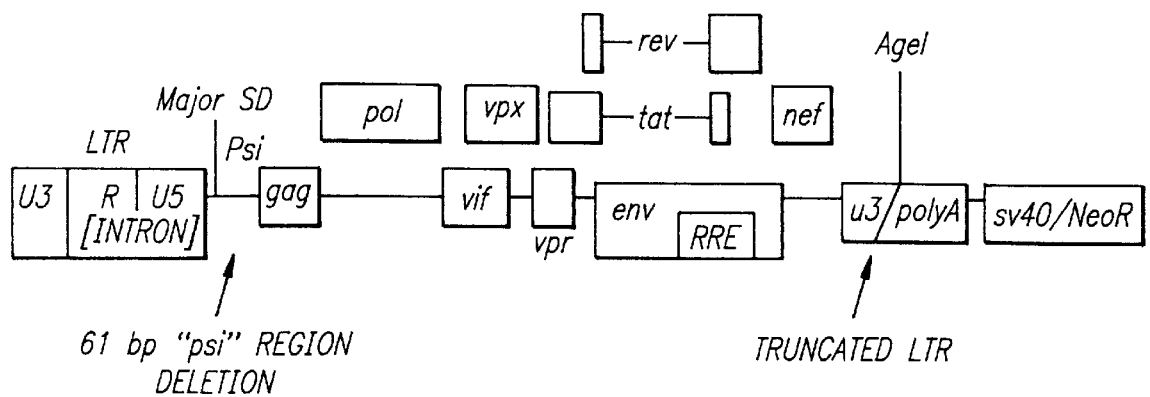
FIG. 7 shows the construction of HIV-2 protein expression vectors pEP40–pEP43.
Figures 2, 7:
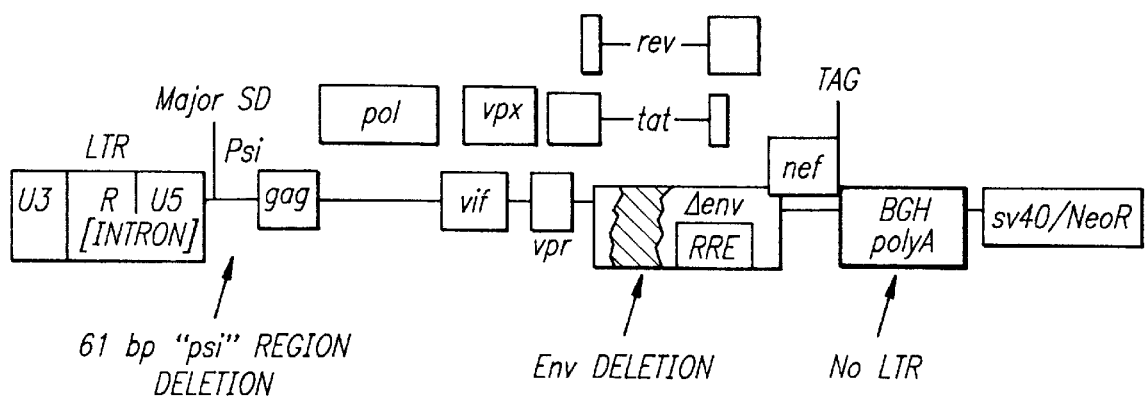
Figures 3, 7:
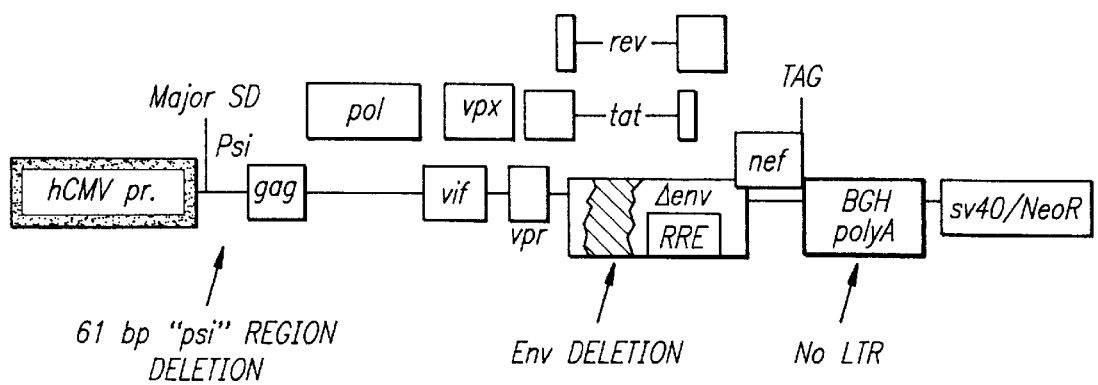
Figures 4, 7:
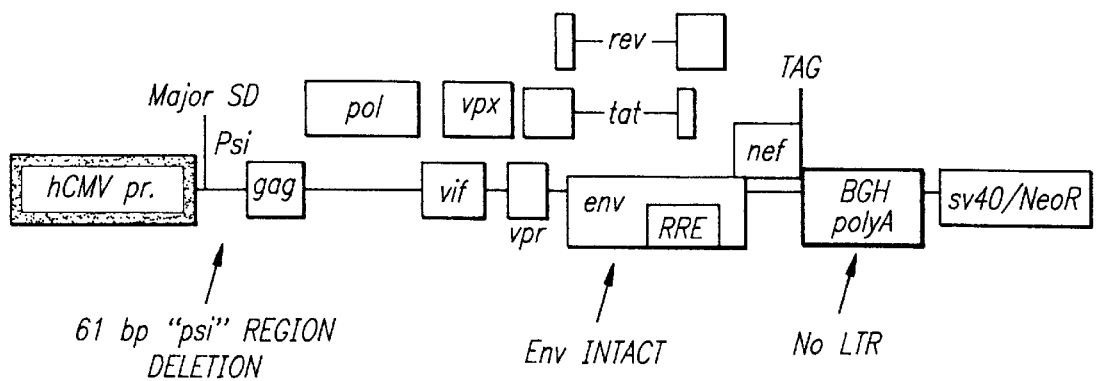

The infectivity of HIV-2$_{KR}$ was compared to that of HIV-2$_{SBL-ISY}$ and two uncloned HIV-2 isolates, HIV-2$_{NIHz}$ and HIV-2$_{ROD}$ on a variety of cell lines and primary human cells (see Table I.) HIV-2$_{KR}$ readily infected Molt 4/Clone 8 lymphoblastoid cells and HeLa T4 cells, as well as a number of other permanent human T cell lines (Molt-3, Molt-4, SupT1, H9, and C8166). The greatest cytopathic effect by HIV-2$_{KR}$ was evident in Molt-4/8 and SupT1 cells. Both molecular clones (HIV-2$_{KR}$ and HIV-2$_{ISY}$) exhibited reduced infectivity for primary macaque PBMC compared to uncloned isolates (HIV-2$_{ROD}$, HIV-2$_{NIHz}$), requiring 10–100× more viral antigen for each tissue culture infectious unit. As for other previously described HIV-2 isolates and clones (Romieu, et al. (1990) *Journal of Acquired Immune Deficiency Syndromes* 3, 220–30; Naucler, et al. (1993) *International Journal of STD and Aids* 4, 217–21; Naucler, et al. (1991) *Aids* 5, 301–4; O'Brien, et al. (1991) *Aids* 5, 85–8; Castro, et al. (1990) *Virology* 178, 527–34; Kirchhoff, et al. (1990) *Aids* 4, 847–57), HIV-2$_{KR}$ was also infectious for human monocytes, and produced markedly higher levels of virus after infection of monocyte-macrophages than did HIV-2$_{ROD}$ or HIV-2$_{NIHz}$, when inocula were adjusted to represent equivalent amounts of infectious virus on T-lymphocytes (FIG. 3). Although HIV-2$_{KR}$ replicated efficiently in monocytes and macrophages and was highly cytopathic in T-cell lines, few multinucleate giant cells were observed in HIV-2$_{KR}$ infected monocyte-macrophage cultures (FIG. 4). In contrast, HIV-2$_{ROD}$ and HIV-2$_{NIHz}$ produced numerous large syncytia in both lymphoblastoid and monocytic cell cultures (FIG. 4).

Infection of *M. nemestrina* with HIV-2$_{KR}$

Eight juvenile *M. nemestrina* were inoculated with HIV-2$_{KR}$ at four infectious dose levels, as determined by in vitro titration ($10^4$, $10^3$, $10^2$, and $10^1$ SFU). Every four weeks blood was obtained from the inoculated animals, and infection monitored by cocultivation with Molt4/Clone8 cells for virus reisolation, PCR on DNA obtained from PBMC of each animal, EIA seroreactivity to transmembrane protein, and quantitation of plasma antigen (Coulter™ SIV EIA). The course of infection in two animals infected with $10^3$ SFU are shown in Table 2. Both animals became PCR positive by week 4, and remained positive for over 19 weeks. However, virus was reisolated from peripheral blood mononuclear cells only during a brief period, usually from 4–8 weeks after inoculation, concomitant with detection of viral antigen in plasma. Virus was not reisolated from animals receiving less than $10^3$ SFU, though evidence of infection was detected by PCR amplification of proviral DNA from peripheral blood lymphocytes in *M. nemestrina* receiving as little as $10^1$ SFU. Clinical illness after intravenous inoculation of up to $10^5$ SFU HIV-2$_{KR}$ was not observed. Numbers of CD4$^+$ lymphocytes decreased to as low as 50% of the baseline values following inoculation, returning to normal levels within 20 weeks following infection. Animal F90407, which received an inoculum of $10^3$ SFU, displayed transient seropositivity to transmembrane peptide antigen at weeks 6–8, when virus was no longer recoverable (Table 2). Both animals recognized multiple virus-specific bands on western blots up to one year after infection. Prior exposure to HIV-2$_{KR}$ was found to protect infected animals against disease produced upon challenge with highly pathogenic strains of HIV-2, demonstrating that the virus in its present form is an effective vaccine against HIV-2 infection.

Features of HIV-2$_{KR}$

While genotypically similar to previously described HIV-2 isolates, HIV-2$_{KR}$ possesses several unique features. For instance, the increased basal and stimulated activity of the HIV-2$_{KR}$ promoter is unique, and provides for the development of tat deleted viruses as attenuated vaccine candidates, a desirable option in light of the immunosuppressive and paracrine effects of tat (Subramanyam, et al. (1993) *Journal of Immunology* 150, 2544–53; Ensoli, et al. (1990) *Nature* 345, 84–6). The presence of a substantial deletion in an otherwise highly conserved LTR promoter region indicates that the deleted region is recognized by inhibitory factor(s), for example, via a mechanism similar to the reported YY1 mediated inhibition (Margolis, et al. (1994) *Journal of Virology* 68, 905–10) of HIV-1. HIV-2$_{KR}$ also has a unique long rev reading frame.

Like other HIV-2 isolates and clones, HIV-2$_{KR}$ is dual-tropic, infecting both primary blood lymphocytes and monocyte-macrophages as well as established T-cell lines cells. HIV-2$_{KR}$ is also capable of infecting macaque peripheral blood lymphocytes in vitro, and produces a productive and persistent, though naturally "attenuated" infection in live *M. nemestrina* (Table 2). Efficient infection of Hu-PBL-SCID mice was also observed, providing, inter alia, a small animal model for use of this molecular clone in addition to the *M. nemestrina* model discussed herein.

Example 2

Construction of a stable infectious HIV-$2_{KR}$ clone containing a selectable marker cassette An HIV-2 high efficiency packaging vector project was initiated by constructing a stable HIV-2 plasmid clone (pEP32) from lambda phage-derived subgenomic viral plasmids. This plasmid, pEP32, (FIG. 6) and its derivatives, contain all HIV-$2_{KR}$ genes as well as a selectable marker gene (neoR initially and subsequently the phleomycin resistance marker). The plasmids have remained stable through numerous modifications and allow antibiotic-selection of stable cell lines containing them.

Example 3

Modifications to the Selecteable HIV-$2_{KR}$ clone

A series of modifications to pEP32 were made to achieve three goals: (1) expression of the HIV-2 structural proteins in trans; (2) abrogation of viral replication and genomic RNA packaging and (3) reduction of the probability of replication-competent retroviruses (RCR) occurring in packaging cell lines. 61 (out of a total of 75) base pairs were deleted from the "psi" (putative packaging signal region) between the major 5' splice donor and the gag gene start codon (see, FIG. 7). Next, the 3' R repeat, U5 and a portion of U3 were replaced with the bovine growth hormone (BGH) polyadenylation signal (plasmid pEP40). As illustrated in FIG. 7, pEP 41–43 in this series terminate viral sequences precisely with the stop codon of nef, which is adjoined to the BGH poly A signal.

The psi-deleted pEP40–43 series include four permutations of the HIV-$2_{KR}$ LTR and the heterologous HCMV promoter with env-intact and env-deleted genomes. Plasmids pEP40 and pEP43 express the HIV-2 envelope, while pEP41 and pEP42 have a 776 bp deletion in the envelope gene (from nt 6780 to 7555; numbered according to convention with nucleotide 1 corresponding to the T of TGGATGGG at the start of the 5' LTR; see, the sequence listing herein and GenBank No. U22047) which renders the Env protein non-functional, but does not interfere with Tat and Rev regulation. Only env expression is abrogated. pEP41 and pEP42 can be used as first high efficiency packaging nucleic acids in which a second high efficiency nucleic acid supplies env in trans, decreasing the possibility that a recombinatorial event will produce a virulent virus. The constructs can also be used for VSV-G pseudotyping, in which a second construct supplies VSV envelope in trans. pEP42 and pEP43 express the HIV structural proteins from the human cytomegalovirus promoter, eliminating both LTRs. The hCMV promoter is joined to the HIV-2 genome just after U5, at nucleotide 864 numbered according to convention with nucleotide 1 corresponding to the T of TGGATGGG at the start of the 5' LTR; see, the sequence listings herein and GenBank No. U22047).

While the 776 bp deletion is conveniently constructed (the deletion spans two Nsi sites, and can be generated by cleavage with Nsi and ligation of the resulting ends of the env gene), one of skill will recognize that larger or smaller deletions of the env gene have similar effects on env expression.

Example 4

HIV-2 based Retroviral Vectors

As illustrated in FIG. 3, HIV-2 based retroviral vectors were constructed to have both LTRs, the psi region and, since the packaging signal is predicted by analogy to other retroviruses to extend into gag, a portion of that gene's p17 region. As expression of the p17 gag mRNA is Rev-dependent, the rev-response element (RRE) is placed downstream of this p17 fragment to confer stability and nuclear export upon the vector transcript in the presence of Rev. Therefore, both vector and internally-promoted (sv40 promoter) marker gene mRNAs can be expressed in the packaging cell, but only the sv40 promoted transcript was appreciably expressed in the target cell.

For transient pseudotyping experiments with pEP 41 and 42, a third plasmid phCMV-G , is included to express the VSV-G protein.

Example 5

Replication and Expression of HIV-2 based Retroviral Vectors

Although the packaging plasmid LTR modifications illustrated in Example 4 were incorporated to increase safety, the 61 bp deletion in the psi region of HIV-$2_{KR}$ (from nt 1007 to 1067, numbered according to convention with nucleotide 1 corresponding to the T of TGGATGGG at the start of the 5' LTR; see, the sequence listings herein and GenBank No. U22047) was alone sufficient to abrogate replication of the virus. As shown in FIG. 9, lipofection of pEP32 into the highly permissive T cell line Molt 4/clone 8 resulted in lytic infection, while lipofection of the psi-deleted (and otherwise wild-type) clone or psi+3'LTR-deleted clone (pEP40) resulted in both transient p26 production and transient syncytia formation (the latter being Env-mediated); however in the case of the psi-deleted clone, both p26 and syncytia disappeared from the culture by two weeks. Six month follow-up of these experiments revealed no detectable p26 by an antigen capture assay sensitive to 10 picomoles per ml.

$10^6$ Molt 4 clone 8 cells lipofected (DOTAP, Boehringer-Mannheim) with 10 $\mu$g of CsCl-purified plasmid DNA and supernatant was sampled at the indicated times in FIG. 9 for a p26 antigen capture assay (Coulter). The pEP32Δpsi- and pEP40-transfected cultures were terminated at 7 months. At 200 days, p26 levels remained undetectable.

Example 6

Viral antigen Expression by p418 Selected Cell Lines

Stably transformed lines were derived by G418-selection for pEP32 (wild-type), pEP34 (a wild-type plasmid lacking only the downstream BGH polyA signal) and pEP40 for a number of cell types. Stable cell lines were derived by selection and maintenance in G418 600 µg/ml after transfection of CsCl-purified plasmid DNA previously linearized in prokaryotic sequences. Adherent cell lines were derived using polybrene-DMSO transfection and suspension cell lines by lipofection. Single cell clones were obtained from 96-well plates seeded with limiting dilutions of cells resulting in less than 12 clones per plate. Viral titrations were carried out by end-point dilution infection of Molt4 clone 8 T cells in 96-well plates scored for syncytia at 10 days. p26 was assayed by the Coulter antigen capture kit.

Initially, levels of p26 expression were low in HeLa, Daudi, U937, T lymphoblastoid and other cell lines (FIG. 10).

However, CD4-negative monkey kidney epithelial cell lines (CV1 and COS) were readily selectable, clone well and express very high levels of viral proteins that were equal to or in excess of that produced by lytic T-cell line infection with wild type virus. As illustrated in FIG. 11, cells selected for both psi+3'LTR-deleted ("C4" series) and full-length infectious proviruses ("C5" series) expressed over 100 ng/ml of p26 and over 700 ng/ml in some clones. Single cell clones routinely expressing 300–500 ng p26/ml were derived. Both COS-1 and CV-1 cells expressed high levels of p26, however, virus from COS-1 cells was a log more infectious per unit of p26. Clones selected for the wild-type provirus produced $5 \times 10^6$ TCID50/ml of HIV-2 (limiting dilution titer on Molt-4/clone-8 T cells) indicating normal processing and virion maturation from these cells.

Example 7

Safety of Packaging Cell Lines

Since numerous CD4-negative cell types have been shown to be infectable by HIV, it was important to document that these producer and packaging lines produced particles from the transfected DNA only (i.e., that replication or spread did not occur in these lines either in a cell-free or cell to cell manner). To that end, two experiments were performed.

First, passage of filtered wild-type HIV-2 supernatant with a titer of $10^6$ TCID50/ml to fresh COS-1 cells resulted in no detectable infection by p26 antigen capture assay or by PCR following trypsinization and cell passage.

Second, cell-cell spread was ruled out by the co-culture experiment illustrated in FIG. 12. A hygromycin-stable COS-1 cell line was generated and co-cultured at high density in a 1:1 ration with a G418-stable COS-1 clone (C5.8) selected for an infectious provirus and producing >300,000 pg/ml of p26 antigen as well as >$10^6$ TCID50/ml of virus. After several weeks of passage in co-culture, the mixed cells were then selected in hygromycin. 50% of the cells (the G418 stable producers) were observed to die. The remaining hygromycin-stable cell line was negative for p26 by antigen capture. Furthermore, no virus was rescuable by high volume co-culture with highly permissive T-lymphoblastoid lines such as Molt-4/clone-8, H9 and Jurkat. Thus, particles produced by these cell lines do not reinfect or spread within the culture and that expression is from the introduced plasmid DNA only.

Example 8

Packaging Cell Lines Express and Properly Process HIV-2 Product

To assess the ability of packaging cell lines to produce properly processed HIV-2 proteins, radioimmunoprecipitation using combined 35S-methionine and $^{35}$S-cysteine labeling was performed.

$^{35}$S Met and $^{35}$S Cys labeling was carried out for six hours following an initial three hour serum starvation. Following six-hour labeling, single cell-cloned and polyclonal lines were immunoprecipitated using a pooled human serum from five HIV-2-positive donors. Each cell line was simultaneously immunoprecipitated with an uninfected human control serum. No specific bands were precipitated from COS-1 cells alone or uninfected U937 cells, or in any cells precipitated with HIV-2-negative serum. However, cells selected for both the wild-type pEP34 (lines designated C5, single cell clones C5.X) and the psi/LTR-deleted packaging plasmid pEP40 (lines designated C4, single cell clones C4.X) revealed identical prominent bands specific for fully-processed HIV-2 structural proteins, including p17, p26, gp41, p55, and gp 140.

The results showed that the packaging signal deletion, extending to 10 bases downstream of the major 5' splice donor, and 3 bases upstream of the gag start codon, abrogated replication but did not interfere with proper viral mRNA processing and protein expression. Single cell cloning resulted in the selection of high-producers, as illustrated in a comparison of the C4 polyclonal cell immunoprecipitation experiments versus 8 C4 single cell clones.

Example 9

Packaging Cell Line Expression Plasmid Copy Number

Although the tested HIV-2 packaging plasmids contain the sv40promoter driving selectable marker expression, the high levels of expression obtained in G418-stable cell lines was not the result of either T-antigen driven amplification or episomal maintenance, as demonstrated by the following six lines of evidence.

First, Southern blotting revealed one or two proviral insertions for all of the cell line clones examined. 20 µg of Genomic DNA were digested with XbaI, which cleaves once within the introduced plasmid DNA upstream of neoR (FIG. 13). Cleavage in flanking genomic DNA outside the site of linearization (PvuI) produced a single, uniquely sized band for each plasmid copy insertion. XbaI-digested DNA was electrophoresed in 0.8% agarose, transferred to a nylon membrane and probed with a $^{32}$P-labeled probe randomly primed from a gel-purified 0.6 kb fragment of the neoR gene. The results showed that the cells had one or two proviral insertions. Single cell clones C4.2 and C4.4 each have a single proviral insertion and have been used for subsequent stable packaging line work.

Second, mutation of the T-antigen binding site within the Sv40 promoter resulted in equally high (>100 ng/ml) levels of expression in G418-selected lines. Third, a plasmid substituting an hCMV promoter-phleomycin resistance marker for the sv40-neoR cassette (thereby eliminating all sv40and T-antigen binding site sequences) was constructed and also gave high (>100 ng/ml p26) when used to derive stable COS-1 lines. Fourth, >95% (32/33) of G418-stable single cell clones derived for pEP32 or pEP34 produced infectious virus (although levels varied by orders of magnitude), indicating that gross rearrangements and deletions leading to selection for only the neoR encoding portion of the plasmid was uncommon. Fifth, G418-selected CV-1 cell clones, which were parental to COS cells, also produced >30 ng p26/ml. Sixth, Hirt DNA extracts were negative for plasmids, as tested by Southern blot and bacterial transformation.

To further characterize these cloned lines, electron microscopy was performed on several single cell clones. A transmission electron micrograph of C4.2 at 50,000× magnification showed the full range of normal virion particle maturation, from electron dense circular budding circular forms to fully mature, condensed conical cores. Numerous intracellular particles were also seen.

Example 10

Packaging of HIV-2 packagable RNAs

Figure 8:
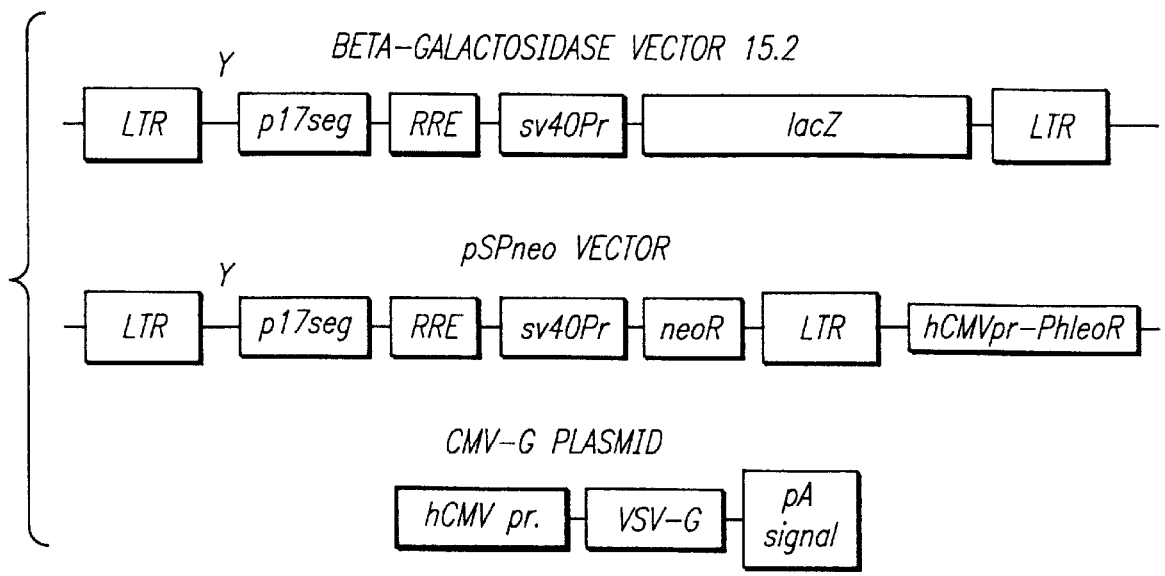
FIG. 8 shows the construction of the Beta-galactosidase Vector 15.2; the pSPneo vector, and the CMV-G plasmid.
Figure 9:
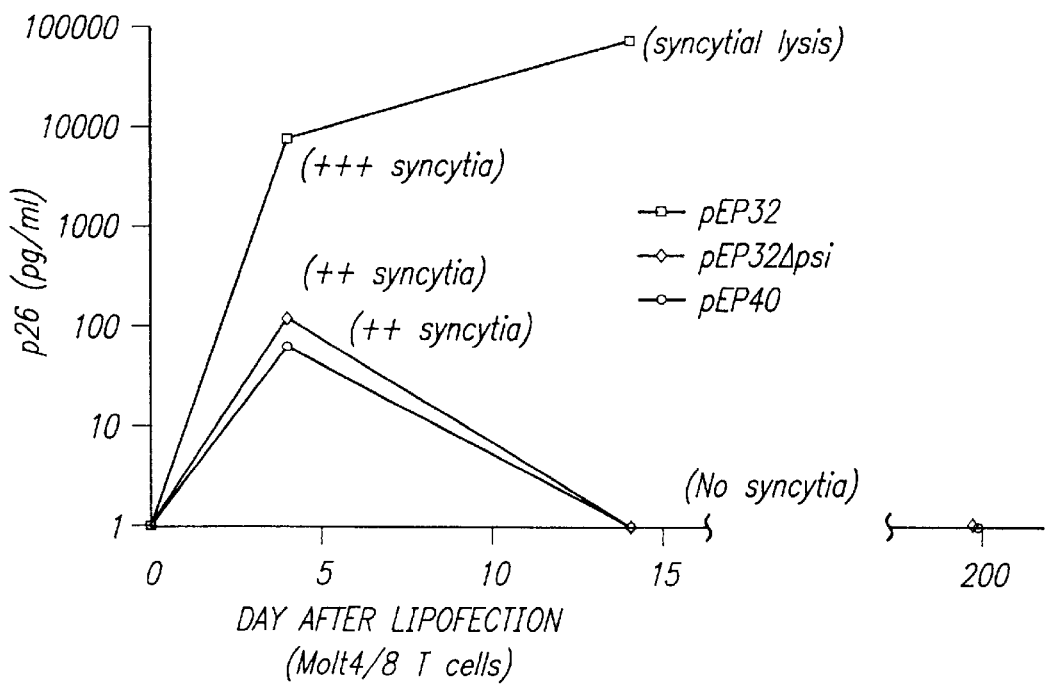
FIG. 9 shows the replication and expression of HIV-2 proviral constructs. 10⁶ Molt 4 clone 8 cells lipofected (DOTAP, Boehringer-Mannheim) with 10 μg of CsCl-purified plasmid DNA and supernatant was sampled at the indicated times for p26 antigen capture assay (Coulter). The pEP32Δpsi- and pEP40-transfected cultures were terminated at 7 months: at 200 days p26 levels remained undetectable.

C4.4 was transfected with linearized pSPneo (see, FIG. 8) and selected in phleomycin (200 4g/ml). Filtered supernatant was collected from the resulting G418+ phleomycin-stable cell line and serial dilutions (without polybrene) were used to transduce U937 cells, which were then selected in 400 μg/ml G418. Results are shown in Table 1 below. Cells transduced with heat-inactivated supernatant gave a titer of zero.

TABLE 1

NeoR titers obtained by transducing U937 cells with filtered supernatant from C4.4 spneo stable producer cell line

| HIV-2 Vector Stable Producer Cell Line Experiments (HIV-2 Envelope-mediated) | NeoR Titre | Mean |
|---|---|---|
| C4.4sPneo Stable Cell line Exp. 1; Transduction of U937 Cells | $1.3 \times 10^4$ | $1.8 \times 10^4$ |
| C4.4sPneo Stable Cell line Exp. 2; Transduction of U937 Cells | $8.5 \times 10^3$ | |
| C4.4sPneo Stable Cell line Exp. 3; Transduction of U937 Cells | $3.2 \times 10^4$ | |
| C4.4sPneo Stable Cell line Exp. 1-3; Heat Inactivated | 0 | |

Example 11

Pseudotype Vectors

Transient co-transfection of the VSV-G protein (see, Lin et al. (1994) Science 265:666) was used for transient pseudotyping of HIV-2 based vectors. Table 2 below describes the methods used to generated pseudotyped vector using triple transfection of pEP41, PEP15.2 and hCMV-G (see, FIGS. 7 and 8 for illustrations of plasmid structure). Omission of the VSV-G expression plasmid or heat inactivation abrogated gene transfer. Titers generated by calcium phosphate transfection of 293T cells and by COS-1 cell coelectroporation of these plasmids are shown in Table 2.

TABLE 2

Transduction of HeLa cells with VSV-g pseudotyped HIV-2 LacZ vector. Three plasmids: pEP41, pEP15.2 and CMV-G (15 μg each) were cotransfected by calcium phosphate co-precipitation into 293 T cells or co-electroporated into COS-1 cells plated a day earlier in 162 cm² flasks. 10–18 hours after transfection, transfected cells were washed and fresh medium was added. 48–72 hours later, the supernatant was collected and subjected to low-speed centrifugation and filtration (45 μm). HeLa cells plated the day before were incubated 36–48 hours further, with fresh medium. Titers represent number of blue-staining cells after 1–4 hours of X-gal staining divided by the dilution factor. No background was seen in control cells even after overnight staining. Heat inactivated (H.I.) supernatant (56° C., for 10 min) and transfections omitting the CMV-G plasmid yielded no positive cells.

| VSV-G Pseudotyped HIV-2 Vector Experiments | LacV Titer | Mean |
|---|---|---|
| 293 T cells; plasmids 41 + 15.2 + CMV-G; Exp. 1 | $8.6 \times 10^6$ | $3.8 \times 10^5$ |
| 293 T cells; plasmids 41 + 15.2 + CMV-G; Exp. 2 | $5.3 \times 10^5$ | |
| 293 T cells; plasmids 41 + 15.2 + CMV-G; Exp. 3 | $5.1 \times 10^5$ | |
| 293 T cells; plasmids 41 + 15.2; Exp. 1-3 | 0 | |
| 293 T cells; plasmids 41 + 15.2 + CMV-G; Exp. 1-3 (H.I) | 0 | |
| Cos-1 cells; plasmids 41 + 15.2 + CMV-G; Exp. 1 | $4.2 \times 10^4$ | $2.7 \times 10^4$ |
| Cos-1 cells; plasmids 41 + 15.2 + CMV-G; Exp. 2 | $1.5 \times 10^3$ | |
| Cos-1 cells; plasmids 41 + 15.2 + CMV-G; Exp. 3 | $3.8 \times 10^4$ | |
| Cos-1 cells; plasmids 41 + 15.2; Exp. 1-3 | 0 | |
| Cos-1 cells; plasmids 41 + 15.2 + CMV-G; Exp. 1-3 (H.I.) | 0 | |

Example 12

A Bioluminescent Marker For Retroviral Gene Transfer

The green fluorescent protein (GFP; see, Chalfie et al. (1994) Science 263:802) of the bioluminescent jellyfish Aequoria victoria was used as a marker for retroviral vector gene transfer. The principal advantages of this naturally fluorescent protein are its small size and the ability to detect it in living cells by simple UV-illumination (through either microscopy or flow cytometry). Shown in FIG. 14 is an HIV-2 based retroviral vector constructed by insertion of the s65t mutant of GFP (see, Helm et al (1995) Nature 373:663; Cubitt et al. (1995) Trends in Biochemical Sciences 20:448) in-frame in the nef gene. The resulting chimeric Nef/GFP fusion protein retains properties of both Nef and GFP (myristoylation-modulated confinement to intracellular membranous structures, and fluorescence respectively). Full-length infectious HIV-2 bearing this insertion transfers GFP to T cells with a low detectable transduction efficiency (approximately 2%). However, vector LXRTG, which is illustrated in FIG. 14, was also packaged with HIV-2 structural proteins from pEP41 and pseudotyped with VSV-G. The experimental design is illustrated in FIG. 14.

Photomicrographs 15 showed that when this supernatant (generated by calcium phosphate co-transfection into 293T cells according to the experimental design illustrated in FIG. 14) was used to transduce the monocytoid cell line U937, a transduction efficiency of >50% was achieved. A titer of $4 \times 10^5$ was obtained. Further modifications of this vector, which also expresses HIV-2 Tat, Rev, Vpr and Vpx, include deletion of these sequences. Although isolated stable expression of non-structural HIV-2 proteins is useful for a variety of basic experiments, clinically useful vectors preferably include substitution of HIV-2 coding sequences with an internal promoter such as SV40or the murine SL3—3 promoter.

All publications and patent applications cited in this specification are herein incorporated by reference for all purposes as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated HIV-2 provirus comprising a full-length HIV-2 genome, wherein:
the rev gene encoded by the provirus hybridizes to the second exon of the HIV-$2_{KR}$ rev gene as described in SEQ ID NO: 1 under stringent conditions;
the proviral LTR has an activating deletion; and,
the proviral LTR has high basal activity.

2. The HIV-2 provirus of claim 1, wherein the provirus is encapsidated in an HIV viral particle.

3. The HIV-2 provirus of claim 1, wherein the HIV-2 provirus comprises a sequence selected from the sequence of SEQ ID NO: 1 and conservatively modified variations thereof.

4. A recombinant cell which comprises the provirus of claim 1.

5. An immunogenic composition comprising the provirus of claim 1.

6. A composition of claim 5 comprising a pharmaceutically acceptable carrier.

7. A composition of claim 6, wherein the pharmaceutically acceptable carrier is an isotonic sterile injection solution.

8. An HIV-2 provirus comprising a full-length HIV-2 genome, wherein:
the provirus when encapsidated in an HIV viral particle encoded by the provirus, is replication competent in vitro in Molt-4/8 cells;
the provirus is infectious in primary human and macaque lymphocytes when encapsidated in an HIV viral particle;
the provirus, when encapsidated in an HIV viral particle encoded by the provirus, has reduced infectivity for macaque peripheral blood mononuclear cells compared to HIV-$2_{NIHZ}$ and HIV-$2_{rod}$;
the provirus, when encapsidated in an HIV viral particle encoded by the provirus, produces an attenuated infection in M. nemestrina;
the provirus, when encapsitated in an HIV viral particle encoded by the provirus, produces an infection in Hu-PBL-SCID mice;
the second exon of the rev gene encoded by the provirus encodes an amino acid sequence 180 amino acids in length;
the proviral LTR has an activating deletion; and,
the proviral LTR has high basal activity.

9. An isolated nucleic acid comprising a subsequence of the HIV-$2_{KR}$ provirus, wherein said subsequence is selected from the group of HIV-$2_{KR}$ nucleic acid sequences consisting of 30 contiguous nucleotides from the HIV-$2_{KR}$ genome, wherein the isolated nucleic acid binds to an HIV-$2_{KR}$ proviral nucleic acid under highly stringent conditions.

10. The isolated nucleic acid of claim 9, wherein said subsequence encodes a region of the HIV-$2_{KR}$ provirus selected from the group consisting of the HIV-$2_{KR}$ 3' LTR, the HIV-$2_{KR}$ 5' LTR, the HIV-$2_{KR}$ env gene, the HIV-$2_{KR}$ nef gene, the HIV-$2_{KR}$ rev gene, the HIV-$2_{KR}$ vpx gene, the HIV-$2_{KR}$ tat gene, the HIV-$2_{KR}$ gag gene, the HIV-$2_{KR}$ pol gene, the HIV-$2_{KR}$ vif gene, the HIV-$2_{KR}$ packaging site, and the HIV-$2_{KR}$ vpr gene.

11. A recombinant nucleic acid comprising the sequence of SEQ ID NO: 12.

12. A high efficiency HIV-2 packaging vector comprising a first high efficiency packaging vector nucleic acid, which first high efficiency packaging vector nucleic acid encodes a first portion of an HIV-2 particle, wherein
the encoded HIV-2 particle is non-virulent;
the first high efficiency packaging vector nucleic acid, when transfected into a cell, renders the cell competent to package HIV-2 packagable RNA with a titre of at least $1 \times 10^4$ transducing units per ml, wherein the HIV-2 packagable RNA comprises an HIV packaging site; and,
the first high efficiency packaging vector nucleic acid comprises a deletion in the HIV-2 psi region as compared to a wild-type genomic HIV-2 nucleic acid.

13. The high efficiency packaging vector of claim 12, wherein the vector is derived from HIV-$2_{KR}$.

14. The high efficiency packaging vector of claim 12, wherein the vector is derived from HIV-$2_{KR}$ by deleting 61 bp from the HIV-$2_{KR}$ psi site.

15. The high efficiency packaging vector of claim 12, wherein the high efficiency packaging vector is selected from the group of packaging vectors consisting of pEP32, pEP40, pEP41, pEP42, and pEP43.

16. The vector of claim 12, wherein the cell transduced by the high efficiency packaging vector comprises a second high efficiency packaging vector nucleic acid, which second high efficiency packaging vector nucleic acid encodes a second portion of an HIV-2 particle, wherein the first and second high efficiency packaging vector nucleic acids are complementary.

17. An HIV-2 packaging cell line comprising the recombinant packaging vector of claim 12, wherein the packaging cell line is stable and wherein HIV-2 particles produced by the packaging cell line are non-virulent.

18. The packaging cell line of claim 17, wherein the recombinant packaging vector is derived from HIV-$2_{KR}$.

19. The packaging cell line of claim 18, wherein the cell further comprises a nucleic acid encoding a VSV-G protein.

20. The packaging cell line of claim 17, wherein the cell further comprises an HIV-2 packagable nucleic acid.

21. An isolated HIV-2 provirus particle comprising an HIV-2 packagable RNA, wherein the packagable RNA encodes an HIV-2 packaging sequence and does not encode one or more complete HIV-2 genes selected from the group of trans- active HIV-2 genes consisting of gag, pol, vif, vpx, vpr, env, rev, tat, and nef.

22. The HIV-2 particle of claim 21, wherein the particle further comprises a VSV-G envelope protein.

23. The HIV-2 particle of claim 21, wherein the HIV-2 packaging site is derived from HIV-$2_{KR}$.

24. The HIV-2 particle of claim 21, wherein the packagable nucleic acid further comprises an HIV-2 LTR, p17 subsequence, and HIV-2 RRE subsequence.

25. The HIV-2 particle of claim 24, wherein the HIV-2 LTR, p17 subsequence and HIV-2 RRE subsequence are derived from HIV-$2_{KR}$.

26. The HIV-2 particle of claim 25, wherein the packagable nucleic acid is selected from the group consisting of Beta galactosidase 15.2, and pSPneo.

27. The HIV-2 particle of claim 21, wherein the packagable nucleic acid comprises a nucleic acid which encodes a detectable label.

* * * * *

UNITED STATES PATENT AND TRADEMARK OFFICE
CERTIFICATE OF CORRECTION

PATENT NO.    : 5,883,081
DATED         : March 16, 1999
INVENTOR(S)   : Kraus, et al.

It is certified that an error appears in the above-identified patent and that said Letters Patent is hereby corrected as shown below:

"STATEMENT REGARDING FEDERALLY SPONSORED RESEARCH

This invention was made with government support under Grant No. AI29889, awarded by the National Institutes of Health; and by the Veterans Administration. The government has certain rights in the invention."

Signed and Sealed this

Nineteenth Day of October, 1999

Attest:

Q. TODD DICKINSON

Attesting Officer    Acting Commissioner of Patents and Trademarks